United States Patent [19]
Vallari et al.

[11] Patent Number: 5,922,533
[45] Date of Patent: Jul. 13, 1999

[54] RAPID ASSAY FOR SIMULTANEOUS DETECTION AND DIFFERENTIATION OF ANTIBODIES TO HIV GROUPS

[75] Inventors: Anadruzela S. Vallari; John R. Hackett, Jr., both of Libertyville; Robert K. Hickman, Mundelein; Vincent A. Varitek, Jr., Wildwood; Elizabeth C. Necklaws, Grayslake; Alan M. Golden, Wilmette; Catherine A. Brennan, Libertyville; Sushil G. Devare, Northbrook, all of Ill.

[73] Assignee: Abbott Laboratories, Abbott Park, Ill.

[21] Appl. No.: 08/912,129

[22] Filed: Aug. 15, 1997

[51] Int. Cl.$^6$ ........................................ C12Q 1/70
[52] U.S. Cl. ................ 435/5; 435/7.1; 435/948; 435/974; 435/975; 436/518; 436/535; 422/55; 422/56; 422/61; 530/350; 530/826
[58] Field of Search ............ 435/5, 7.1, 7.92, 435/948, 974, 975; 436/518, 523, 535; 422/55, 56, 61; 530/350, 826

[56] References Cited

U.S. PATENT DOCUMENTS

| | | |
|---|---|---|
| 4,361,537 | 11/1982 | Deutsch et al. . |
| 4,956,302 | 9/1990 | Gordon et al. . |
| 5,055,391 | 10/1991 | Montagnier et al. . |
| 5,073,484 | 12/1991 | Swanson et al. . |
| 5,120,643 | 6/1992 | Ching et al. . |
| 5,124,255 | 6/1992 | Bolling et al. . |
| 5,160,701 | 11/1992 | Brown, III et al. . |
| 5,304,466 | 4/1994 | De Leys et al. . |
| 5,322,769 | 6/1994 | Bolling et al. . |

FOREIGN PATENT DOCUMENTS

| | | |
|---|---|---|
| 0591914 | 4/1994 | European Pat. Off. . |

OTHER PUBLICATIONS

L. Gürtler et al., *Journal of Virology*, vol. 68 (3), pp. 1581–1585 (1994).
M. Haesevelde et al., *Journal of Virology*, vol. 68 (3), pp. 1586–1596 (1994).
R. De Leys et al., *Journal of Virology*, vol. 64 (3), pp. 1207–1216 (1990).
I. Loussert–Ajaka et al., *Lancet*, vol. 343, pp. 1393–1394 (1994).
C. Schable et al., *Lancet*, vol. 344, pp. 1333–1334 (1994).
L. Gürtler et al., *Journal of Virological Methods*, vol. 51, pp. 177–184 (1995).
F. Clavel, *Aids*, vol. 1, pp. 135–140 (1987).

*Primary Examiner*—Jeffrey Stucker
*Attorney, Agent, or Firm*—Andreas M. Danckers

[57] ABSTRACT

A method of performing a rapid assay for the simultaneous detection and differentiation of the analytes HIV-1 group M, HIV-1 group O and HIV-2 utilizing a sequence specific polypeptide of each analyte as capture reagents. An analytical device also is provided for performing the method which includes these capture reagents. Also provided is a test kit which includes the analytical device which further can include a positive and negative control.

19 Claims, 24 Drawing Sheets

⌐gp120
MIVTMRAMGK RNRKLGILYI VMALIIPCLS SSQLYATVYA GVPVWEDAAP 50

VLFCASDANL TSTEKUNVWA SQACVPTDPT PHEYLLTNVT DNFNIWENYM 100

VEQMQEDIIS LWDQSLKPCI QMTFMCIQMN CTDIKNNNTS GTENRTSSSE 150

NPMKTCEFNI TTVLKDKKEK KQALFYVSDL TKLADNNTTN TMYTLINCNS 200

TTIKQACPKV SFEPIPIYYC APAGYAIFKC.NSAEFNGTGK CSNISVVTCT 250

HGIKPTVSTQ LILNGTLSKE KIRIMGKNIS DSGKNIIVTL SSDIEITCVR 300

PGNNQTVQEM KIGPMAWYSM ALGTGSNRSR VAYCQYNTTE WEKALKNTAE 350

RYLELINNTE GNTTMIFNRS QDGSDVEVTH LHFNCHGEFF YCNTSEMFNY 400

TFLCNGTNCN NTQSINSANG MIPCKLKQVV RSWMRGGSGL YAPPIPGNLT 450

CISHITGMIL QMDAPWNKTE NTFRPIGGDM KDIWRNELFK YKVVRVKPFS 500

⌐r-gP41
VAPTPIARPV IGTGTHREKR AVGLGMLFLG VLSAAGSTMG AAATALTVQT 550

HSVIKGIVQQ QDNLLRAIQA QQELLRLSVW GIRQLRARLL ALETLIQNQQ 600

LLNLWGCKGR LICYTSVKWN ETWRNTTNIN QIWGNLTWQE WDQQIDNVSS 650

TIYEEIQKAQ VQQEQNEKKL LELDEWASLW NWLDITKWLW YIKIAIIIVG 700

ALIGVRIVMI VLNLVRNIRQ GYQPLSLQIP TRQQSEAETP GRTGEGGGDE 750

GRPRLIPSPQ GFLPLLYTDL RTIILWSYHL LSNLISGTQT VISHLRLGLW 800

ILGQKIIDAC RICAAVIHYW LQELQKSATS LIDTFAVAVA NWTDDIILGI 850

QRLGRGILNI PRRVRQGFER SLL                          873

FIG.1

┌─gp120                                              ┌─gp41
MIGGDMKDIW RNELFKYKVV RVKPFSVAPT PIARPVIGTG THREKRAVGL 50

GMLFLGVLSA AGSTMGAAAT ALTVQTHSVI KGIVQQQDNL LRAIQAQQEL 100

LRLSVWGIRQ LRARLLALET LIQNQQLLNL WGCKGRLICY TSVKWNETWR 150

NTTNINQIWG NLTWQEWDQQ IDNVSSTIYE EIQKAQVQQE QNEKKLLELD 200

EWASLWNWLD ITKWL 215

FIG.5

┌─CKS
MSFVVIIPAR YASTRLPGKP LVDINGKPMI VHVLERARES GAERIIVATD 50

HEDVARAVEA AGGEVCMTRA DHQSGTERLA EVVEKCAFSD DTVIVNVQGD 100

EPMIPATIIR QVADNLAQRQ VGMTTLAVPI HNAEEAFNPN AVKVVLDAEG 150

YALYFSRATI PWDRDRFAEG LETVGDNFLR HLGIYGYRAG FIRRYVNWQP 200
                                                    ┌─gp120
SPLEHIEMLE QLRVLWYGEK IHVAVAQEVP GTGVDTPEDL DPSTNSIGGD 250
                                         ┌─gp41
MKDIWRNELF KYKVVRVKPF SVAPTPIARP VIGTGTHREK RAVGLGMLFL 300

GVLSAAGSTM GAAATALTVQ THSVIKGIVQ QQDNLLRAIQ AQQELLRLSV 350

WGIRQLRARL LALETLIQNQ QLLNLWGCKG RLICYTSVKW NETWRNTTNI 400

NQIWGNLTWQ EWDQQIDNVS STIYEEIQKA QVQQEQNEKK LLELDEWASL 450

WNWLDITKWL 460

FIG.6

┌─gp120                                        ┌─gp41
MIGGDMKDIW RNELFKYKVV RVKPFSVAPT PIARPVIGTG THREKRAVGL 50

GMLFLGVLSA AGSTMGAAAT ALTVQTHSVI KGIVQQQDNL LRAIQAQQEL 100

LRLSVWGIRQ LRARLLALET LIQNQQLLNL WGCKGRLICY TSVKWNETWR 150

NTTNINQIWG NLTWQEWDQQ IDNVSSTIYE EIQKAQVQQE QNEKKLLELD 200

EWASLWNWLD ITKWLRNIRQ GYQPLSLQIP TRQQSEAETP GRTGE     245

FIG.7

┌─CKS
MSFVVIIPAR YASTRLPGKP LVDINGKPMI VHVLERARES GAERIIVATD 50

HEDVARAVEA AGGEVCMTRA DHQSGTERLA EVVEKCAFSD DTVIVNVQGD 100

EPMIPATIIR QVADNLAQRQ VGMTTLAVPI HNAEEAFNPN AVKVVLDAEG 150

YALYFSRATI PWDRDRFAEG LETVGDNFLR HLGIYGYRAG FIRRYVNWQP 200
                                              ┌─gp120
SPLEHIEMLE QLRVLWYGEK IHVAVAQEVP GTGVQTPEDL DPSTNSIGGD 250
                                              ┌─gp41
MKDIWRNELF KYKVVRVKPF SVAPTPIARP VIGTGTHREK RAVGLGMLFL 300

GVLSAAGSTM GAAATALTVQ THSVIKGIVQ QQDNLLRAIQ AQQELLRLSV 350

WGIRQLRARL LALETLIQNQ QLLNLWGCKG RLICYTSVKW NETWRNTTNI 400

NQIWGNLTWQ EWDQQIDNVS STIYEEIQKA QVQQEQNEKK LLELDEWASL 450

WNWLDITKWL RNIRQGYQPL SLQIPTRQQS EAETPGRTGE      490

FIG.8

```
                                             ┌─gp120                                                    ┌─gp41
                                             MIGGDMKDIW  RNELFKYKVV  RVKPFSVAPT  PIARPVIGTG  THREKRAVGL   50

GMLFLGVLSA  AGSTMGAAAT  ALTVQTHSVI  KGIVQQQDNL  LRAIQAQQEL  100

LRLSVWGIRQ  LRARLLALET  LIQNQQLLNL  WGCKGRLICY  TSVKWNETWR  150

NTTNINQIWG  NLTWQEWDQQ  IDNVSSTIYE  EIQKAQVQQE  QNEKKLLELD  200

EWASLWNWLD  ITKWLRNIRQ  GYQPLSLQIP  TRQQSEAETP  GRTGEGGGDE  250

GRPRLIPSPQ  GFLPLLYTDL  RTIILWSYHL  LSNLISGTQT  VISHLRLGLW  300

ILGQKIIDAC  RICAAVIHYW  LQELQKSATS  LIDTFAVAVA  NWTDDIILGI  350

QRLGRGILNI  PRRVRQGFER  SLL                                 373
```

FIG. 9

```
          ┌─CKS
          MSFVVIIPAR YASTRLPGKP LVDINGKPMI VHVLERARES GAERIIVATD  50

HEDVARAVEA AGGEVCMTRA DHQSGTERLA EVVEKCAFSD DTVIVNVQGD  100

EPMIPATIIR QVADNLAQRQ VGMTTLAVPI HNAEEAFNPN AVKVVLDAEG  150

YALYFSRATI PWDRDRFAEG LETVGDNFLR HLGIYGYRAG FIRRYVNWQP  200
                                                      ┌─gp120
          SPLEHIEMLE QLRVLWYGEK IHVAVAQEVP GTGVDTPEDL DPSTNSIGGD  250
                                                    ┌─gp41
          MKDIWRNELF KYKVVRVKPF SVAPTPIARP VIGTGTHREK RAVGLGMLFL  300

GVLSAAGSTM GAAATALTVQ THSVIKGIVQ QQDNLLRAIQ AQQELLRLSV  350

WGIRQLRARL LALETLIQNQ QLLNLWGCKG RLICYTSVKW NETWRNTTNI  400

NQIWGNLTWQ EWDQQIDNVS STIYEEIQKA QVQQEQNEKK LLELDEWASL  450

WNWLDITKWL RNIRQGYQPL SLQIPTRQQS EAETPGRTGE GGGDEGRPRL  500

IPSPQGFLPL LYTDLRTIIL WSYHLLSNLI SGTQTVISHL RLGLWILGQK  550

IIDACRICAA VIHYWLQELQ KSATSLIDTF AVAVANWTDD IILGIQRLGR  600

GILNIPRRVR QGFERSLL                                    618
```

FIG.10

```
         ┌─CKS
         MSFVVIIPAR YASTRLPGKP LVDINGKPMI VHVLERARES GAERIIVATD  50

HEDVARAVEA AGGEVCMTRA DHQSGTERLA EVVEKCAFSD DTVIVNVQGD  100

EPMIPATIIR QVADNLAQRQ VGMTTLAVPI HNAEEAFNPN AVKVVLDAEG  150

YALYFSRATI PWDRDRFAEG LETVGDNFLR HLGIYGYRAG FIRRYVNWQP  200
                                                         ┌─gp120
         SPLEHIEMLE QLRVLWYGEK IHVAVAQEVP GTGVDTPEDL DPSTNSMEGE  250

LTCNSTVTSI IANIDSDGNQ TNITFSAEVA ELYRLELGDY KLIEVTPIGF  300
                   ┌─gp36
         APTKEKRYSS APVRNKRGVF VLGFLGFLAT AGSAMGAASL TLSAQSRTLL  350

AGIVQQQQQL LDVVKRQQEM LRLTVWGTKN LQARVTAIEK YLKDQAQLNS  400

WGCAFRQVCH TTVPWVNDSL TPDWNNMTWQ EWEKRVHYLE ANISQSLEQA  450

QIQQEKNMYE LQKLNS                                      466
```

FIG.11

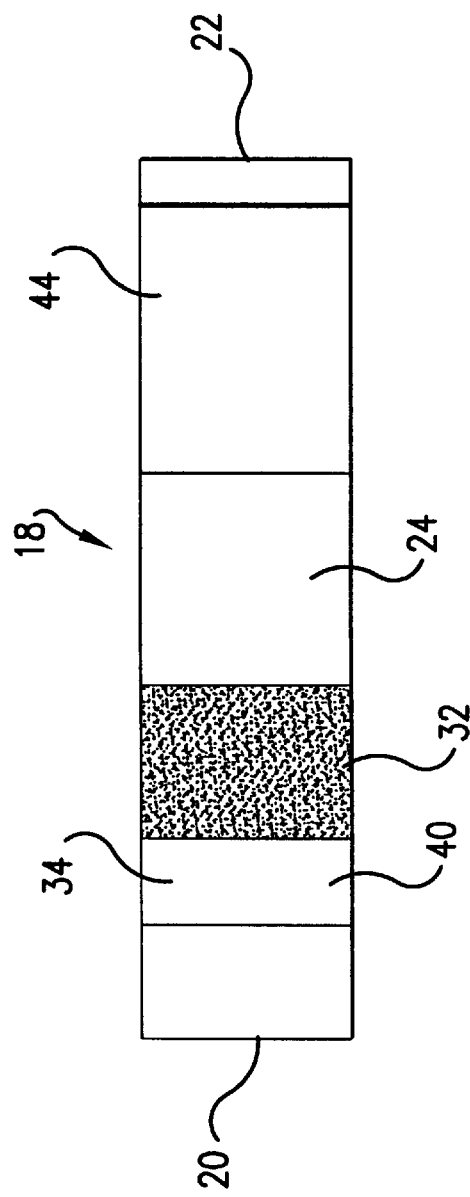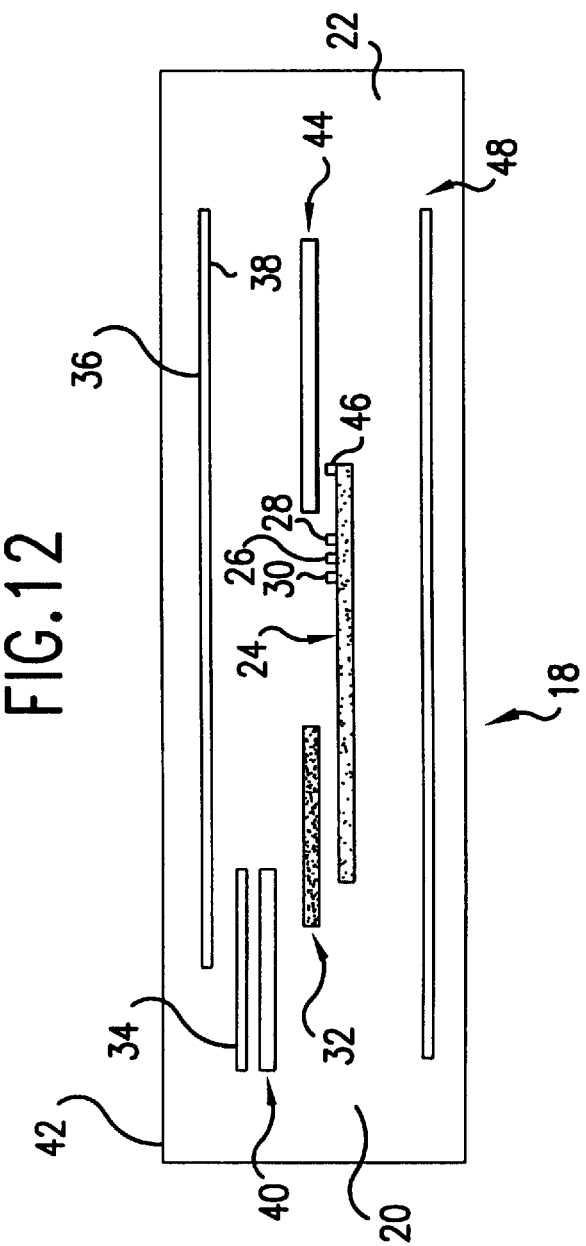

RAPID ASSAY FOR SIMULTANEOUS DETECTION AND DIFFERENTIATION OF ANTIBODIES TO HIV GROUPS

BACKGROUND OF THE INVENTION

This invention relates generally to immunoassays, and more particularly, relates to an immunoassay useful for detecting and differentiating antibodies to Human Immunodeficiency Virus Type 1 (HIV-1) group M, HIV-1 group O and Human Immunodeficiency Virus Type 2 (HIV-2) in test samples with a rapid turn-around time.

Currently, there are two major phylogenetic groups of HIV-1 designated as groups "M" and "O." G. Meyers et al., *Human Retroviruses and AIDS* 1995, Los Alamos National Laboratory, Los Alamos, N.Mex. (1995). HIV-1 group M isolates further have been divided into subgroups (A to J) that are phylogenetically approximately equidistant from each other. Group M isolates predominate worldwide. The earliest reports about the sequence of HIV-1 group O viruses indicated that these viruses were as closely related to a chimpanzee virus as to other HIV-1 subgroups. See, for example, L. G. Gürtler et al., *J. Virology* 68: 1581–1585 (1994); M. Vanden Haesevelde et al., *J. Virology* 68: 1586–1596 (1994); De Leys et al., *J. Virology* 64: 1207–1216 (1990); DeLeys et al., U.S. Pat. No. 5,304,466; L. G. Gürtler et al., European Patent Publication No. 0591914A2. The group O sequences are the most divergent of the HIV-1 sequences described to date. Although HIV-1 group O strains are endemic to west central Africa (Cameroon, Equatorial Guinea, Gabon, and Nigeria), patients infected with group O isolates now have been identified in Belgium, France, Germany, Spain and the United States. See, for example, R. DeLeys et al., supra; P. Charneau et al., *Virology* 205:247–253 (1994); I. Loussert-Ajaka et al., *J. Virology* 69:5640–5649 (1995); H. Hampl et al., *Infection* 23:369–370 (1995); A. Mas et al., *AIDS Res. Hum. Retroviruses* 12:1647–1649 (1996); M. A. Rayfield et al., *Emerging Infectious Diseases* 2:209–212 (1996), and M. Peeters et al., *AIDS* 11:493–498 (1997).

HIV-1 group M serology is characterized in large part by the amino acid sequences of the expressed viral proteins (antigens), particularly those comprising the core and envelope (env) regions. These antigens are structurally and functionally similar, but have divergent amino acid sequences that elicit antibody responses which are specific for the particular antigen.

One of the key serological targets for detection of HIV-1 infection is the 41,000 molecular weight transmembrane protein (TMP), glycoprotein (gp)41. gp41 is a highly immunogenic protein which elicits a strong and sustained antibody response in individuals considered seropositive for HIV. Antibodies to this protein are among the first to appear at seroconversion. The immune response to gp41 apparently remains relatively strong throughout the course of the disease, as evidenced by the near universal presence of anti-gp41 antibodies in asymptomatic as well as clinical stages of AIDS. A significant proportion of the antibody response to gp41 is directed toward a well-characterized immunodominant region (IDR) within gp41.

HIV-2 infections have been identified in humans outside of the initial endemic area of West Africa, and have been reported in Europeans who have lived in West Africa or those who have had sexual relations with individuals from this region, homosexuals with sexual partners from the endemic area, and others. Cases of AIDS due to HIV Type 2 (HIV-2) now have been documented world-wide. See, for example, A. G. Saimot et al., *Lancet* i:688 (1987); M. A. Rey et al., *Lancet* i:388–389 (1987); A. Werner et al., *Lancet* i:868–869 (1987); G. Brucker et al., *Lancet* i:223 (1987); K. Marquart et al., *AIDS* 2:141 (1988); CDC, MMWR 37:33–35 (1987); Anonymous, *Nature* 332:295 (1988).

Serologic studies indicate that while HIV-1 and HIV-2 share multiple common epitopes in their core antigens, the envelope glycoproteins of these two viruses are much less cross-reactive. F. Clavel, *AIDS* 1:135–140 (1987). This limited cross-reactivity of the envelope antigens is believed to explain why currently available serologic assays for HIV-1 may fail to react with certain sera from individuals with antibody to HIV-2. F. Denis et al., *J. Clin. Micro.* 26:1000–1004 (1988). Recently issued U.S. Pat. No. 5,055,391 maps the HIV-2 genome and provides assays to detect the virus.

Concerns have arisen regarding the capability of currently available immunoassays for the detection of antibody to HIV-1 (group M) and/or HIV-2 to detect the presence of antibody to HIV-1 group O. I. Loussert-Ajaka et al., *Lancet* 343:1393–1394 (1994); C. A. Schable et al., *Lancet* 344:1333–1334 (1994); L. Gürtler et al., *J. Virol. Methods* 51:177–184 (1995). Compounding the problem of analyzing whether these immunoassays are capable of detecting group O is the limited availability of sera samples from patients who are infected with and/or have antibody to HIV-1 group O isolates. To date, few patients have been diagnosed with infection to HIV-1 group O isolates outside of west Central Africa, leading researchers to screen patients in west central African countries for the virus. Screening procedures in west central Africa have been hampered both by the time necessary to perform these assays as well as the equipment required to do so. Conventional binding assays available for detecting antibodies to HIV-1 group M, HIV-1 group O and HIV-2 usually take about two to four or more hours to reach a result. These assays further involve utilizing equipment including incubators and label reading devices that require electricity in order to operate. These assays incorporate specific binding members, usually antibody and antigen immunoreactants, wherein one member of the specific binding pair is labeled with a signal-generating compound (e.g., an antibody labeled with an enzyme, a fluorescent compound, a chemiluminescent compound, a radioactive isotope, a direct visual label, etc.). The test sample suspected of containing the analyte can be mixed with a labeled reagent, e.g., labeled anti-analyte antibody, and incubated for a time and under conditions sufficient for the immunoreaction to occur. The reaction mixture is subsequently analyzed to detect either that label which is associated with the analyte/labeled reagent complex (bound labeled reagent) or that label which is not complexed with analyte (free labeled reagent). The presence and/or amount of an analyte is indicated by the analyte's capacity to bind to a labeled reagent and binding member, which usually is immobilized or an insoluble complementary binding member.

There are situations and places in which the period of time usually required to perform these assays and report results is too long (i.e., two to four hours), or the equipment and/or electricity necessary to run the assay is not available. In such situations, a preferable test should be inexpensive, require little or no equipment, and provide a result for a screening assay in as little time as five minutes.

The use of reagent-impregnated teststrips in specific binding assays is well-known. See, for example, Deutsch et al., U.S. Pat. No. 4,361,537 and Brown et al., U.S. Pat. No. 5,160,701. In such procedures, a test sample is applied to one portion of the teststrip and is allowed to migrate or wick through the strip material. Thus, the analyte to be detected or measured passes through or along the material, possibly with the aid of an eluting solvent which can be the test sample itself or a separately added solution. The analyte migrates into or through a capture or detection zone on the teststrip, wherein a complementary binding member to the analyte is immobilized. The extent to which the analyte becomes bound in the detection zone can be determined with the aid of the labeled reagent which also can be incorporated into the teststrip or which can be applied separately.

In general, teststrips involve a material capable of transporting a solution by capillary action, i.e., a wicking or chromatographic action as exemplified in Gordon et al., U.S. Pat. No. 4,956,302. Different areas or zones in the teststrip contain the assay reagents needed to produce a detectable signal as the analyte is transported to or through such zones. The device is suitable both for chemical assays and binding assays and uses a developer solution to transport analyte along the strip. Also, to verify the stability and the efficacy of the assay reagents needed to produce the detectable signal, existing assays typically require at least that one or more strips from each manufacturing lot be separately assayed for both positive and negative controls.

Assay systems developed for the separate or concurrent detection of antibodies to HIV-1 group M, and/or HIV-1 group O and/or HIV-2 therefore must contain reagents which are useful for determining the specific presence of antibody to any or all of the viruses in a test sample while differentiating between them. The need therefore exists for reagents capable of reacting only with antibody to HIV group M, HIV group O and HIV-2, which reagents either exhibit no cross-reactivity or limited cross-reactivity with each other. It also would be beneficial to provide a disposable assay device which could incorporate these reagents and be used for screening individuals and providing results in a short amount of time.

SUMMARY OF THE INVENTION

The present invention provides a method for simultaneously detecting and differentiating between analytes comprising antibodies to HIV-1 group O, HIV-1 group M and HIV-2 in a test sample. The method comprises (a) contacting the test sample with an analytical device having a strip with a proximal end and a distal end, wherein the test sample moves from the proximal end to about the distal end by capillary action, and wherein the strip contains at least one immobilized capture reagent per analyte, for a time and under conditions sufficient to form capture reagent/analyte complexes by the binding of the analyte and the capture reagent; and (b) determining the presence of the analyte(s) by detecting a visible color change at the capture reagent site on the strip, wherein the capture reagent for HIV-1 group O comprises a polypeptide selected from the group consisting of SEQ ID NO: 48, SEQ ID NO: 50, SEQ ID NO: 52 and SEQ ID NO: 54, SEQ ID NO: 58, and SEQ ID NO: 60, the capture reagent for HIV-1 group M comprises a polypeptide SEQ ID NO: 56, and the capture reagent for HIV-2 comprises a polypeptide SEQ ID NO: 55. Preferably, the polypeptide capture reagent is prepared by recombinant technology, although it is contemplated that a purified protein (polypeptide) or a synthetic peptide may be utilized. The immobilized capture reagent can be configured as a letter, number, icon, or symbol. Further, the method comprises an indicator reagent contained within the strip in a situs between the proximal end and the immobilized patient capture reagent. The indicator reagent comprises a signal generating compound, which compound is selected from the group consisting of a chromogen, a catalyst, a luminescent compound, a chemiluminescent compound, a radioactive element and a direct visual label. Preferably, the indicator reagent comprises a direct visual label selected from the group consisting of colloidal metallic particles, colloidal non-metallic particles, dyed or colored particles, and liposomes. The indicator reagent further comprises selenium as a non-metallic particle. The test sample preferably is a body fluid. The body fluid is selected from the group consisting of whole blood, plasma, serum, urine, and saliva.

The present invention further provides an analytical device for simultaneous detecting and differentiating between HIV-1 group O, HIV-1 group M and HIV-2 in a test sample, comprising a strip with a proximal end and a distal end, wherein the test sample is capable of moving from the proximal end to about the distal end by capillary action, and wherein the strip contains at least one immobilized capture reagent per analyte, for binding of the analyte and the capture reagent; and wherein the capture reagent for HIV-1 group O comprises a polypeptide sequence selected from the group consisting of SEQ ID NO: 48, SEQ ID NO: 50, SEQ ID NO: 52, and SEQ ID NO: 54, SEQ ID NO: 58, and SEQ ID NO: 60, said capture reagent for HIV-1 group M comprises SEQ ID NO: 56, and said capture reagent for HIV-2 comprises SEQ ID NO: 55. The polypeptide preferably is produced by recombinant technology, although it is contemplated that purified protein (polypeptide) and synthetic peptides can be used. The analytical device further comprises an immobilized capture reagent that is configured as a letter, number, icon, or symbol. Further, the analytical device comprises an indicator reagent that is contained within the strip in a situs between the proximal end and the immobilized patient capture reagent. The indicator reagent comprises a signal generating compound which compound is selected from the group consisting of a chromogen, a catalyst, a luminescent compound, a chemiluminescent compound, a radioactive element, and a direct visual label. Preferably, the indicator reagent comprises a direct visual label selected from the group consisting of colloidal metallic particles, colloidal non-metallic particles, dyed or colored particles, and liposomes. The test sample preferably is a body fluid. The body fluid is selected from the group consisting of whole blood, plasma, serum, urine, and saliva.

In addition, the present invention provides a test kit for use in specific binding assays. The test kit comprises an analytical device for determining the presence or amount of HIV-1 group O, HIV-1 group M and HIV-2 specific antibodies in a test sample, and further comprises a strip having a proximal end and a distal end, wherein the test sample is capable of moving from the proximal end to about the distal end by capillary action, and wherein the strip contains an immobilized capture reagent that binds to a member selected from the group consisting of the analyte, an ancillary specific binding member and an indicator reagent. The capture reagent for HIV-1 group O comprises a polypeptide selected from the group consisting of SEQ ID NO: 48, SEQ ID NO: 50, SEQ ID NO: 52, and SEQ ID NO: 54, SEQ ID NO: 58, and SEQ ID NO: 60, said capture reagent for HIV-1 group M comprises SEQ ID NO: 56, and said capture reagent for HIV-2 comprises SEQ ID NO: 55. The polypeptide preferably is produced by recombinant technology. It is contemplated that a purified protein or a synthetic peptide also may be used. The indicator reagent comprises a signal generating compound which compound is selected from the group consisting of a chromogen, a catalyst, a luminescent compound, a chemiluminescent compound, a radioactive element and a direct visual label. Preferably, the indicator reagent comprises a direct visual label selected from the group consisting of colloidal metallic particles, colloidal non-metallic particles, dyed or colored particles, and liposomes. The test kit further comprises a positive reagent control and a negative reagent control.

BRIEF DESCRIPTION OF THE DRAWINGS

FIG. 1 presents the deduced amino acid sequence of the env protein from the HIV-1 group O isolate HAM112 (SEQ ID NO: 61).

Figure 2:
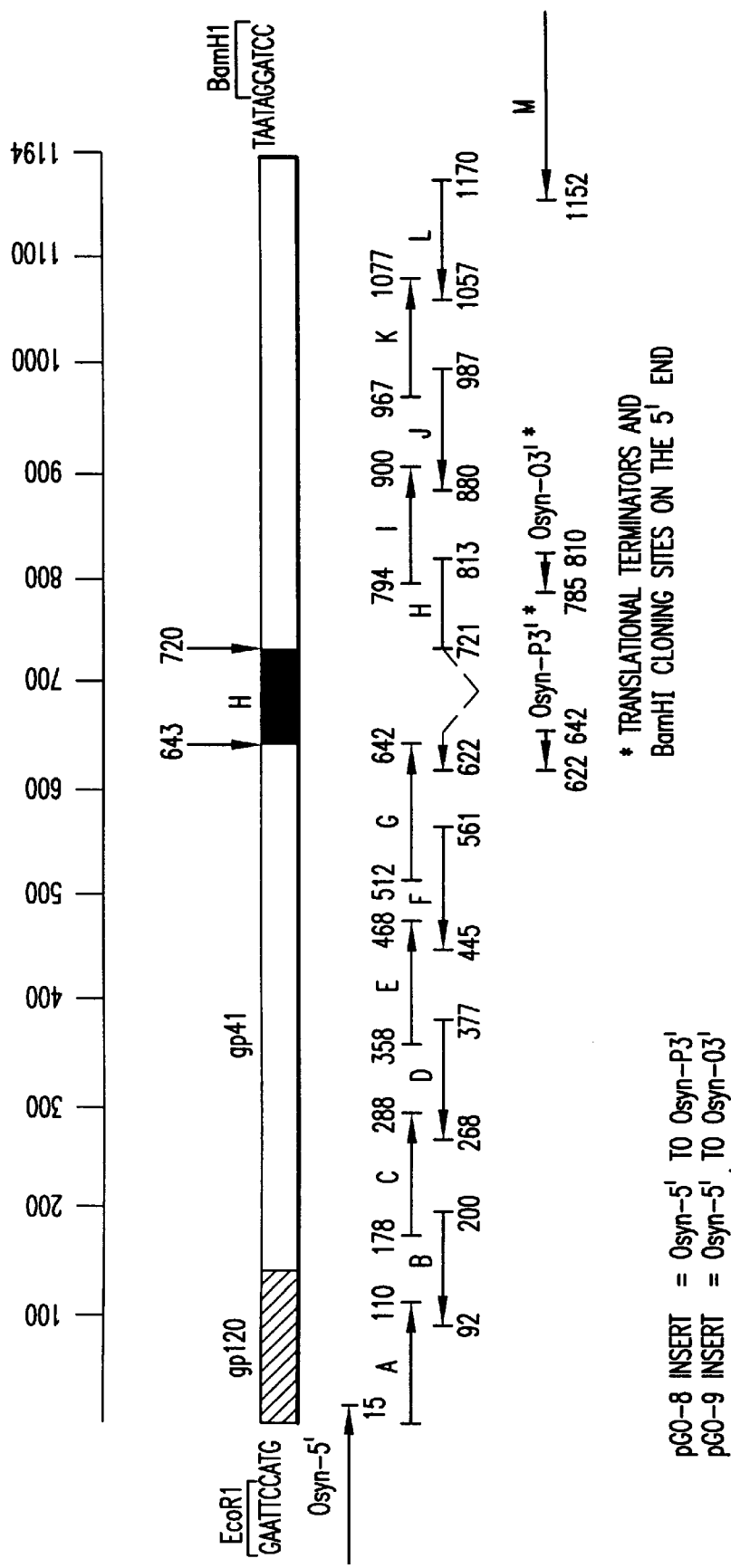
FIG. 2 depicts the strategy used to generate synthetic HIV-1 group O env gp120/gp41 gene constructs, wherein the pGO-8 insert=Osyn-5' to Osyn-P3'; pGO-9 insert=Osyn-5' to Osyn-03'; pGO-11 insert=Osyn-5' to Osyn-M; and wherein H=the hydrophobic region of HIV-1 group O, deleted as shown.
Figure 3A:
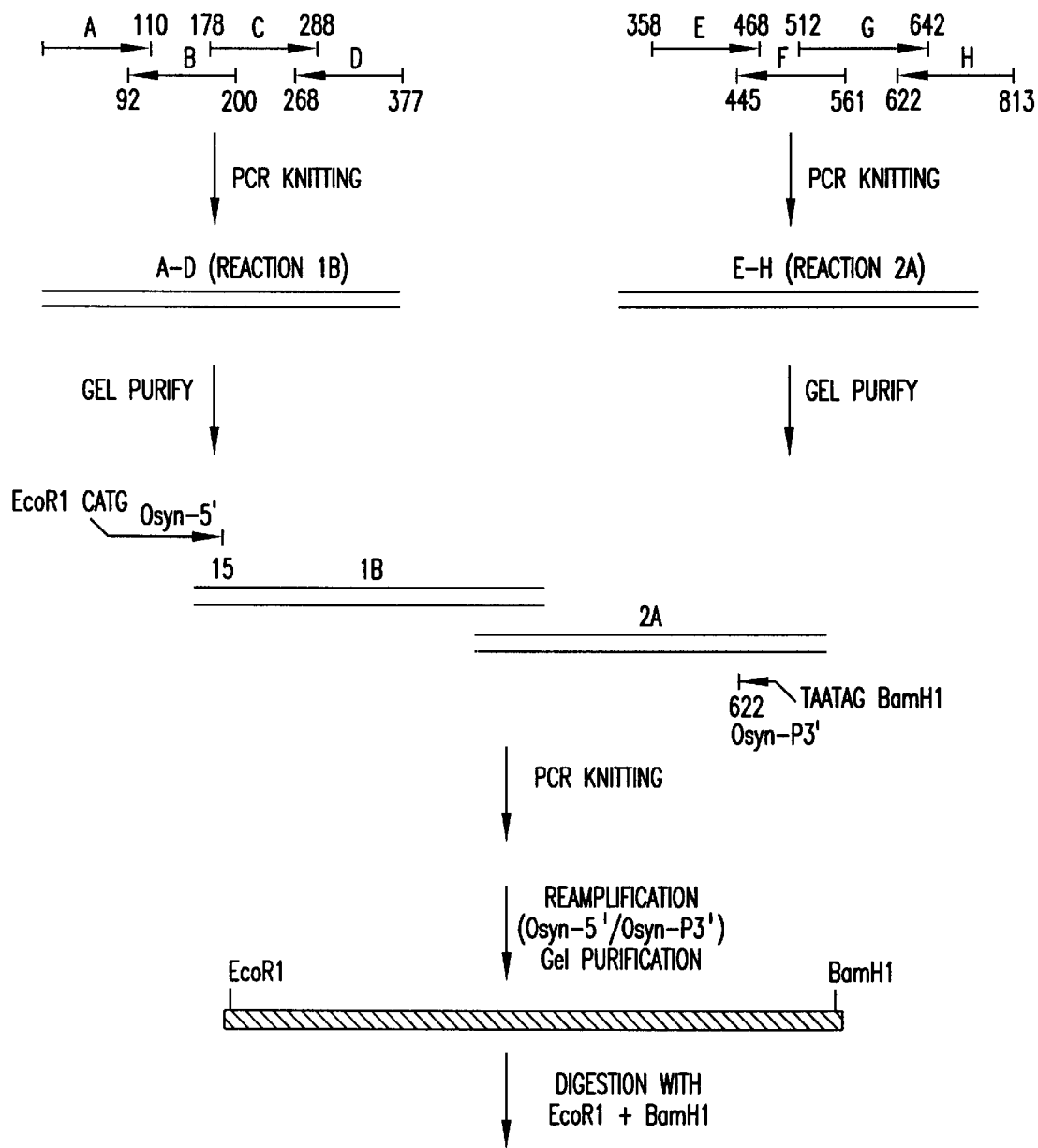
FIGS. 3A through 3D show a diagrammatic representation of the steps involved in construction of pGO-9PL/DH5α and pGO-9CKS/XL1.
Figure 3B:
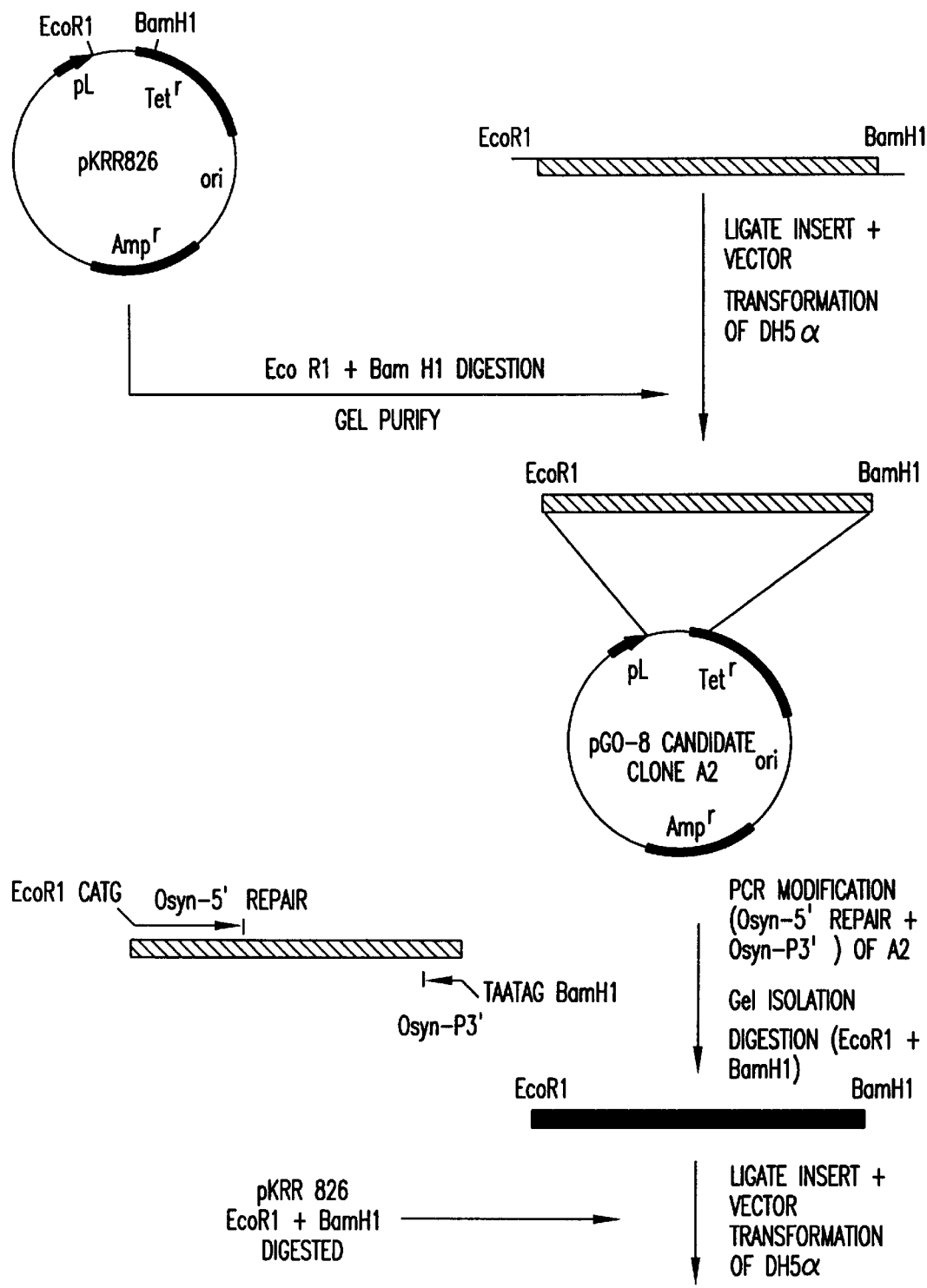
Figure 3C:
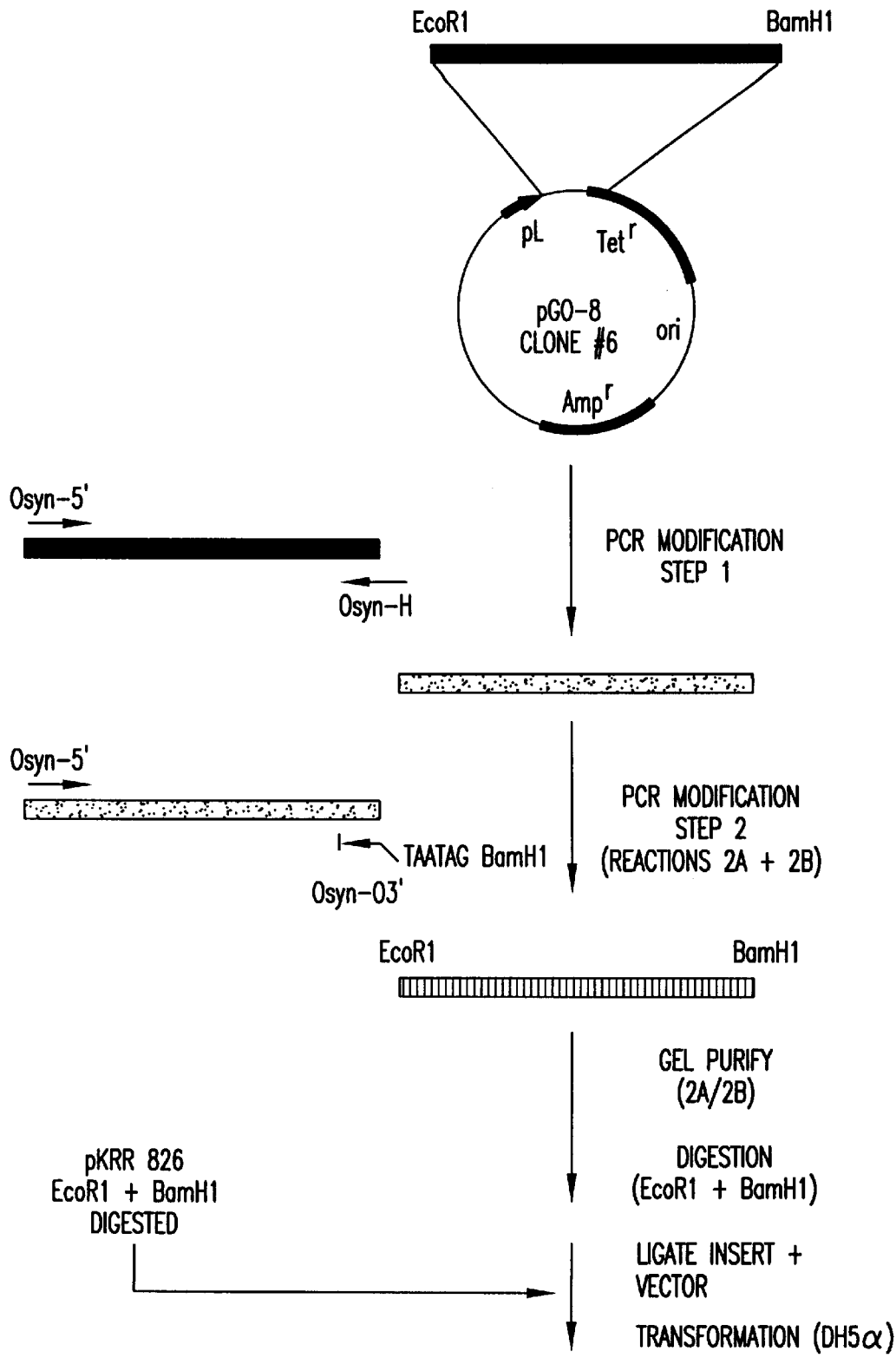
Figure 3D:
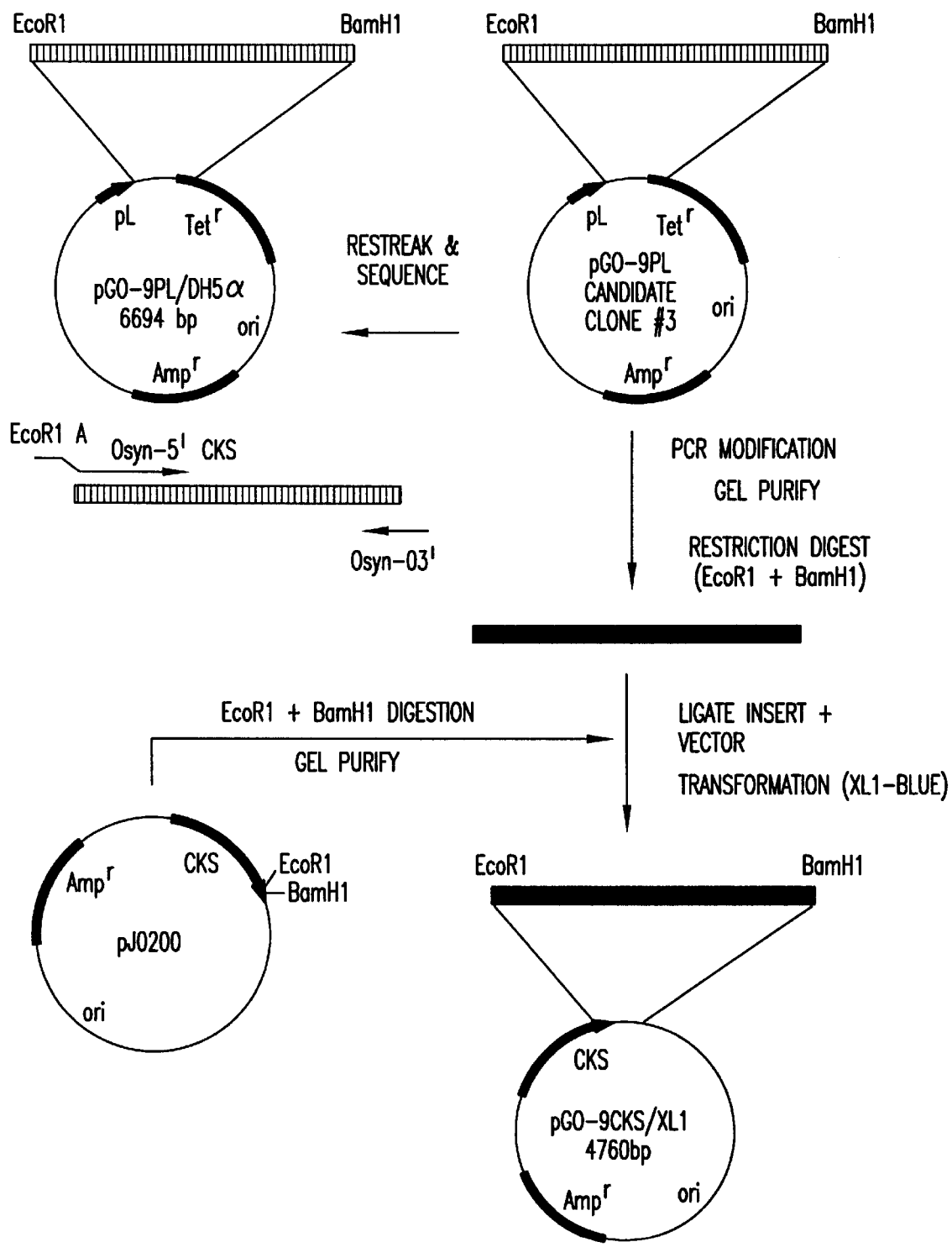
Figure 4A:
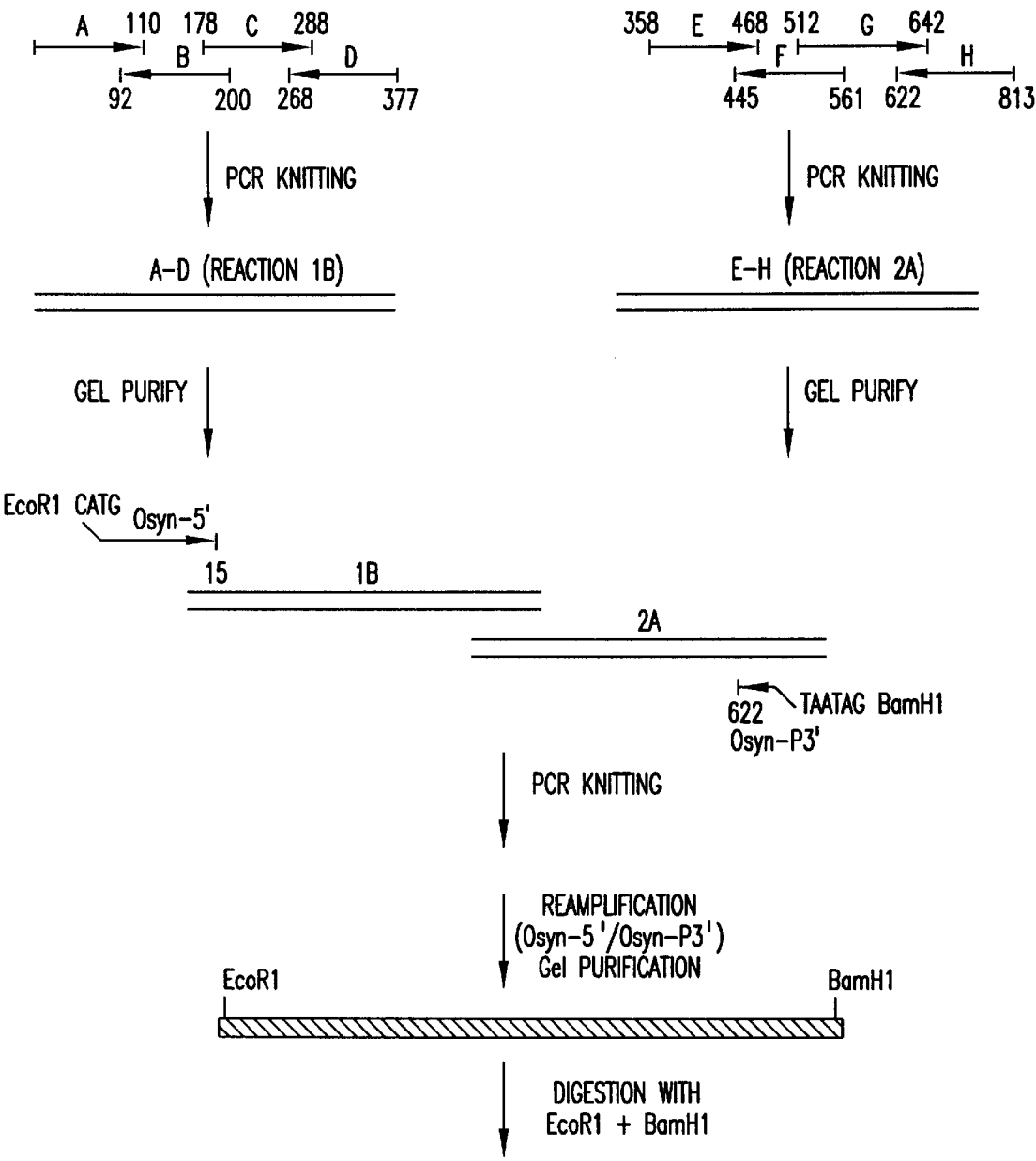
FIGS. 4A through 4G show a diagrammatic representation of the steps involved in construction of pGO-11PL/DH5α and pGO-11CKS/XL1.
Figure 4B:
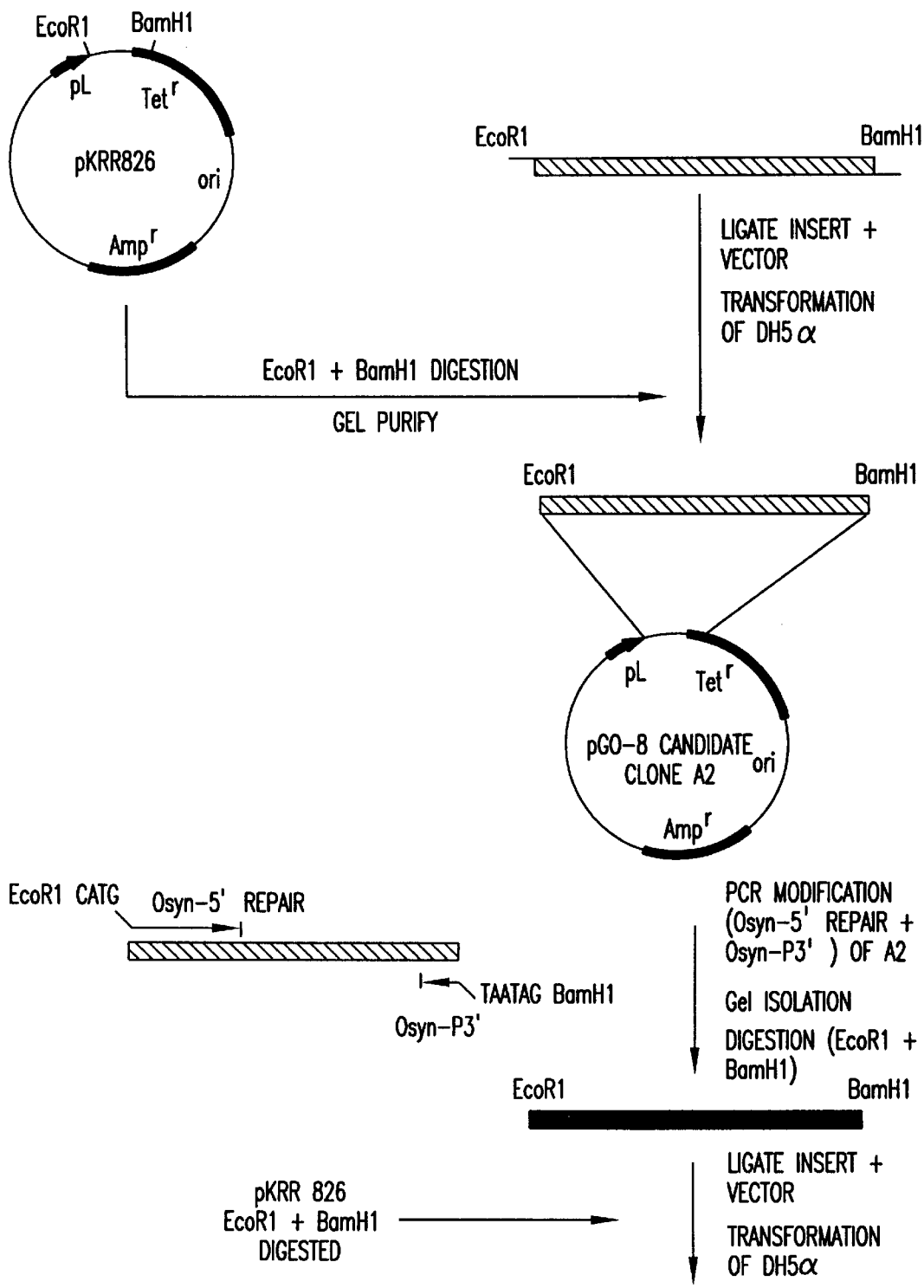
Figure 4C:
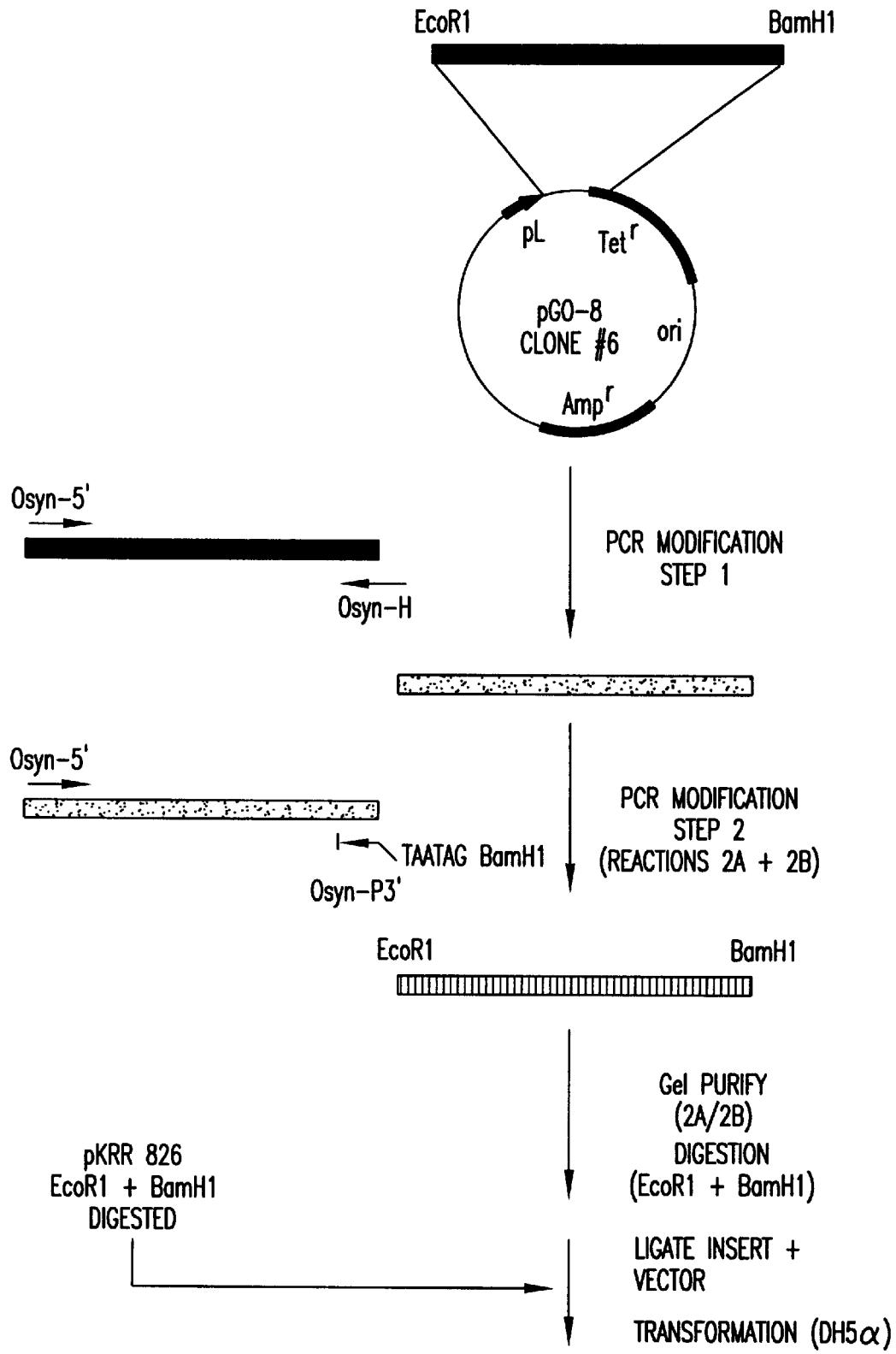
Figure 4D:
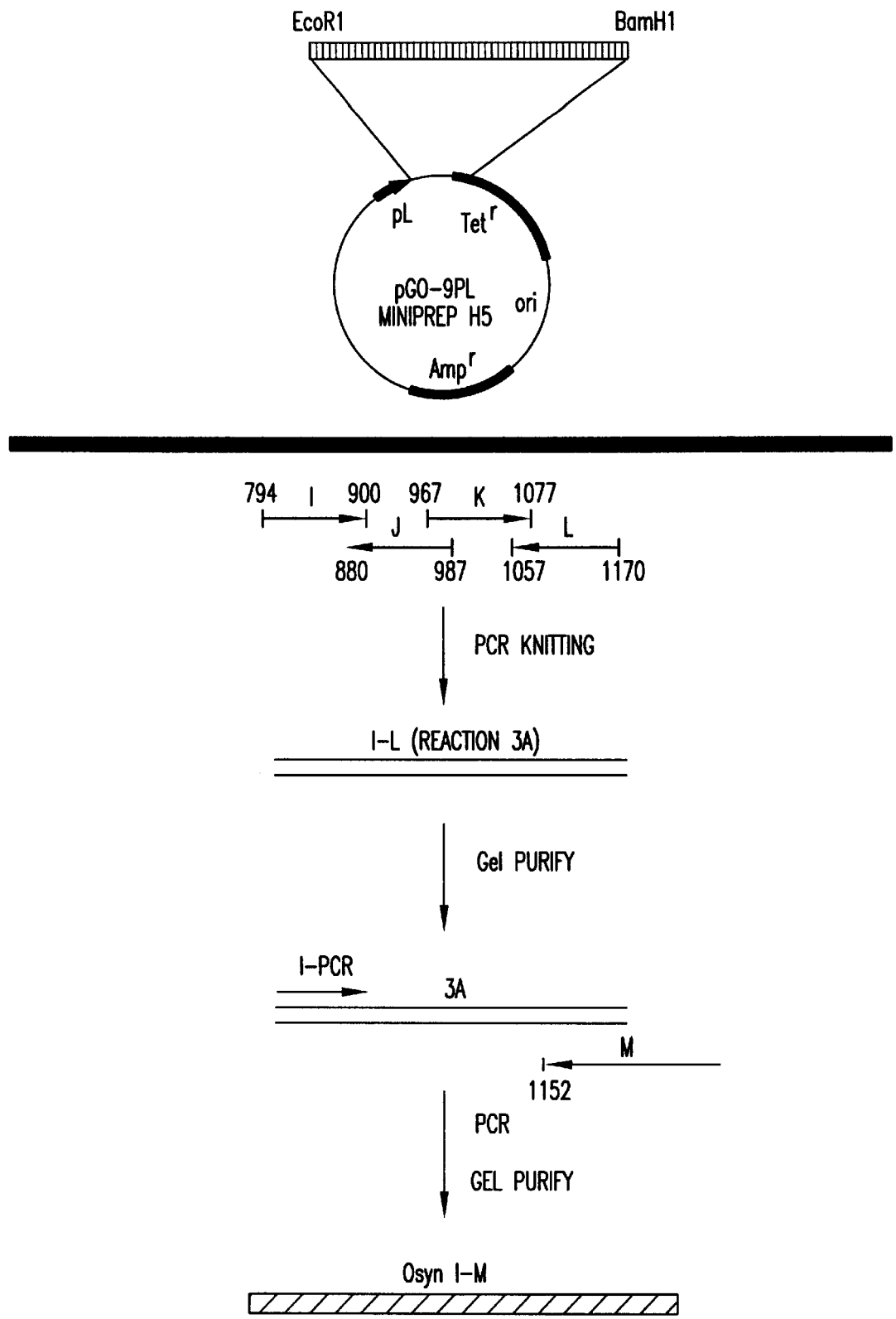
Figure 4E:
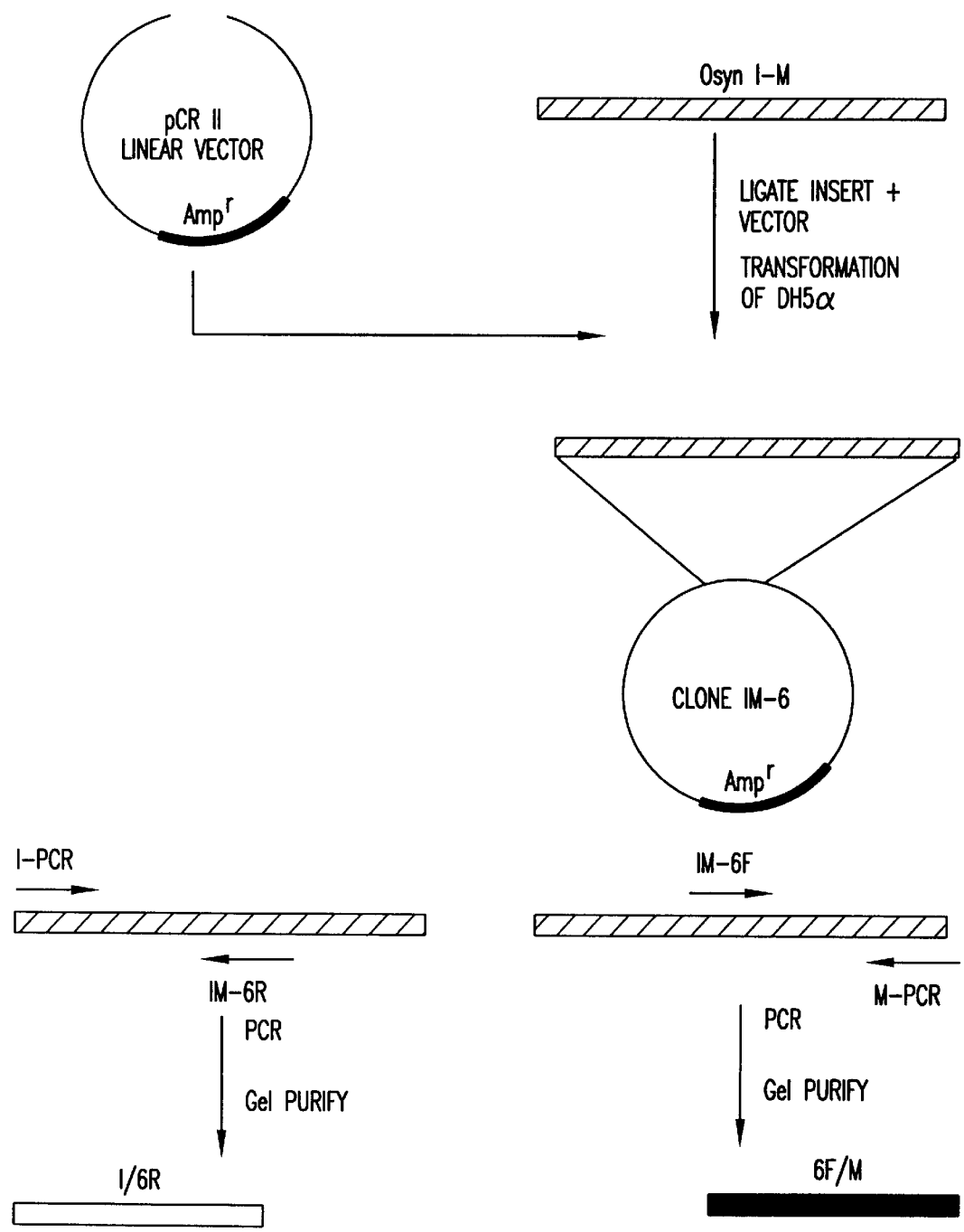
Figure 4F:
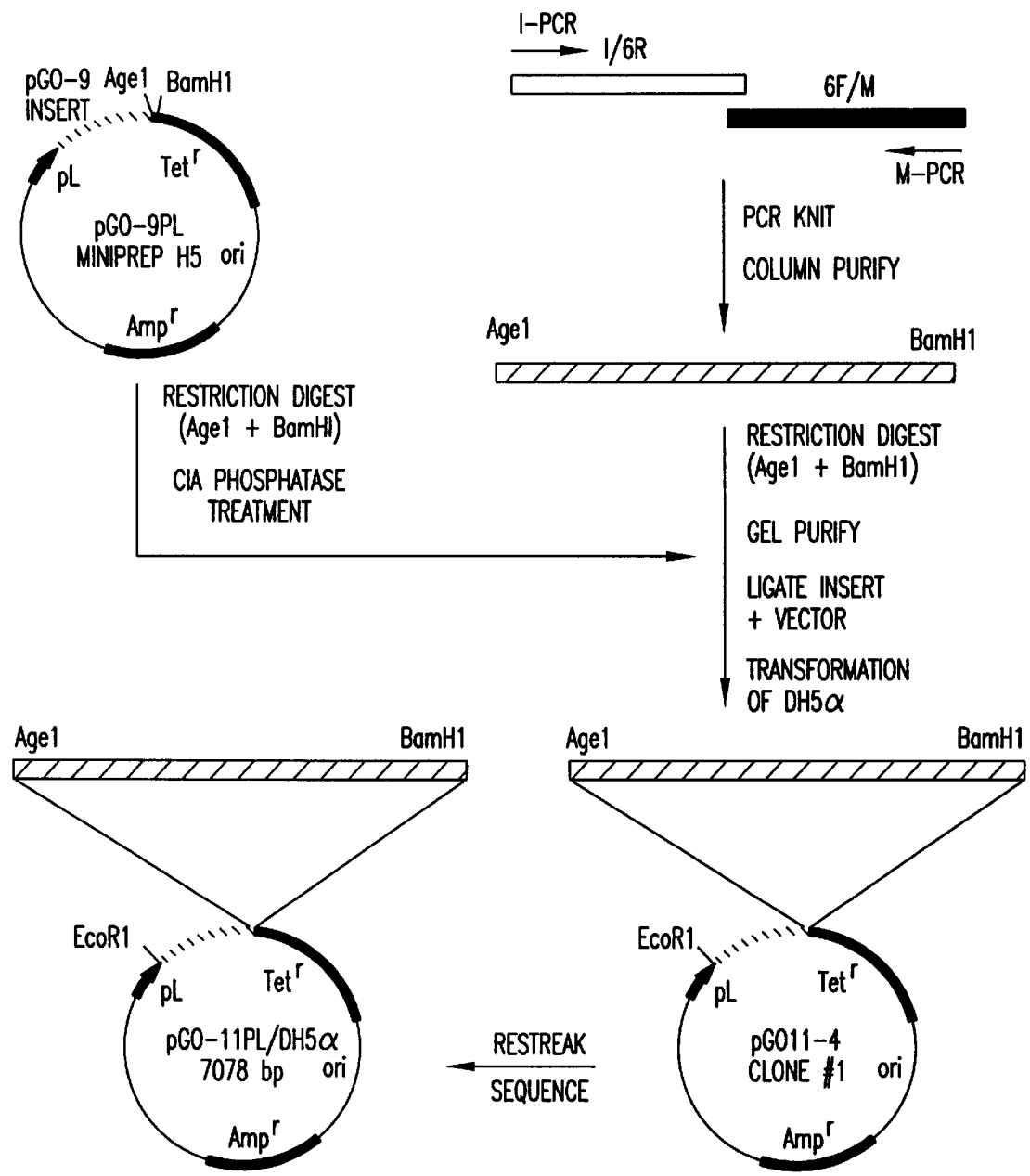
Figure 4G:
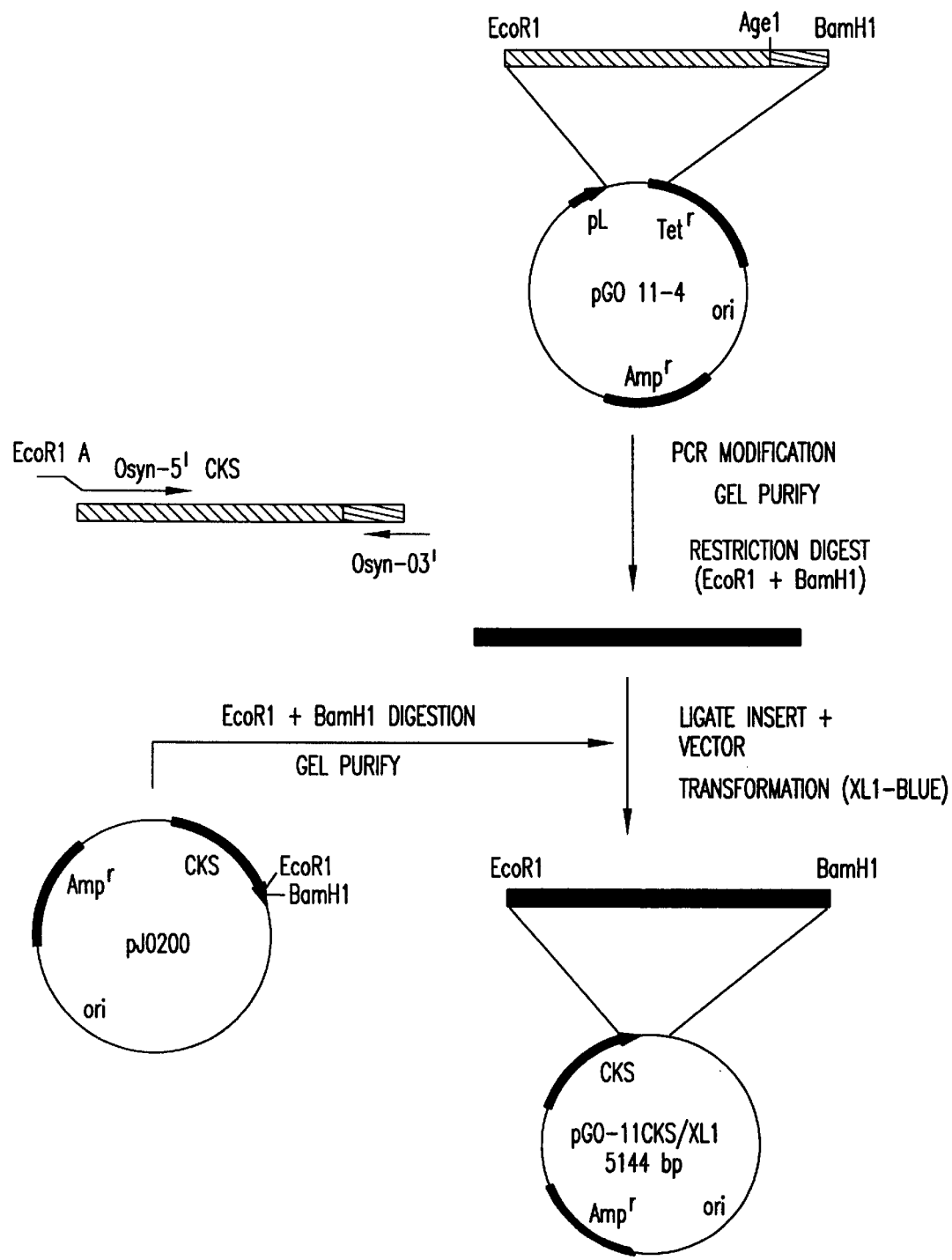

FIG. 5 illustrates the amino acid sequence of the pGO-8PL recombinant protein (SEQ ID NO: 58).

FIG. 6 shows the amino acid sequence of the pGO-8CKS recombinant protein (SEQ ID NO: 60).

FIG. 7 illustrates the amino acid sequence of the pGO-9PL recombinant protein (SEQ ID NO: 48).

FIG. 8 shows the amino sequence of the pGO-9CKS recombinant protein (SEQ ID NO: 50).

FIG. 9 illustrates the amino acid sequence of the pGO-11PL recombinant protein (SEQ ID NO: 52).

FIG. 10 shows the amino sequence of the pGO-11CKS recombinant protein (SEQ ID NO: 54).

FIG. 11 illustrates the amino acid sequence of the pHIV-210 recombinant protein (SEQ ID NO: 55).

FIG. 12 is a front plan view of the test device utilized for the present invention.

FIG. 13 is a cross-section view of the test device shown in FIG. 12, taken along lines (20)–(22) of FIG. 12.

FIG. 14 is a photograph of the results obtained in four test devices of (from left to right) two negative serum samples (two test devices to the left) and two negative whole blood test samples (two test devices to the right) spiked with a negative control in the assay of the invention.

FIG. 15 is a photograph of ten test devices and shows the results obtained testing (from left to right) five HIV-1 group M sera (five test devices to the left) and five whole blood samples (five test devices to the right) spiked with the HIV-1 group M positive sera.

FIG. 16 is a photograph of four test devices showing the results obtained when testing (from left to right) two confirmed positive HIV-1 group O sera (two test devices to the left) and two whole blood test samples spiked with HIV-1 group O sera (two test devices to the right).

FIG. 17 is a photograph of ten test devices showing the results obtained with (from left to right) five HIV-2 confirmed positive sera (five test devices to the left) and whole blood spiked with HIV-2 sera (five test devices to the right).

FIG. 18 is a photograph of four test devices, in which (from left to right) a negative test sample, an HIV-1 group M positive test sample, an HIV-1 group O positive test sample, and an HIV-2 positive test sample were tested individually.

DETAILED DESCRIPTION OF THE INVENTION

The ability to screen for HIV-1 group M, HIV-1 group O and HIV-2 in less time than conventional assays is a required feature in situations in which quick results are necessary for patient counseling and treatment. Such a screening assay must be able to provide a similar degree of sensitivity and specificity as the conventional screening assays, but in a much shorter period of time. The present invention provides such an assay and is described hereinbelow.

The following terms have the following meanings unless otherwise noted:

The term "test sample" refers to a component of an individual's body which is the source of the analyte (such as, antibodies of interest or antigens of interest).

These components are well-known in the art. The test sample can be used directly as obtained from the source or after pretreatment so as to modify its character. These test samples include biological samples which can be tested by the methods described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; and biological fluids such as cell culture supernatants; fixed tissue specimens; and fixed cell specimens. The test sample can be pretreated prior to use, such as preparing plasma from blood, diluting viscous fluids, or the like; methods of treatment can involve extraction, filtration, distillation, concentration, inactivation of interfering components, and the addition of reagents. Such pretreatment also can include the modification of a solid material suspected of containing the analyte to form a liquid medium or to release the analyte.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) for example, but not limited to, the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte includes any antigenic substances such as but not limited to a protein, a peptide, an amino acid, a nucleotide target, and the like, haptens, antibodies, macromolecules and combinations thereof.

"Analyte-analog" refers to a substance which cross-reacts with the analyte-specific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole molecule analyte so that the analyte-analog can bind to the analyte-specific binding member.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include for example without limitation biotin and avidin, carbohydrates and lectins, complementary nucleotide sequences, effector and receptor molecules, cofactors and enzymes, enzyme inhibitors and enzymes, and the like. In addition, other specific binding pairs include, as examples without limitation, complementary peptide sequences, a peptide sequence and an antibody specific for the sequence or the entire protein, polymeric acids and bases, dyes and protein binders, peptides and specific protein binders (for example, ribonuclease, S-peptide and ribonuclease S-protein). Furthermore, specific binding pairs can include members that are analogs of the original specific binding members, for example, an analyte-analog. The specific binding pair member can include a protein, a peptide, an amino acid, a nucleotide target, and the like. Immunoreactive specific binding members include antigens, antigen fragments, antibodies and antibody fragments, both monoclonal and polyclonal, and complexes thereof, including those formed by recombinant DNA molecules, folate-binding protein to determine folic acid, or the use of a lectin as a member of a specific binding pair for the determination of a carbohydrate.

The term "hapten", as used herein, refers to a partial antigen or non-protein binding member which is capable of binding to an antibody, but which is not capable of eliciting antibody formation unless coupled to a carrier protein.

The "indicator reagent" which also is referred to as a "labeled reagent" comprises a "signal generating compound" ("label") which is capable of generating and generates a measurable signal detectable by external means conjugated (attached) to a specific binding member for HIV. In addition to being an antibody member of a specific binding pair for HIV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HIV as in a sandwich assay, to the capture reagent as in a competitive assay, or to the ancillary specific binding member as in an indirect assay. The attachment of the signal generating compound and the specific binding member may be by covalent or non-covalent binding, but the method of attachment is not critical to the present invention. The label allows the indicator reagent to produce a detectable signal that is directly or indirectly related to the amount of analyte in the test sample. The specific binding pair member component of the indicator reagent is selected to directly bind to the analyte or to indirectly bind to the analyte by means of an ancillary specific binding member. The labeled reagent can be incorporated in the test device, it can be combined with the test sample to form a test solution, it can be added to the device separately from the test sample or it can be predeposited or reversibly immobilized at the capture site. In addition, the binding member may be labeled before or during the performance of the assay by means of a suitable attachment method.

The various "signal generating compounds" ("labels") contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. Examples of direct visual labels include colloidal metallic particles such as gold, colloidal non-metallic particles such as selenium, dyed or colored particles such as a dyed plastic or a stained microorganism, colored or colorable organic polymer latex particles, Duracytes® (derivatized red blood cells, available from Abbott Laboratories, Abbott Park, Ill.), liposomes or other vesicles containing directly visible substances, and the like. The selection of a particular label is not critical. The label will be capable of producing a signal either by itself (such as a visually detectable colored organix polymer latex particle) or instrumentally detectable (such as a luminescent compound or radiolabeled element) or detectable in conjunction with one or more additional substances such as an enzyme/substrate signal producing system. A variety of different labeled reagents can be formed by varying either the label or the specific binding member component of the labeled reagent; it will be appreciated by one skilled in the art that the choice involves consideration of the analyte to be detected with the desired means of detection.

When using a visually detectable particle as the label, such as selenium, dyed particles or black latex, the labeled reagent binding member(s) may be attached to the particles. Alternatively, the binding member(s) may be attached to separate batches of particles and afterwards the particles mixed.

"Signal producing component" refers to any substance capable of reacting with another assay reagent or with the analyte to produce a reaction product or signal that indicates the presence of the analyte and/or serves to indicate that certain assay characteristics have been satisfied. The signal producing component is detectable by visual or instrumental means. "Signal production system" as used herein refers to the group of assay reagents that are needed to produce the desired reaction product or signal. Thus, one or more signal producing components can be reacted with the label to generate a detectable signal. For example, when the label is an enzyme, amplification of the detectable signal is obtained by reacting the enzyme with one or more substrates or additional enzymes and substrates to produce a detectable reaction product.

In a preferred embodiment of the present invention, a visually detectable label is used as the label component of the labeled reagent, thereby providing for the direct visual or instrumental readout of the presence or amount of the analyte in the test sample without the need for additional signal producing components at the detection sites. Suitable materials for use include colloidal metals such as gold and dye particles as well as non-metallic colloids such as colloidal selenium, tellurium and sulfur particles.

"Immobilized capture reagent" refers to one or more specific binding members that are attached within or upon a portion of the solid phase support or chromatographic strip to form one or more "capture sites" wherein the analyte, positive control reagent, and/or labeled reagent become immobilized on the strip or wherein the immobilized reagent slows the migration of the analyte and/or labeled reagent through the strip. The method of attachment is not critical to the present invention. The immobilized capture reagent facilitates the observation of the detectable signal by substantially separating the analyte and/or the labeled reagent from unbound assay reagents and the remaining components of the test sample. In addition, the immobilized reagent may be immobilized on the solid phase before or during the performance of the assay by means of any suitable attachment method.

Typically, a capture site of the present invention is a delimited or defined portion of the solid phase support such that the specific binding reaction between the immobilized capture reagent and analyte. This facilitates the detection of label that is immobilized at the capture site or sites in contrast to other portions of the solid phase support. The delimited site is typically less than 50% of the solid phase support, and preferably less than 10% of the solid phase support. The immobilized reagent can be applied to the solid phase material by dipping, inscribing with a pen, dispensing through a capillary tube or through the use of reagent jet-printing or biodotting or any other suitable dispensing techniques. In addition, the capture site can be marked, for example with a dye, such that the position of the capture site upon the solid phase material can be visually or instrumentally determined even when there is no label immobilized at the site. Preferably, the immobilized reagent is positioned on the strip such that the capture site is not directly contacted with the test sample, that is, the test sample must migrate by capillary action through at least a portion of the strip before contacting the immobilized reagent.

The immobilized capture reagent may be provided in a single capture or detection site or in multiple sites on or in the solid phase material. The preferred embodiment of the invention provides for immobilized patient capture reagent (s) and an immobilized procedural capture reagent. The immobilized capture reagents may also be provided in a variety of configurations to produce different detection or measurement formats. For example, the immobilized capture reagent may be configured as a letter, number, icon or symbol or any combination thereof. When configured as a letter, the immobilized capture reagent may be either a single letter or combination of letters that form words or abbreviated words such as "POS", "NEG" or "OK". Alternatively, the immobilized capture reagent may be configured as a symbol or combination of symbols, such as for example, a plus, minus, check-mark, bar, diamond, triangle, rectangle, circle, oval, square, arrow, line or any combination thereof. The immobilized capture reagent can be provided as a discreet capture site or "band" of reagent on or in the solid phase material. Alternatively, the immobilized reagent can be distributed over a large portion of the solid phase material in a substantially uniform manner to form the capture site. The extent of signal production in the patient capture site is related to the amount of analyte in the test sample. When using a positive control, the extent of signal production in a positive control capture site, if desired, is related to the amount of positive control reagent applied to the strip.

"Negative binding reagent" which may be used interchangeably with the terms "negative control" or "negative control reagent" refers to any substance which is used to determine the presence of non-specific binding or aggregation of any labeled reagent. The negative control reagent may be, for example, a substance comprising specific binding members such as antigens, antibodies or antibody fragments. Additionally, the negative control reagent may be derived from the same or a different species as the other reagents on the teststrip or from a combination of two or more species. The presence of a detectable signal from the negative control reagent on the teststrip indicates an invalid test.

"Ancillary specific binding member" refers to any member of a specific binding pair which is used in the assay in addition to the specific binding members of the indicator reagent or immobilized capture reagent. One or more ancillary specific binding members can be used in an assay. For example, an ancillary specific binding member can be capable of binding the indicator reagent to the analyte of interest, in instances where the analyte itself could not directly attach to the indicator reagent. Alternatively, an ancillary specific binding member can be capable of binding the immobilized capture reagent to the analyte of interest, in instances where the analyte itself could not directly attach to the immobilized capture reagent. The ancillary specific binding member can be incorporated into the assay device or it can be added to the device as a separate reagent solution.

The "solid phase support" or "chromatographic material" or "strip" refers to any suitable porous, absorbent, bibulous, isotropic or capillary material, which includes the reaction site of the device and through which the analyte or test sample can be transported by a capillary or wicking action. It will be appreciated that the strip can be made of a single material or more than one material (e.g., different zones, portions, layers, areas or sites can be made of different materials) so long as the multiple materials are in fluid-flow contact with one another thereby enabling the passage of test sample between the materials. Fluid-flow contact permits the passage of at least some components of the test sample, e.g., analyte, between the zones of the porous material and is preferably uniform along the contact interface between the different zones.

Thus, natural, synthetic or naturally occurring materials that are synthetically modified can be used as the solid-phase support and include, but are not limited to: papers (fibrous) or membranes (microporous) of cellulose materials such as paper, cellulose, and cellulose derivatives such as cellulose acetate and nitrocellulose; fiberglass; cloth, both naturally occurring (e.g., cotton) and synthetic (e.g., nylon); porous gels; and the like. The porous material should not interfere with the production of a detectable signal. The chromatographic material may have an inherent strength, or strength can be provided by means of a supplemental support.

The particular dimensions of the strip material is a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the chromatographic material.

When appropriate, it is necessary to select strip dimensions that allow the combination of multiple strips in a single assay device. It also is within the scope of this invention to have a reagent, at the distal end of the chromatographic material, which indicates the completion of a binding assay (i.e., end of assay indicator) by hanging color upon contact with the test solution, wicking solution or a signal producing component. Reagents which would change color upon contact with a test solution containing water are the dehydrated transition metal salts such as $CuSO_4$, $Co(NO_3)_2$, and the like. pH indicator dyes also can be selected to respond to the pH of the buffered wicking solution. For example, phenolphthalein changes from clear (i.e., colorless) to intense pink upon contact with a wicking solution having a pH range between 8.0–10.0.

Capture reagents may be located anywhere along the teststrip in single or multiple pathways with the proviso that they be located in the fluid flow path of their respective labeled reagents. It is understood by those skilled in the art that as fluid migrates through the strip there is little cross flow of fluid. Thus, all mobile reagents coming into contact with the fluid also migrate in the direction of the fluid flow, i.e. there is no substantial migration of reagents transversely across the strip.

The present invention further provides kits for carrying out binding assays. For example, a kit according to the present invention can comprise a teststrip such as the teststrip depicted in FIG. 12, or alternatively can comprise the comb-type or card-type device with its incorporated reagents as well as a transport solution and/or test sample pretreatment reagent as described above. Other assay components known to those skilled in the art include buffers, stabilizers, detergents, bacteria inhibiting agents and the like which can also be present in the assay device or separate reagent solution.

The present invention optionally includes a non-reactive cover (also referred to as an enclosure or casing) around the device. Preferably, the cover encloses at least the strip to avoid contact with and contamination of the capture sites. The cover also may include a raised area adjacent to the application pad to facilitate receiving and/or containing a certain volume of the test sample and/or wicking solution. Additionally, the cover may include a cut out area or areas in the form of a letter, number, icon, or symbol or any combination thereof. In this embodiment, the cut out area or areas form the design for particular capture site or sites once the strip is completely enclosed. It is preferred that a sufficient portion of the strip be encased to prevent applied test sample from contacting the capture sites without first passing through a portion of the strip.

Another device component is a test sample application pad, which may be an optional feature. The application pad is in fluid flow contact with one end of the strip material, referred to as the proximal end, such that the test sample can pass or migrate from the application pad to the strip. Fluid flow contact can include physical contact of the application pad to the chromatographic material, as well as the separation of the pad from the strip by an intervening space or additional material which still allows fluid to pass between the pad and the strip. Substantially all of the application pad can overlap the chromatographic material to enable the test sample to pass through substantially any part of the application pad to the proximal end of the strip. Alternatively, only a portion of the application pad might be in fluid flow contact with the chromatographic material. The application pad can be any material which can transfer the test sample to the chromatographic material and which can absorb a volume of test sample that is equal to or greater than the total volume capacity of the chromatographic material.

Materials preferred for use in the application pad include nitrocellulose, porous polyethylene frit or pads and glass fiber filter paper. The material also must be chosen for its compatibility with the analyte and assay reagents.

In addition, the application pad typically contains one or more assay reagents either diffusively or non-diffusively attached thereto. Reagents which can be contained in the application pad include, but are not limited to, labeled reagents, ancillary specific binding members, and signal producing system components needed to produce a detectable signal. For example, in a binding assay it is preferred that the labeled reagent be contained in the application pad. The labeled reagent is released from the pad to the strip with the application of the test sample, thereby eliminating the need to combine the test sample and labeled reagent prior to using the device. The isolation of assay reagents in the application pad also keeps separate the interactive reagents and facilitates the manufacturing process.

In some instances, the application pad also serves the function of an initial mixing site and a reaction site for the test sample and reagent. In preferred embodiments, the application pad material is selected to absorb the test sample at a rate that is faster than that achieved by the strip material alone. Typically, the pad material is selected to absorb fluids two to five times faster than the strip material. Preferably, the pad will absorb fluids four to five times faster than will the strip material.

In an optional embodiment of the present invention, gelatin is used to encompass all or part of the application pad. Typically, such encapsulation is produced by overcoating the application pad with fish gelatin. The effect of this overcoating is to increase the stability of the reagent contained by the application pad. The application of test sample to the overcoated application pad causes the gelatin to dissolve and thereby enables the dissolution of the reagent. In another embodiment of the present invention, the reagent containing application pad is dried or lyophilized to increase the shelf-life of the device. Lyophilized application pads have been found to produce stronger signals than air-dried application pads, and the lyophilized application pads have been found to maintain stability for longer periods of time. The reagents contained in the application pad are rehydrated with the addition of test sample to the pad.

The present invention also can be modified by the addition of a filtration means. The filtration means can be a separate material placed above the application pad or between the application pad and the strip material, or the material of the application pad itself can be chosen for its filtration capabilities. The filtration means can include any filter or trapping device used to remove particles above a certain size from the test sample. For example, the filter means can be used to remove red blood cells from a sample of whole blood, such that plasma is the fluid received by the application pad and transferred to the chromatographic material.

Yet another modification of the present invention involves the use of an additional layer or layers of porous material placed between the application pad and the chromatographic material or overlaying the application pad. Such an additional pad or layer can serve as a means to control the rate of flow of the test sample from the application pad to the strip. Such flow regulation is preferred when an extended incubation period is desired for the reaction of the test sample and the reagent(s) in the application pad. Alternatively, such a layer can contain additional assay reagent(s) that preferably is isolated from the application pad reagent(s) until the test sample is added, or it can serve to prevent unreacted assay reagents from passing to the chromatographic material.

When small quantities of non-aqueous or viscous test samples are applied to the application pad, it may be necessary to employ a wicking or transport solution, preferably a buffered solution, to carry the reagent(s) and test sample from the application pad and through the strip. When an aqueous test sample is used, a transport solution generally is not necessary but can be used to improve flow characteristics through the device or to adjust the pH of the test sample. The transport solution typically has a pH range from about 5.5 to about 10.5, and more preferably from about 6.5 to about 9.5. The pH is selected to maintain a significant level of binding affinity between the specific binding members in a binding assay. When the label component of the indicator reagent is an enzyme, however, the pH also must be selected to maintain significant enzyme activity for color development in enzymatic signal production systems. Illustrative buffers include phosphate, carbonate, barbital, diethylamine, tris(hydromethyl)aminomethane (Tris), Bis-Tris, 2-amino-2-methyl-1-propanol and the like. The transport solution and the test sample can be combined prior to contacting the application pad or they can be contacted to the application pad sequentially.

Predetermined amounts of signal producing components and ancillary reagents can be incorporated within the device, thereby avoiding the need for additional protocol steps or reagent additions. Thus, it also is within the scope of this invention to provide more than one reagent to be immobilized within the application pad and/or the strip material.

This invention provides assay devices and methods, where the devices use strips of chromatographic material capable of transporting liquids for the performance of an assay on a patient sample or the performance of a multiple assay on a patient sample. The device may include test sample application pads in fluid flow contact with the strip which function to regulate the flow of test sample to the chromatographic material, to filter the test samples and to deliver and/or mix assay reagents. Assay reagents may be incorporated within the application pad as well as in the chromatographic material. By varying the configuration of reagent-containing sites on the device, qualitative and quantitative displays of assay results can be obtained. Preferably, the reagents are situated in the devices in such a way as to make the assay substantially self-performing and to facilitate the detection and quantitation of the assay results. One or more detectable signals resulting from the reactions at the reagent-containing sites and/or the binding assay then can be detected by instrumentation or direct visual observation.

The present invention provides an assay for simultaneously detecting and differentiating antibodies to HIV-1 group M, HIV-1 group O and HIV-2 in a test sample, and an analytical device with which to perform this simultaneous detection and differentiation. In a sandwich assay format, the test sample suspected of containing the analyte (for example, antibody to HIV-1 group M) is contacted with a predetermined amount of indicator reagent (in this example, labeled anti-species antibody [Ab*]) to form a reaction mixture containing an analyte/indicator reagent complex (Ab–Ab*). The indicator reagent (Ab*) may be separate from or preferably incorporated within the test device. The resulting reaction mixture then migrates through the teststrip. The reaction mixture contacts capture reagent sites (one for HIV-1 group M, one for HIV-1 group O, and one for HIV-2) containing separately immobilized analyte specific binding member ([l-Ag]) that binds at a site on the analyte distinct from the indicator reagent. The capture reagent therefore is capable of binding to the Ab–Ab* complex to form an immobilized l-Ab-Ag-Ab* complex that is detectable at the capture reagent site. Furthermore, the reaction mixture also may migrate further through the teststrip and react with reagent present in the end of assay indicator site.

Referring to FIG. 13, the test device (18) for the assay comprises a nitrocellulose membrane strip (24) upon which are placed and allowed to dry in separate distinct capture areas, selected specific and highly purified recombinant antigens derived from the HIV-1 group M (26), HIV-1 group O (28) and HIV-2 gp41 (30) region of each. The test device (18) further comprises a conjugate pad (32) which comprises a glass fiber filter (34) presenting a selenium colloid sensitized with an anti-species antibody (e.g., goat anti-human IgG) suspended in a fluid containing nitrocellulose blocking proteins which has been dried before assembly and affixed to the distal end (20) of the nitrocellulose membrane (24). The entire device (18) is held permanently in place by a top clear laminating material (36) which bears an adhesive surface (38) in contact with the top surface of the nitrocellulose membrane (24) and attached to the conjugate pad (20), and a bottom laminating material (48) which bears an adhesive surface (38) in contact with the bottom surface (48) of the nitrocellulose membrane (24). The test fluid flows from the distal end (20) to the proximal end (22) and contacts each of the three separate distinct capture areas. The device also can have a test sample pad and reactivity zone (40) upon which anti-species (i.e., anti-human) conjugate is placed. The device also preferably has a blotter (44) to absorb any remaining fluid in the device and has a site for indicating completion of the assay (46). The read out (in the capture areas and/or in the test sample reactivity zone) can be either visual direct readout without the aid of laboratory equipment or automated by an instrument. Furthermore, the test device can be enclosed in a casing (42) of molded plastic or other suitable material.

The assay is performed as follows. Test sample such as human serum, preferably previously diluted in buffer (elution buffer, consisting of 50 mM TRIS (pH 8.4), 1% w/v solid bovine serum albumin [BSA], 0.4% v/v Triton X-405®, 1.5% w/v casein, 3% w/v bovine IgG, 4% w/v $E.$ $coli$ lysate, pH 8.2; dilution at 1 $\mu$l serum to 100 $\mu$l of elution buffer), is contacted with the anti-IgG colloid conjugate at the distal end (20) of the test device. IgG in the test sample is bound by the anti-IgG colloid, and the complexes are chromatographed along the length of the absorbant pad (preferably, nitrocellulose membrane). As the complexes flow, they pass over the discrete zones (FIG. 13, sites 30, 26, and 28) in which the HIV recombinant antigens previously have been applied. If the complexes contain specific antibody to the recombinant antigens in any of the discrete zones, a reaction takes place and red zones of color appear in the appropriate zone(s). Multiple specificities can be determined simultaneously. In addition, a positive control, consisting of a pooled test sample positive for all three antigens tested, should react positively in all three zones. Alternatively, a positive control sample, reactive with each of the antigens in the test, can be run separately for each analyte for which antibody is being assayed.

It is contemplated and within the scope of the present invention that antibody analytes to HIV-1 group M, HIV-1 group O, and HIV-2, may be detectable in these assays by use of a synthetic, recombinant or purified polypeptide comprising the entire or partial polypeptide (amino acid) sequences described herein, as the capture reagent. "Purified protein" (or "purified polypeptide") means a polypeptide of interest or fragment thereof which is essentially free, that is, contains less than about 50%, preferably less than about 70%, and more preferably, less than about 90%, of cellular components with which the polypeptide of interest is naturally associated. Methods for purifying are known in the art. A "recombinant polypeptide" or "recombinant protein" or "polypeptide produced by recombinant techniques," which are used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system. Further, the term "synthetic peptide" as used herein means a polymeric form of amino acids of any length, which may be chemically synthesized by methods well-known to the routineer. These synthetic peptides are useful in various applications.

The preferred capture reagent for HIV-1 group O comprises a polypeptide sequence selected from the group consisting of SEQ ID NO: 48, SEQ ID NO: 50, SEQ ID NO: 52, and SEQ ID NO: 54, SEQ ID NO: 58, and SEQ ID NO: 60, the capture reagent for HIV-1 group M comprises SEQ ID NO: 56, and the capture reagent for HIV-2 comprises SEQ ID NO: 55. It is preferred that these polypeptides be produced by recombinant technology.

The present invention will now be described by way of examples, which are meant to illustrate, but not to limit, the spirit and scope of the invention.

EXAMPLES

Example 1

Cloning

Oligonucleotides for gene construction and sequencing were synthesized at Abbott Laboratories, Synthetic Genetics (San Diego, Calif.) or Oligo Etc. (Wilsonville, Calif.). All polymerase chain reaction (PCR) reagents, including AmpliTaq DNA polymerase and UlTma DNA polymerase, were purchased from Perkin-Elmer Corporation (Foster City, Calif.) and used according to the manufacturer's specifications unless otherwise indicated. PCR amplifications were performed on a GeneAmp 9600 thermal cycler (Perkin-Elmer). Unless indicated otherwise, restriction enzymes were purchased from New England BioLabs (Beverly, Mass.) and digests were performed as recommended by the manufacturer. DNA fragments used for cloning were isolated on agarose (Life Technologies, Gaithersburg, Md.) gels, unless otherwise indicated.

Desired fragments were excised and the DNA was extracted with a QIAEX II gel extraction kit or the QIAquick gel extraction kit (Qiagen Inc., Chatsworth, Calif.) as recommended by the manufacturer. DNA was resuspended in $H_2O$ or TE [1 mM ethylenediaminetetraacetic acid (EDTA; pH 8.0; BRL Life Technologies), 10 mM tris (hydroxymethyl)aminomethane-hydrochloride (Tris-HCl; pH 8.0; BRL Life Technologies)]. Ligations were performed using a Stratagene DNA ligation kit (Stratagene Cloning Systems, La Jolla, Calif.) as recommended by the manufacturer. Ligations were incubated at 16° C. overnight.

Bacterial transformations were performed using MAX EFFICIENCY DH5α competent cells (BRL Life Technologies) or Epicurian Coli XL1-Blue supercompetent cells (Stratagene Cloning Systems) following the manufacturer's protocols. Unless indicated otherwise, transformations and bacterial restreaks were plated on LB agar (Lennox) plates with 150 μg/ml ampicillin (M1090; MicroDiagnostics, Lombard, Ill.) or on LB agar+ampicillin plates supplemented with glucose to a final concentration of 20 mM, as noted. All bacterial incubations (plates and overnight cultures) were conducted overnight (~16 hours) at 37° C.

Screening of transformants to identify desired clones was accomplished by sequencing of miniprep DNA and/or by colony PCR. Miniprep DNA was prepared with a Qiagen Tip 20 Plasmid Prep Kit or a Qiagen QIAwell 8 Plasmid Prep Kit following the manufacturer's specifications, unless otherwise indicated. For colony PCR screening, individual colonies were picked from transformation plates and transferred into a well in a sterile flat-bottom 96-well plate (Costar, Cambridge, Mass.) containing 100 μl sterile $H_2O$. One-third of the volume was transferred to a second plate and stored at 4° C. The original 96-well plate was microwaved for 5 minutes to disrupt the cells. 1 μl volume then was transferred to a PCR tube as template. 9 μl of a PCR master mix containing 1 μl 10X PCR buffer, 1 μl 2 mM dNTPs, 1 μl (10 pmol) sense primer, 1 μl (10 pmol) anti-sense primer, 0.08 μl AmpliTaq DNA polymerase (0.4 units), and 4.2 μl $H_2O$ was added to the PCR tube. Reactions were generally amplified for 20–25 cycles of 94° C. for 30 seconds, 50–60° C. (depending on primer annealing temperatures) for 30 seconds and 72° C. for 60 seconds. Primers were dependent on the insert and cycle conditions were modified based on primer annealing temperatures and the length of the expected product. After cycling, approximately ⅓ of the reaction volume was loaded on an agarose gel for analysis. Colonies containing desired clones were propagated from the transfer plate.

Unless otherwise indicated, DNA sequencing was performed on an automated ABI Model 373 Stretch Sequencer (Perkin Elmer). Sequencing reactions were set up with reagents from a FS TACS Dye Term Ready Reaction Kit (Perkin Elmer) and 250–500 ng plasmid DNA according to the manufacturer's specifications. Reactions were processed on Centri-Sep columns (Princeton Separations, Adelphia, N.J.) prior to loading on the Sequencer. Sequence data was analyzed using Sequencher 3.0 (Gene Codes Corporation, Ann Arbor, Mich.) and GeneWorks 2.45 (Oxford Molecular Group, Inc., Campbell, Calif.).

Example 2

Determination of the Env Sequence of the HIV-1 Group O Isolate HAM112.

Viral RNA was extracted from culture supernatants of human peripheral blood mononuclear cells infected with the HIV-1 group O isolate designated HAM 112 (H. Hampl et al., supra) using a QIAamp Blood Kit (Qiagen) and the manufacturer's recommended procedure. RNA was eluted in a 50 μl volume of nuclease-free water (5Prime-3Prime, Inc., Boulder, Colo.) and stored at −70° C. The strategy for obtaining the env region sequence involved cDNA synthesis and PCR (nested) amplification of four overlapping env gene fragments. The amplified products were sequenced directly on an automated ABI Model 373 Stretch Sequencer. Amplification reactions were carried out with GeneAmp RNA PCR and GeneAmp PCR Kits (Perkin Elmer) as outlined by the manufacturer. Oligonucleotide primer positions correspond to the HIV-1 ANT70 env sequence (G. Myers et al., eds., supra). The primers env10R [nucleotide (nt) 791–772; SEQ ID NO: 62], env15R (nt 1592–1574; SEQ ID NO: 63), env22R (nt 2321–2302; SEQ ID NO: 64), env26R (nt 250–232 3' of env; SEQ ID NO: 65) were used for cDNA synthesis of fragments 1–4, respectively. Reverse transcription reactions were incubated at 42° C. for 30 minutes then at 99° C. for 5 minutes. First round PCR amplifications consisted of 30 cycles of 95° C. for 30 seconds, 52° C. for 30 seconds, and 72° C. for 1 minute using the primer combinations: env1F (nt 184–166 5' of env; SEQ ID NO: 66) and env10R (SEQ ID NO: 62), env7F (nt 564–586; SEQ ID NO: 67) and env15R (SEQ ID NO: 63), env12F (nt 1289–1308; SEQ ID NO: 68) and env22R (SEQ ID NO: 64), env19F (nt 2020–2040; SEQ ID NO: 69) and env26R (SEQ ID NO: 65) for fragments 1 through 4, respectively. For the second round of amplification (nested PCR), 5 μl of the respective first round PCR reactions was used as template along with the primer combinations env2F (nt 37–15 5' of env; SEQ ID NO: 70) and env9R (nt 740–721; SEQ ID NO: 71), env8F (nt 631–650; SEQ ID NO: 72) and env14R (nt 1437–1416; SEQ ID NO: 73), env13F (nt 1333–1354; SEQ ID NO: 74) and env21R (nt 2282–2265; SEQ ID NO: 75), env20F (nt 2122–2141; SEQ ID NO: 76) and env25R (nt 111–94 3' of env; SEQ ID NO: 77) for fragments 1 through 4, respectively. Second round amplification conditions were identical to those used for the first round. Fragments were agarose gel-purified and extracted with a Qiagen QIAEX II Gel Extraction Kit. Fragments were sequenced directly with the primers used for nested PCR along with primers env4F (SEQ ID NO: 78) and env5R (SEQ ID NO: 79) for fragment 1; primers env10F (SEQ ID NO: 80), env12F (SEQ ID NO: 81), env11R (SEQ ID NO: 82), env12F (SEQ ID NO: 68), and AG1 (SEQ ID NO: 87) for fragment 2; primers env15F (SEQ ID NO: 83) and env19R (SEQ ID NO: 84) for fragment 3; primers env22F (SEQ ID NO: 85) and env24R (SEQ ID NO: 86) for fragment 4. The deduced amino acid sequence of env from the HIV-2 group O isolate HAM112 (SEQ ID NO: 61) is presented in FIG. 1.

Example 3

Construction of Synthetic HIV-1 Group O env gp120/gp41 Genes

FIG. 2 depicts the strategy used to generate synthetic HIV-1 group O env gp120/gp41 gene constructs. The env gp120/gp41 sequences were based on the HIV-1 group O isolate HAM112 (SEQ ID NO: 61) (H. Hampl et al.). Determination of the env sequence of HAM112 is outlined in Example 2, hereinabove. Oligonucleotides were designed that encode the C-terminal 45 amino acids of the env gp120 and 327 amino acids of env gp41 (nucleotide #1 is the first base of the first codon of gp120 in the synthetic gene). The synthetic gene has a 26 amino acid deletion (nucleotides 643 through 720), relative to the native HAM112 gp41, that encompasses a highly hydrophobic (H) region (transmembrane region) of gp41. Thus, the full-length synthetic gp41 gene constructed is 327 amino acids.

In the synthetic oligonucleotides, the native HIV-1 codons were altered to conform to *E. coli* codon bias in an effort to increase expression levels of the recombinant protein in *E. coli*. See, for example, M. Gouy and C. Gautier, *Nucleic Acids Research* 10:7055 (1982); H. Grosjean and W. Fiers, *Gene* 18:199 (1982); J. Watson et al. (eds.), *Molecular Biology of the Gene,* 4th Ed., Benjamin Kumming Publishing Co., pp.440 (1987). The gene construction strategy involved synthesis of a series of overlapping oligonucleotides with complementary ends (Osyn-A through Osyn-L, depicted as A through L). When annealed, the ends served as primers for the extension of the complementary strand.

The fragments then were amplified by PCR. This process ("PCR knitting" of oligonucleotides) was reiterated to progressively enlarge the gene fragment. Oligonucleotide Osyn-5' was designed for cloning into the pL vector pKRR826. The expression vector, pKRR826, is a modified form of the lambda pL promoter vector pSDKR816, described in U.S. Ser. No. 08/314,570, incorporated herein by reference. pKRR826 is a high copy number derivative of pBR322 that contains the temperature sensitive cI repressor gene (Benard et al., *Gene* 5:59 [1979]). However, pKRR826 lacks the translational terminator rrnBt1 and has the lambda pL and lambda pR promoters in the reverse orientation, relative to pSDKR816. The polylinker region of pKRR826 contains Eco RI and Bam HI restriction enzyme sites and lacks an ATG start codon. Optimal expression is obtained when the 5' end of the gene insert (including an N-terminal methionine) is cloned into the EcoRI site.

Osyn-5' was designed to contain an Eco RI restriction site for cloning and an ATG codon (methionine) to provide for proper translational initiation of the recombinant proteins. The anti-sense oligonucleotides Osyn-O3'(SEQ ID NO: 15), Osyn-P3' (SEQ ID NO: 16), and Osyn-M (M) (SEQ ID NO: 14) each contain two sequential translational termination codons (TAA,TAG) and a Bam HI restriction site. When outside primers Osyn-5' (SEQ ID NO: 11) and Osyn-M (M) (SEQ ID NO: 14) were used, a full-length gp41 (327 amino acids) gene was synthesized (pGO-11PL; SEQ ID NO: 52). Outside oligonucleotides Osyn-5' (SEQ ID NO: 11) and OsynO3' (SEQ ID NO: 15) resulted in a truncated gp41 product of 199 amino acids (pGO-9PL; SEQ ID NO: 48). Alternatively, outside oligonucleotides Osyn-5' (SEQ ID NO: 11) and Osyn-P3' (SEQ ID NO: 16) resulted in a truncated gp41 product 169 amino acids in length (pGO-8PL; SEQ ID NO: 58).

The synthetic genes also were expressed as CMP-KDO synthetase (CKS) fusion proteins. PCR-mediated transfer of the synthetic genes from pKRR826 into pJO200 (described in U.S. Ser. No. 572,822, and incorporated herein by reference) was accomplished with an alternative outside sense oligonucleotide PCR primer (5' end), Osyn-5'CKS (SEQ ID NO: 25). Osyn-5'CKS contained an Eco RI restriction site and resulted in the in-frame fusion of the synthetic gene insert to CKS in the expression vector pJO200. The 3' outside primers (antisense) Osyn-M (SEQ ID NO: 14), Osyn-)3' (SEQ ID NO: 15) and Osyn-P3' (SEQ ID NO: 16) were used in combination with Osyn-5'CKS (SEQ ID NO: 25) to generate pGO-11CKS (SEQ ID NO: 54), pGO-9CKS (SEQ ID NO: 50), and pGO-8CKS (SEQ ID NO: 60), respectively. These steps are detailed hereinbelow.

A. PCR Knitting of Synthetic Oligonucleotides

Three PCR reactions (100 μl volume) were set up as follows:

(1) Reaction 1B: AmpliTaq DNA polymerase (2.5U) and 1X buffer, along with 40 μM of each dNTP (dATP, dCTP, dGTP, and dTTP), 25 pmol each of oligonucleotides Osyn-A (SEQ ID NO: 3) and Osyn-D (SEQ ID NO: 5), and 0.25 pmol each of oligonucleotides Osyn-B (SEQ ID NO: 17) and Osyn-C (SEQ ID NO: 4);

(2) Reaction 2A: UlTma DNA Polymerase (3U) and 1X buffer along with 1.5 mM $MgCl_2$, 40 μM of each dNTP, 25 pmol each of oligonucleotides Osyn-E (SEQ ID NO: 6) and Osyn-H (SEQ ID NO: 9), and 0.25 pmol each of oligonucleotides Osyn-F (SEQ ID NO: 7) and Osyn-G (SEQ ID NO: 8); and (3) Reaction 3B: UlTma DNA Polymerase (3U) and 1X buffer along with 1.5 mM $MgCl_2$, 40 μM of each dNTP, 25 pmol each of oligonucleotides Osyn-I (SEQ ID NO: 10) and Osyn-L (SEQ ID NO: 13), and 0.25 pmol each of oligonucleotides Osyn-J (SEQ ID NO: 18) and Osyn-K (SEQ ID NO: 12).

Amplifications consisted of 20 cycles of 97° C. for 30 seconds, 52° C. for 30 seconds and 72° C. for 60 seconds. Reactions were then incubated at 72° C. for 7 minutes and held at 4° C. PCR-derived products 1B, 2A and 3B were gel isolated on a 1% agarose gel.

B. PCR Knitting of PCR Products From Reaction 1B and Reaction 2A.

A PCR reaction was set up with UlTma DNA Polymerase (3U) and 1X buffer along with 1.5 mM $MgCl_2$, 40 μM of each dNTP, 24.4 pmol of oligonucleotide Osyn-5' (SEQ ID NO: 11), 25 pmol of oligonucleotide Osyn-P3' (SEQ ID NO: 16), and ~10 ng each of gel-isolated 1B and 2A products from Example 3, Section 1A, hereinabove. Cycling conditions were the same as in Example 3, Section 1A. A second round of amplification was used to generate more of the desired product. This was performed by making an UlTma mix as described hereinabove (100 μl reaction volume) with 49 pmol Osyn-5' (SEQ ID NO: 11), 50 pmol Osyn-P3' (SEQ ID NO: 16) and 5 μl of the PCR product from the first round as template. These reactions were incubated at 94° C. for 90 seconds, and then used cycled as above (Section 3A). The Osyn-5'/Osyn-P3' PCR product was gel-isolated as described hereinabove.

C. Cloning of the Osyn-5'-Osyn-P3' PCR Product.

The Osyn-5'-Osyn-P3' PCR product was digested with the restriction endonucleases Eco RI+Bam HI and ligated into the vector pKRR826 (described hereinabove) that had been digested with Eco RI+Bam HI and gel-isolated. The ligation product was used to transform DH5α competent cells. The desired clone was identified by colony PCR using oligonucleotides pKRREcoRI Forward (SEQ ID NO: 38) and pKRRBamHI Reverse (SEQ ID NO: 39). Miniprep DNA was prepared from an overnight culture of pGO-8 candidate clone A2 and the Osyn-5'Osyn-P3' plasmid insert was sequenced with the oligonucleotide primers pKRREcoRI Forward (SEQ ID NO: 38), pKRRBamHI Reverse (SEQ ID NO: 39), 41sy-1(SEQ ID NO: 44), and 41sy-2(SEQ ID NO: 41).

D. Modification of pGO-8 Candidate Clone A2.

A 100 μl volume PCR reaction was set up with UlTma DNA Polymerase (3U) and 1X buffer, along with 1.5 mM MgCl$_2$, 40 μM of each dNTP, 50 pmol of oligonucleotides Osyn-5'-repair (SEQ ID NO: 24), 50 pmol Osyn-P3' (SEQ ID NO: 16), and ~1 ng of pGO-8 candidate clone miniprep DNA as template A2 (obtained from the reactions set forth hereinabove). The reaction was incubated at 94° C. for 90 seconds, and then amplified with 20 cycles of 94° C. for 30 seconds, 50° C. for 30 seconds and 72° C. for 60 seconds. The Osyn-5'-repair/Osyn-P3'PCR product then was gel isolated and digested with Eco RI+Bam HI. The digested product was ligated into Eco RI+Bam HI digested pKRR826 vector. The ligation product was used to transform DH5α competent cells. The desired clone was identified by colony PCR using oligonucleotides pKRREcoRI Forward (SEQ ID NO: 38) and pKRRBamHI Reverse (SEQ ID NO: 39). An overnight culture of pGO-8 candidate clone 6 was set up and a miniprep DNA was prepared. The Osyn5' repair/Osyn-P3' plasmid insert was sequenced with the oligonucleotide primers pKRREcoRI Forward (SEQ ID NO: 38), pKRRBamHI Reverse (SEQ ID NO: 39), 41sy-1(SEQ ID NO: 44), and 41sy-2(SEQ ID NO: 41). Based on the sequencing results, pGO-8 candidate clone #6 was designated pGO-8PL/DH5α. SEQ ID NO: 57 presents the nucleotide sequence of the coding region. FIG. 5 presents the amino acid sequence of the pGO-8PL recombinant protein (SEQ ID NO: 58). The pGO-8PL recombinant protein consists of a N-terminal methionine, 45 amino acids of env gp120 (HIV-1 group O, HAM112 isolate), and 169 amino acids of env gp41 (HIV-1 group O, HAM112 isolate).

E. Construction of pGO-8CKS/XL1.

pGO-8CKS/XL1 (SEQ ID NO: 59 presents the nucleotide sequence of the coding region) encodes the recombinant protein pGO-8CKS. FIG. 6 presents the amino acid sequence of pGO-8CKS (SEQ ID NO: 60). This protein consists of 246 amino acids of CKS/polylinker, 45 amino acids of env gp120 (HIV-1 group O, HAM112 isolate), and 169 amino acids of env gp41 (HIV-1 group O, HAM112 isolate). The construction of pGO-8CKS/XL1 was accomplished as follows.

A PCR reaction (100 μl volume) was set up with UlTma DNA Polymerase (3U) and 1X buffer along with 1.5 mM MgCl$_2$, 40 μM of each dNTP, 50 pmol of Osyn-5'CKS (SEQ ID NO: 25), 50 pmol Osyn-P3' (SEQ ID NO: 16), and 1 ng pGO-8PL clone #6 miniprep DNA. The reaction was incubated at 94° C. for 90 seconds then amplified with 25 cycles of 94° C. for 30 seconds; 55° C. for 30 seconds; 72° C. for 90 seconds. Then, the Osyn-5'CKS/Osyn-P3' PCR product was gel isolated. EcoR I+Bam HI digested the Osyn-5'CKS/Osyn-P3' PCR product and the vector pJO200. The digested pJO200 vector was gel isolated and ligated to digested Osyn-5'CKS/Osyn-P3' PCR product. XL1-Blue supercompetent cells were transformed with the ligation and plated on LB+ampicillin plates supplemented with 20 mM glucose. Colonies were restreaked for isolation on the same type of plates. An overnight culture of clone pGO-8CKS/XL1 was grown in LB broth+100 μg/ml carbenicillin (Sigma Chemical Co.)+20 mM glucose (Sigma Chemical Co.). Frozen stocks (0.5 ml overnight culture+0.5 ml glycerol) were made and DNA was prepared for sequence analysis. The following oligonucleotides were used as sequencing primers: CKS-1 (SEQ ID NO: 30), CKS-2(SEQ ID NO: 31), CKS-3(SEQ ID NO: 32), CKS-4(SEQ ID NO: 33), 43461 (SEQ ID NO: 2), 43285 (SEQ ID NO: 1), 41sy-1B (SEQ ID NO: 29), 41sy-2B (SEQ ID NO: 34), CKS176.1 (SEQ ID NO: 19), and CKS3583 (SEQ ID NO: 20).

F. Construction of pGO-9PL/DH5α.

FIGS. 3A through 3D and show a diagrammatic representation of the steps involved in construction of pGO-9PL/DH5α. pGO-9PL/ DH5α encodes the recombinant protein pGO-9PL. SEQ ID NO: 47 present the nucleotide sequence of the coding region of pGO-9PL/DH5α. FIG. 7 illustrates the amino acid sequence of the pGO-9PL recombinant protein (SEQ ID NO: 48). This protein consists of an N-terminal methionine, 45 amino acids of env gp120 (HIV-1 group O, HAM112 isolate), and 199 amino acids of env gp41 ( HIV-1 group O, HAM112 isolate). Construction of pGO-9PL/DH5α was accomplished as follows.

Step 1. A 100 μl PCR reaction was set up with UlTma DNA Polymerase (3U) and 1X buffer, along with 1.5 mM MgCl$_2$, 40 μM of each dNTP, 50 pmol of Osyn-5' (SEQ ID NO: 11), 50 pmol of Osyn-H (SEQ ID NO: 9), and ~2 ng of pGO-8 candidate clone 6 miniprep DNA (obtained from Example 3, Section D hereinabove) as template. The reaction was incubated at 94° C. for 120 seconds, and then amplified with 8 cycles of 94° C. for 30 seconds, 55° C. for 30 seconds and 72° C. for 60 seconds.

Step 2. A 100 μl PCR reaction was set up with UlTma DNA Polymerase (3U) and 1X buffer along with 1.5 mM MgCl$_2$, 40 μM of each dNTP, 50 pmol of Osyn-5' (SEQ ID NO: 11), 50 pmol Osyn-)3' (SEQ ID NO: 15), and 10 μl of the PCR reaction from step 1 as template. The reaction was incubated at 94° C. for 120 seconds then amplified with 18 cycles of 94° C. for 30 seconds, 55° C. for 30 seconds, 72° C. for 60 seconds, followed by incubation at 72° C. for 5 minutes.

The Osyn-5'/Osyn-O3' PCR product then was gel-isolated and digested with Eco RI+Bam HI. The digested product was ligated into Eco RI+Bam HI digested pKRR826 vector. The ligation product next was used to transform DH5α competent cells. An overnight culture of pGO-9PL candidate clone 3 was set up and a miniprep DNA was prepared. The Osyn-5'/Osyn-O3' plasmid insert was sequenced with the following oligonucleotides as primers: pKRREcoR1 Forward (SEQ ID NO: 38), pKRRBamHI Reverse (SEQ ID NO: 39), 41sy-1C (SEQ ID NO: 40), 41sy-2 (SEQ ID NO: 41), 41sy-3 (SEQ ID NO: 42) and 41sy-4 (SEQ ID NO: 23). pGO-9PL clone #3 then was restreaked for isolation. An isolated colony was picked, an overnight culture of it was grown, and a frozen stock (0.5 ml glycerol+0.5 ml overnight culture) was made. The stock was stored at −80° C. The sequence was confirmed using the primers indicated hereinabove, and this clone was designated as pGO-9PL/DH5α (SEQ ID NO: 47 presents the nucleotide sequence of the coding region, and SEQ ID NO: 48 presents the amino acid sequence of coding region). pGO-9PL/DH5α was restreaked, an overnight culture was grown, and a miniprep DNA was prepared (this prep was designated as H5).

G. Construction of pGO-9CKS/XL1.

FIG. 3A through 3D show a diagrammatic representation of the steps involved in construction of pGO-9CKS/XL1. pGO-9CKS/XL1 encodes the recombinant protein pGO-9CKS. FIG. 8 presents the amino sequence of the pGO-9CKS recombinant protein (SEQ ID NO: 50). This protein consists of 246 amino acids of CKS and polylinker followed by 45 amino acids of env gp120 (HIV-1 group O, HAM112 isolate), and 199 amino acids of env gp41 (HIV-1 group O, HAM112 isolate). The construction of pGO-9CKS/XL1 was accomplished as follows.

Two PCR reactions (100 μl volume) were set up with UlTma DNA Polymerase (3U) and 1X buffer, along with 1.5 mM MgCl$_2$, 40 μM of each dNTP, 50 pmol of Osyn-5'CKS (SEQ ID NO: 25), 50 pmol Osyn-O3' (SEQ ID NO: 15) and 1 ng pGO-9PL candidate clone 3 miniprep DNA (obtained from Example 3, Section F, hereinabove). Each reaction was incubated at 94° C. for 120 seconds, then amplified with 24 cycles of 94° C. for 30 seconds, 55° C. for 30 seconds, 72° C. for 120 seconds, followed by incubation at 72° C. for 5 minutes. The Osyn-5'CKS/OsynO3' PCR product then was gel isolated. The Osyn-5'CKS/Osyn-O3' PCR product and the vector pJO200 was digested with Eco RI+Bam HI. The digested pJO200 vector was gel isolated and ligated to the digested Osyn-5'CKS/Osyn-O3' PCR product. XL1-Blue supercompetent cells were transformed with the ligation and plated on LB+ampicillin plates supplemented with 20 mM glucose. Colonies were restreaked for isolation on the same type of plates. An overnight culture of clone pGO-9CKS candidate clone 4 was grown in LB broth+100 mg/ml carbenicillin (Sigma Chemical Co.)+20 mM glucose (Sigma Chemical Co.). Made frozen stocks (0.5 ml overnight culture+0.5 ml glycerol) and prepared DNA for sequence analysis. The following oligonucleotides were used as sequencing primers: CKS-1 (SEQ ID NO: 30), CKS-2 (SEQ ID NO: 31), CKS-3 (SEQ ID NO: 32), CKS-4 (SEQ ID NO: 33), 43461 (SEQ ID NO: 2), 43285 (SEQ ID NO: 1), 41sy-1B (SEQ ID NO: 29), 41sy-2B (SEQ ID NO: 34), 41sy-3B (SEQ ID NO: 35), CKS 176.1 (SEQ ID NO: 19), CKS3583 (SEQ ID NO: 20), and pTB-S8 (SEQ ID NO: 28). Clone pGO-9CKS candidate clone 4 was designated as pGO-9CKS/XL1 (SEQ ID NO: 49 presents the nucleotide sequence of coding region, and SEQ ID NO: 50 presents the amino acid sequence of coding region).

H. Construction of Osyn I—M Fragment.

The Osyn—O—M fragment was constructed as follows. A 100 μl PCR reaction was set up using AmpliTaq DNA Polymerase (2.5U), 1X buffer, 50 μM of each dNTP, 50 pmol I-PCR (SEQ ID NO: 26), 50 pmol Osyn-M (SEQ ID NO: 14) and 10 ng of gel-isolated PCR fragment 3A (Example 3, section A, hereinabove). The reaction was incubated at 95° C. for 105 seconds, and then it was amplified with 15 cycles of 95° C. for 30 seconds, 55° C. for 30 seconds, 72° C. for 60 seconds, and then it was held at 72° C. for 7 minutes. The product, designated as Osyn I—M, was gel-isolated and cloned into the PCR II vector (TA Cloning Kit; Invitrogen, San Diego, Calif.) following the manufacturer's recommended procedure. The resulting ligation product was used to transform DH5α competent cells. Plasmid miniprep DNA was generated from an overnight culture of clone IM-6, and the gene insert was sequenced with oligonucleotides 56759 (SEQ ID NO: 45) and 55848 (SEQ ID NO: 46).

I. Synthesis and Knitting of PCR Fragments I/6R and IM-6F.

These procedures were performed as follows.

Step 1. The following PCR reactions (100 μl volume) were set up: (a) I/6R with AmpliTaq DNA Polymerase (2.5U), 1X buffer, 50 μM of each dNTP, 50 pmol I-PCR (SEQ ID NO: 26), 50 pmol IM-6R (SEQ ID NO: 22) and 281 ng of clone IM-6 (obtained from Example 3, Section H) as template; (b) 6F/M with AmpliTaq DNA Polymerase (2.5U), 1X buffer, 50 μM of each dNTP, 50 pmol IM-6F (SEQ ID NO: 21), 50 pmol M-PCR (SEQ ID NO: 27) and 281 ng of clone IM-6 (obtained from Example 3, Section H) as template.

The reactions were incubated at 95° C. for 105 seconds, and then amplified with 20 cycles of 94° C. for 15 seconds, 60° C. for 30 seconds, 72° C. for 60 seconds, then incubated at 720° C. for 7 minutes. The PCR products I/6R and 6F/M next were gel isolated following the procedures as described hereinabove.

Step 2. A PCR reaction (100 μl volume) was set up with UlTma DNA Polymerase (3U) and 1X buffer along with 1.5 mM MgCl$_2$, 40 μM of each dNTP, 50 pmol of I-PCR (SEQ ID NO: 26), 50 pmol M-PCR (SEQ ID NO: 27), 50 ng I/6R, and ~20 ng 6F/M. The reaction was incubated at 95° C. for 105 seconds, and then it was amplified with 20 cycles of 94° C. for 15 seconds, 55° C. for 30 seconds, 72° C. for 60 seconds, followed by incubation at 72° C. for 7 minutes. The PCR product was processed on a Centri-sep column (Princeton Separations) following the manufacturer's instructions.

J. Construction of pGO-11PL/DH5α.

FIGS. 4A through 4F show a diagrammatic representation of the steps involved in construction of pGO-11PL/DH5α. pGO-11PL/DH5α encodes the recombinant protein pGO-11PL. FIG. 9 presents the amino acid sequence of the pGO-11PL recombinant protein (SEQ ID NO: 52). This protein consists of an N-terminal methionine, 45 amino acids of env gp120 (HIV-1 group O, HAM112 isolate), and 327 amino acids of env gp41 (HIV-1 group O, HAM112 isolate). pGO-11PL/DH5α was constructed as follows.

The final PCR product from Example 3, Section I and pGO-9PL vector (miniprep H5 from Example 3, section F) were digested sequentially with Age I and Bam HI. The digested pGO-9PL was then treated with calf intestinal alkaline phosphatase (BRL Life Technologies) for 15 minutes at 37° C., phenol/chloroform extracted, and precipitated with NaOAc and EtOH. The vector (pGO-9PL) was subsequently gel-isolated. The digested pGO-9PL and the digested PCR product were ligated, and the ligation product was used to transform DH5α competent cells. Colonies were restreaked for isolation. Clone pGO11-4 then was identified and restreaked for isolation. An overnight culture of pGO11-4 was prepared in order to generate frozen stocks and perform miniprep DNA for sequencing. Clone pGO11-4 was sequenced with the following oligonucleotide primers: pKRREcoR1 Forward (SEQ ID NO: 38), pKRRBamHI Reverse (SEQ ID NO: 39), 41sy-1C (SEQ ID NO: 40), 41sy-2 (SEQ ID NO: 41), 41sy-3 (SEQ ID NO: 42), 41sy-4 (SEQ ID NO: 23), 41sy-5B (SEQ ID NO: 43), 41sy-5C (SEQ ID NO: 36) and 41sy-6B (SEQ ID NO: 37). Based on the sequencing results, this clone was designated as pGO-11PL/DH5α (SEQ ID NO: 51 presents the nucleotide sequence of the coding region, and SEQ ID NO: 52 presents the amino acid sequence of coding region).

K. Construction of pGO-11CKS/XL1.

FIGS. 4A through 4G show a diagrammatic representation of the steps involved in construction of pGO-11CKS/XL1. pGO-11CKS/XL1 encodes the recombinant protein pGO-11CKS. FIG. 10 shows the amino sequence of the pGO-11CKS recombinant protein (SEQ ID NO: 54). This protein consists of 246 amino acids of CKS and polylinker followed by 45 amino acids of env gp120 (HIV-1 group O, HAM112 isolate), and 327 amino acids of env gp41 ( HIV-1 group O, HAM112 isolate). pGO-11CKS/XL1 was constructed as follows.

A PCR reaction (100 μl volume) was set up with UlTma DNA Polymerase (3U) and 1X buffer along with 1.5 mM MgCl$_2$, 40 μM of each dNTP, 50 pmol of Osyn-5'CKS (SEQ ID NO: 25), 50 pmol Osyn-M (SEQ ID NO: 14), and 1 ng pGO11-4 (obtained from Example 3, Section J) as template. The reaction was incubated at 94° C. for 105 seconds, and then amplified with 20 cycles of 94° C. for 30 seconds, 55° C. for 30 seconds, 72° C. for 120 seconds, followed by incubation at 72° C. for 7 minutes. The Osyn-5'CKS/Osyn-M PCR product was gel isolated. Next, the Osyn-5'CKS/Osyn-M PCR product and the vector pJO200 were EcoR I+Bam HI digested. The digested pJO200 vector was gel isolated. Overnight (16° C.) ligations were set up with the digested PCR product. XL1-Blue supercompetent cells were transformed with the ligation and plated on LB+ampicillin plates supplemented with 20 mM glucose. Colonies were restreaked for isolation on the same plates. An overnight culture (LB medium+100 μg/ml carbenicillin+ 20 mM glucose) of clone pGO-11CKS clone candidate 2 then was set up. Frozen stocks (0.5 ml 80% glycerol+0.5 ml overnight culture) were made as well as miniprep DNA for sequencing. The following oligonucleotides were used as primers for sequence analysis: CKS-1 (SEQ ID NO: 30), CKS-2 (SEQ ID NO: 31), CKS-3 (SEQ ID NO: 32), CKS-4 (SEQ ID NO: 33), 43461 (SEQ ID NO: 2), 43285 (SEQ ID NO: 1), 41sy-1B (SEQ ID NO: 29), 41sy-2B (SEQ ID NO: 34), 41sy-3B (SEQ ID NO: 35), 41sy-4 (SEQ ID NO: 23), 41sy-5C (SEQ ID NO: 36), 41sy-6B (SEQ ID NO: 37), CKS176.1 (SEQ ID NO: 19), CKS3583 (SEQ ID NO: 20), and pTB-S8 (SEQ ID NO: 28). pGO-11CKS clone #2 was designated as pGO-11CKS/XL1. SEQ ID NO: 53 presents the nucleotide sequence of the coding region of pGO-11CKS/XL1, and SEQ ID NO: 54 presents the amino acid sequence of the coding region of pGO-11CKS/XL1.

Example 4

Construction of pHIV210/XL1-Blue

FIG. 11 presents the amino acid sequence of the pHIV-210 recombinant protein (SEQ ID NO: 55). This protein consists of 247 amino acids of CKS/linker sequences, 60 amino acids from env gp120 (#432–491; HIV-2 isolate D194.10), and 159 amino acids of env gp36 (#492–650; HIV-2 isolate D194.10). The construction of pHIV210/XL1-Blue was accomplished as follows.

The genomic DNA of HIV-2 isolate D194.10 [H. Kuhnel et al., *Nucleic Acids Research* 18: 6142 (1990)] was cloned into the EMBL3 lambda cloning vector. See H. Kuhnel et al., *Proc. Nat'l. Acad. Sci. USA* 86: 2383–2387 (1989), and H. Kuhnel et al., *Nucleic Acids Research* 18: 6142 (1990), incorporated herein by reference. The lambda clone containing D194.10 (lambda A10) was received from Diagen Corporation, Dusseldorf, Germany. A PCR reaction (100 μl volume) was set up using AmpliTaq DNA polymerase (3.75 units), 200 μM each dATP, dCTP, dGTP, and dTTP, 0.5 μg primer 3634 (SEQ ID NO:88; annealing to positions 7437–7455 on the HIV-2 isolate D194.10 (EMBL accession #X52223), 0.5 μg primer 3636 (SEQ ID NO: 89, annealing to positions 8095–8077), 1X PCR buffer, and 5 μl of the lambda A10DNA diluted 1:50. The reaction was incubated 5 minutes at 94° C. then amplified with 35 cycles of 94° C. for 1 minute, 45° C. for 1 minute, 72° C. for 2 minutes; followed by an incubation at 72° C. for 5 minutes. The PCR reaction was extracted with phenol/chloroform (Boehringer Mannheim Corporation, Indianapolis, Ind.) and the DNA was ethanol (AAPER Alcohol & Chemical Company, Shelbyville, Ky.) precipitated. The DNA was digested with EcoRI+Bam HI and gel purified on an 1.5% agarose gel (SeaKem GTG agarose, FMC Corporation, Rockland, Me.). The purified product was ligated into EcoRI+Bam HI digested pJO200 vector using 800 units of T4 DNA ligase (New England BioLabs). XL1-Blue supercompetent cells (Stratagene) were transformed with 2 μl of the ligation as outlined by the manufacturer and plated on LB plates supplemented with ampicillin (Sigma Chemical Company). Overnight cultures were established by inoculating single colonies into Superbroth II media (GIBCO BRL, Grand Island, N.Y.) supplemented with 50 μg/ml ampicillin (Sigma) and 20 mM glucose (Sigma). Frozen stocks were established by adding 0.3 ml of 80% glycerol to 0.7 ml of overnight. After mixing stocks were stored at −70° C. Miniprep DNA was prepared from the overnight cultures using the alkaline lysis method followed by PEG precipitation. Sequence reactions were performed with a 7-deaza-dGTP Reagent Kit with Sequenase Version 2.0 (United States Biochemical Corporation, Cleveland, Ohio.) as outlined by the manufacturer. Reactions were run on 6% acrylamide gels (GIBCO BRL Gel-Mix 6) using the IBI gel apparatus as recommended by the manufacturer. Based on sequencing results, pHIV-210 clone #7 was designated as pHIV-210. The amino acid sequence of the pHIV-210 coding region is presented as SEQ ID NO: 55.

Example 5

Growth And Induction of *E. coli* Strains with HIV-1 Group O

Recombinant gp41 Antigen Construct

Overnight seed cultures of pGO-9CKS/XL1 were prepared in 500 ml sterile Excell Terrific Broth (available from Sigma Chemical Corp., St. Louis Mo.) supplemented with 100 μg/ml sodium ampicillin, and placed in a shaking orbital incubator at 32° C. or 37° C. One hundred milliliter (100 μl) inoculums from seed cultures were transferred to flasks containing 1 liter sterile Excell Terrific Broth supplemented with 100 μg/ml sodium ampicillin. Cultures were either (1) incubated at 37° C. until the culture(s) reached mid-logarithmic growth and then induced with 1 mM ITPG (isopropylthiogalactoside) for 3 hours at 37° C. Alternatively, the pL constructs were incubated at 32° C. until the culture(s) reached mid-logarithmic growth and then induced for 3 hours by shifting the temperature of the culture(s) to 42° C. After the induction period, cells were pelleted by centrifugation and harvested following standard procedures. Pelleted cells were stored at −70° C. until further processed.

Example 6

Isolation and solubilization of HIV-1 Group 0 Recombinant gp41

Antigen Produced as Insoluble Inclusion Bodies in *E. coli*

Frozen cells obtained from Example 5 were resuspended by homogenization in cold lysis buffer comprising 50 mM Tris pH 8, 10 mM Na EDTA, 150 mM NaCl, 8% (w/v) sucrose, 5% Triton X-100® (v/v), 1 mM PMSF and 1 μM pepstatin A. Lysozyme was added to the homogenates at a concentration of 1.3 mg per gram of cells processed, and the resultant mixture was incubated for 30 minutes on ice to lyse the cells. Inclusion bodies were separated from soluble proteins by centrifugation. These pelleted inclusion bodies were washed and pelleted sequentially in (1) Lysis Buffer; (2) 10 mM Na EDTA pH 8, 30% (w/v) sucrose; and (3) water. The washed inclusion bodies were resuspended in 50 mM Tris pH 8, 10 mM Na EDTA, 150 mM NaCl and 3 M urea, and incubated on ice for 1 hour. The inclusion bodies then were separated from the solubilized proteins by centrifugation. The pelleted inclusion bodies were fully solubilized in 7 M guanidine-HCl, 50 mM Tris pH 8, 0.1% (v/v) beta-mercaptoethanol (BME) overnight at 4° C. The solubilized recombinant antigens were clarified by centrifugation, passed through a 0.2 μm filter and stored at ≦−20° C. until purified by chromatography.

Example 7

Purification of Recombinant HIV-1 Group O gp41 Antigen by Chromatography

Solubilized HIV-1 Group 0 recombinant gp41 antigens obtained from Example 6 were purified by a two step method, as follows. Guanidine-HCl extracts of insoluble antigens were purified by size exclusion chromatography on a Sephacryl S-300 column equilibrated with 50 mM Tris pH 8, 8 M Urea and 0.1% BME (v/v). SDS-polyacrylamide electrophoresis was used to analyze fractions. Fractions containing the recombinant gp41 antigen were pooled and then concentrated by ultrafiltration. The recombinant antigen concentrate was treated with 4% SDS (w/v) and 5% BME (w/v) at room temperature for 3 hours. SDS treated antigen was further purified by size exclusion chromatography on a Sephacryl S-300 column equilibrated with 25 mM Tris pH 8, 0.15 M NaCl, 0.1% v/v BME, 0.1% SDS (w/v). SDS-polyacrylamide electrophoresis was used to analyze the fractions. Fractions containing purified recombinant antigen were pooled, passed through a 0.2 μm filter and stored at −70° C.

Example 8

Preparation of HIV-1 Group M Antigen

Cells containing the plasmid pTB319 were grown and induced as described in Example 5. Cells were lysed and inclusion bodies were processed essentially as described in Example 5 of U.S. Pat. No: 5,124,255, incorporated herein by reference. The pellet material was subsequently solubilized in SDS, Phosphate, pH 6.8 and then subjected to chromatography on an S-300 column.

Example 9

Preparation of HIV-2 Antigen pHIV-210/XL1-Blue cells (Example 4, hereinabove) were grown and induced as described in Example 5. Cells were lysed with a buffer containing phosphate, MgCl$_2$, Na EDTA, Triton X-100® pH 7.4 supplemented with Benzonase, Lysozyme, and PMSF. Inclusion bodies were separated from soluble proteins by centrifugation. The pellet was washed sequentially with: distilled H$_2$O; Triton X-100®, deoxycholate, NaCl, Phosphate pH 7.0; 50 mM Phosphate, pH 7.0; urea, SDS in phosphate, pH 7.0+BME. Proteins were solubilized in SDS, phosphate, pH 7.0 and BME then subjected to chromatography on an S300 column. Example 10. One Step Immunochromatographic Assay For Simultaneous Detection and Differentiation of HIV-1 group M. HIV-1 group O and HIV-2

A. Reagent preparation

1. A selenium (Se) colloid suspension was prepared substantially as follows: SeO$_2$ was dissolved in water to a concentration of 0.0625 gm/ml. Ascorbate then was dissolved in water to a concentration of 0.32 gm/ml and heated in a 70° C. water bath for 24 hours. The ascorbate solution then was diluted to 0.0065 gm/ml in water. The SeO$_2$ solution was quickly added to the diluted ascorbate solution and incubated at 42° C. Incubation was ended after a minimum of 42 hours when the absorbance maximum exceeded 30 at a wavelength between 542 nm and 588 nm. The colloid suspension was cooled to 2–8° C., then stored. Selenium colloid suspension is available from Abbott Laboratories, Abbott Park, Ill. (Code 25001).

2. Selenium colloid/antibody conjugates were prepared as follows. The selenium colloid suspension was concentrated to an absorbance of 25 (OD 500–570) in distilled water. Then, 1 M MOPS was added to a final concentration of 10 mM pH 7.2. Goat antibodies specific for human IgG Fc region (or other species of antibody specific for human IgG Fc region) were diluted to a concentration of 0.75 mg/ml with 50 mM Phosphate buffer, and the resultant antibody preparation then was added with mixing to the selenium colloid suspension prepared as described hereinabove, to a final antibody concentration of 75 μg/ml. Stirring was continued for 40 minutes. Then, 1% (by weight) bovine serum albumin (BSA) was added to the solution, and the selenium colloid/antibody conjugate solution was stirred for an additional 15 minutes and centrifuged at 5000×g for 90 minutes. Following this, 90% of the supernatant was removed, and the pellet was resuspended with the remaining supernatant. Immediately prior to coating this selenium-IgG conjugate to a glass fiber pad, it was diluted 1:10 with conjugate diluent (1% [by weight] casein, 0.1% [weight] Triton X-405®, and 50 mM Tris, pH 8.2).

3. Procedural control reagent was prepared as a mixture of HIV-1 (group M), HIV-1 (group O), and HIV-2 positive sera, and is utilized on a separate strip device as a positive control of the assay.

4. Negative control reagent used was normal human utilized on a separate test device as a negative control of the assay.

B. Application pad preparation

The application pad material comprises resin bonded glass fiber paper (Lydall). Approximately 0.1 ml of the prepared conjugate (described in preceding paragraph 2) is applied to the application pad.

C. Chromatographic Material Preparation

All reagents are applied to a nitrocellulose membrane by charge and deflect reagent jetting. The nitrocellulose is supported by a MYLAR® membrane that is coated with a pressure sensitive adhesive.

The test sample capture reagents were prepared by (a) diluting the specific antigen prepared as described hereinabove to a concentration of 0.5 mg/ml in jetting diluent (100 mM Tris, pH 7.6 with 1% sucrose (by weight), 0.9% NaCl and 5 μg/ml fluorescein) for HIV-1 group O capture reagent (pGO-9/CKS, SEQ ID NO: 50), (b) for HIV-1 group M, subgroup B capture reagent (pTB319, SEQ ID NO: 56), and (c) for HIV-2 capture reagent (pHIV-210, SEQ ID NO: 55). 0.098 μl of a first capture reagent (reagent HIV-1 group M subgroup B; SEQ ID NO: 56) was applied to the strip at the designated capture location and constituted one patient capture site. Likewise, 0.098 μl of a second capture reagent (reagent HIV-1 group O; SEQ ID NO: 50) was applied to the strip at the designated capture location and constituted one patient capture site, and 0.098 μl of a third capture reagent (reagent HIV-2; SEQ ID NO: 55) was applied to the strip at the designated capture location and constituted one patient capture site.

D. Rapid assay for the presence of antibodies to HIV

A rapid assay for the presence of antibodies to HIV in test samples serum, whole blood, saliva, and urine samples was performed as follows. In a 1.5 ml Eppendorf tube, 5 μl of serum and 600 μl of sample elution buffer (SEB) (containing 50 mM Tris, 1% BSA (w/v), 0.4% Triton X-405® (v/v), 1.5% Casein (w/v), 3% Bovine IgG (w/v), 4% E. coli lysate (v/v), [pH 8.2]) was mixed. Four drops of this mixture was applied to the sample well of the STAR housing. Next, 1 μl of serum or whole blood was added to 100 μl of SEB in a well of a microtiter plate, and the nitrocellulose strip was added in the well. Following this, 1 μl of serum or whole blood was spotted in the test device of the invention's sample well directly and 4 drops of SEB was added. When testing saliva, 50 or 75 μl of saliva was added to 50 μl or 25 μl of SEB, respectively, in a well of a microtiter plate, and the nitrocellulose test strip then was added to the well. When testing urine, 50 μl of urine was added to 50 ul of SEB in a well of a microtiter plate, and the nitrocellulose test strip was added in the well. Alternatively, 100 μl of urine was used in the well of a microtiter plate, and the nitrocellulose test strip was added, without using SEB.

The IgG in the sample was bound by the selenium-goat anti-human IgG colloid in the conjugate pad, and the complexes were chromatographed along the length of the nitrocellulose membrane test strips on which the three recombinant antigens pGO-9 CKS SEQ ID NO: 50), pTB319 (HIV-1 group M (subgroup B), SEQ ID NO: 56) and pHIV210 (HIV-2, SEQ ID NO: 55) previously were applied at a concentration of 1 mg/ml using a biodot machine, which provided positive displacement dispensing using precise drop sizes. The test device then was incubated at room temperature for two minutes, and the results were read visually.

E. Spiked Whole Blood Assay

In a 1.5 ml Eppendorf tube, the equivalent of 1 μl blood from either confirmed positive HIV-1 group O, HIV-1 group M or HIV-2, or confirmed negative for HIV-1 group O, HIV-1 group M or HIV-2 whole blood test sample was added to 5 μl of a confirmed negative HIV-1 group O, HIV-1 group M or HIV-2 serum along with 100 μl of SEB, and mixed. This mixture was applied to the sample well of the test device of the invention.

The IgG in the sample was bound by the selenium-goat anti-human IgG colloid in the conjugate pad, and the complexes were chromatographed along the length of the nitrocellulose membrane test strips on which the three recombinant antigens pGO-9 CKS SEQ ID NO: 50), pTB319 (HIV-1 group M (subgroup B), SEQ ID NO: 56) and pHIV210 (HIV-2, SEQ ID NO: 55) previously were applied at a concentration of 1 mg/ml using a biodot machine, which provided positive displacement dispensing using precise drop sizes. The test device then was incubated at room temperature for two minutes, and the results were read visually.

F. Results

If antibody to antigen 1 was present in the test sample, a visible reaction was indicated in the capture zone area of antigen 1 and in the assay completion zone, and not in the zones of antigen 2 or antigen 3. If antibody to antigen 2 was present in the test sample, a visible reaction was indicated in the capture zone area of antigen 2 and in the assay completion zone, and not in the zones of antigen 1 or antigen 3. If antibody to antigen 3 was present in the test sample, a visible reaction was indicated in the capture zone area of antigen 3 and in the assay completion zone, and not in the zones of antigen 1 or antigen 2. Also, a negative control should be non-reactive (show no visible reaction) in the zones of antigen 1, antigen 2 and antigen 3, but should be reactive in the assay completion zone. A positive control (known reactive antibody to antigen 1, 2 and/or 3) should be reactive in the zone of the appropriate antigen to which it specifically binds in an antigen/antibody reaction. A result was considered invalid when a positive reaction occurred in one of the antigen capture zones but not in the assay completion zone, and the test was repeated.

(i) Assaying for antibodies in Blood, Urine and Saliva. The blood, urine, and saliva of three patients (identified by patient numbers 0109, 4068, and 4475) were tested on nitrocellulose solid phase devices of the invention as described herein and following the assay protocol as set forth hereinabove. Each blood and urine test sample of each patient 0109, 4068 and 4475 was reactive with antigen 1 (pTB319; SEQ ID NO 56). The saliva test sample of patients 4068 and 4475 also were reactive with antigen 1, while patient 0109's saliva test sample was non-reactive in the test device of the invention. The saliva test sample of patient 0109 was later retested by a standard EIA and confirmed non-reactive for antibodies to HIV-1 gp41, indicating that the results obtained for the saliva test sample of patient 0109 were valid.

Figure 14:
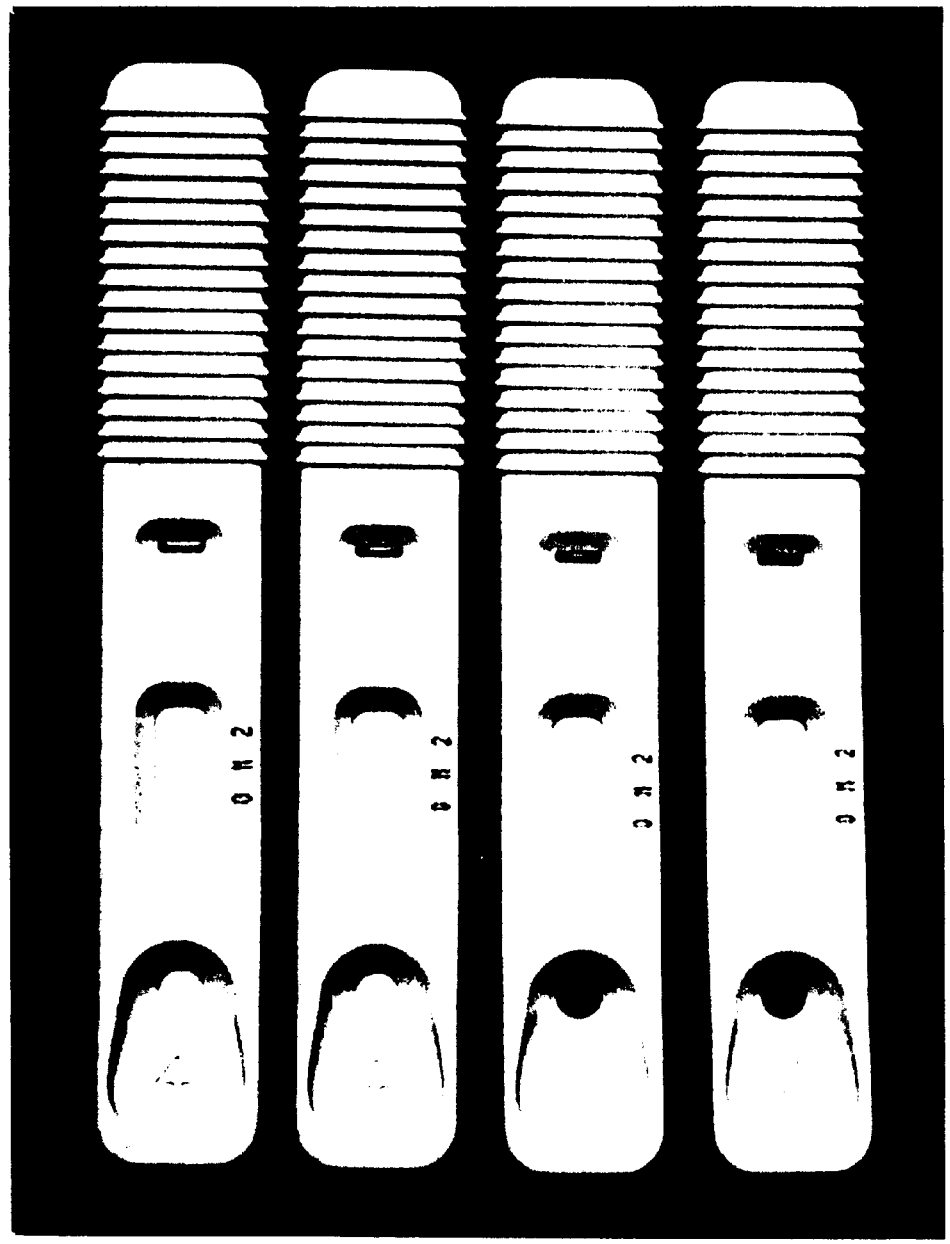

(ii) Assaying Negative Samples for HIV antibodies. FIG. 14 is a photograph of four test devices and shows the results obtained testing two negative sera and two negative whole blood test samples, each spiked with the same two negative sera. Samples contained no antibodies specific for the relevant antigens and the test samples were negative after assay on the test (i.e. no reactivity, as indicated by no visible bar signifying a reaction in either position O, M or 2. Test sample was present in each test device, as indicated by the positive reaction bar in the test sample reactivity zone.

Figure 15:
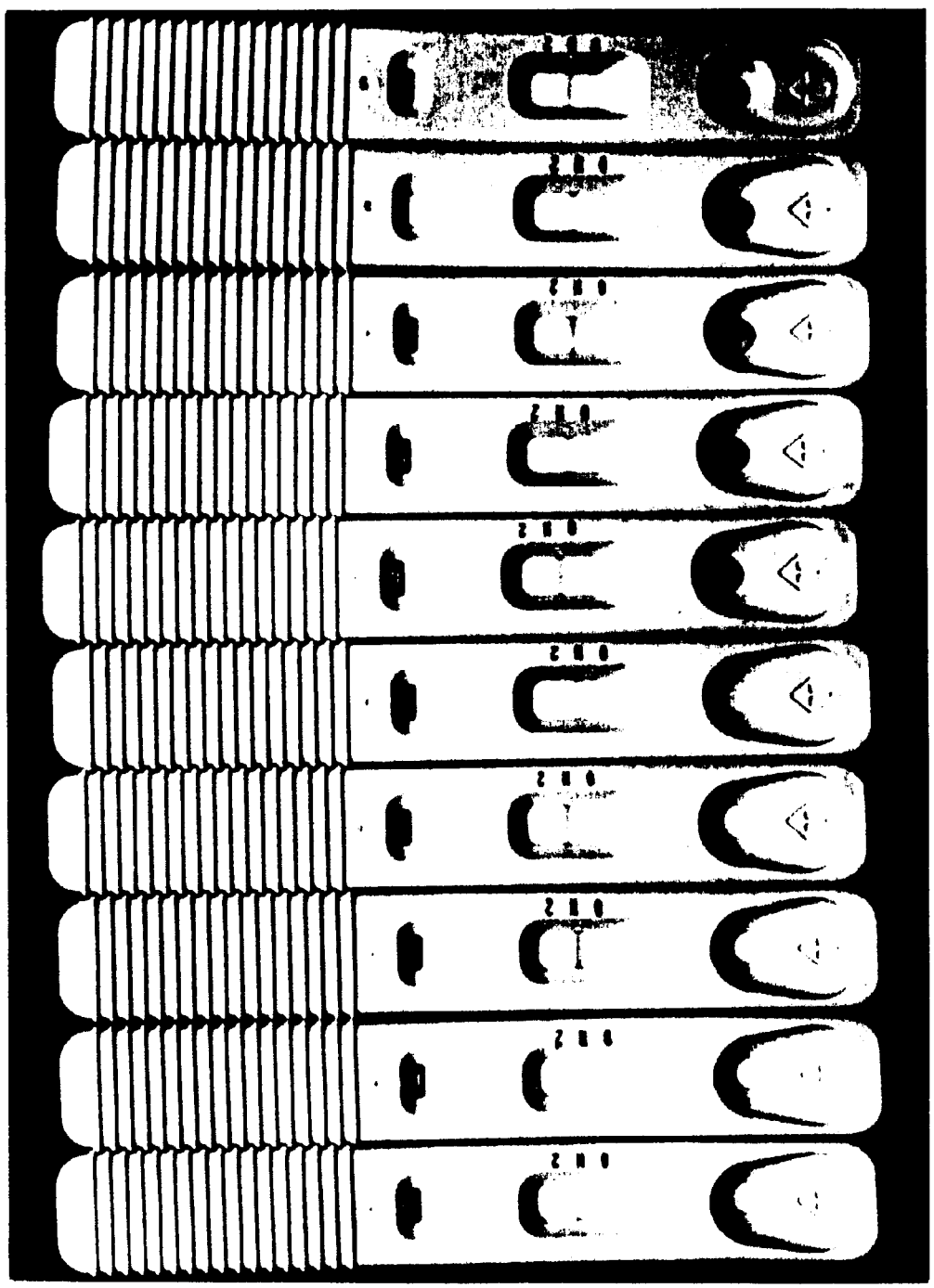

(iii) Assaying for HIV-1 group M antibody. FIG. 15 is a photograph of 10 test devices and shows the results obtained testing five HIV-1 group M sera and five whole blood samples spiked with the HIV-1 group M positive sera. As can be seen in FIG. 15, HIV-1 group M samples contained antibodies specific for HIV-1 group M antigen (pTB319: middle zone) and developed a reaction line at the HIV-1 group M antigen zone, and visible reaction lines can be seen in the assay completion zone labeled "M" of nine out of 10 test devices. Although a band was present in one particular test device in the capture zone for HIV-1 group M antibody, test sample did not to the assay completion zone and thus, the assay needed to be repeated for this particular sample. Note that no cross-reactivity was observed with the capture reagents for HIV group O and HIV-2.

Figure 16:
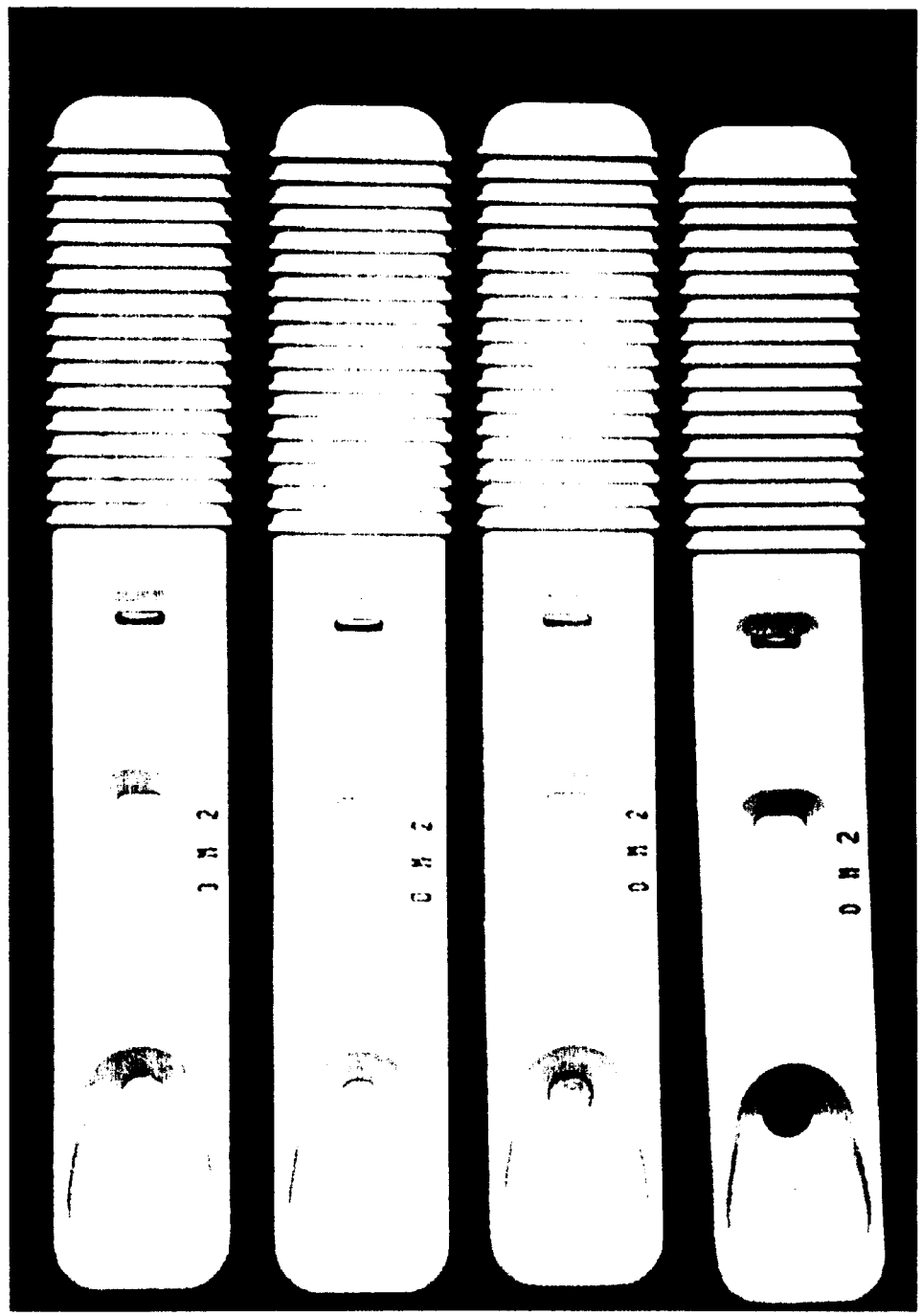

(iv) Assaying for HIV-1 group O antibodies. FIG. 16 is a photograph of four test devices, showing the results obtained when testing two confirmed positive HIV-1 group O sera and two whole blood test samples spiked with HIV-1 group O sera. As can be seen in FIG. 16, HIV-1 group O samples contained antibodies specific for HIV-1 group O antigen as indicated by the positive bar result in the HIV-1 group O antigen capture zone area (lowest zone, indicated as "O"), visible reaction lines can be seen in the assay completion zone of each device, and no cross-reaction with HIV-1 group M or HIV-2 capture antigens (no visible bar) was observed.

Figure 17:
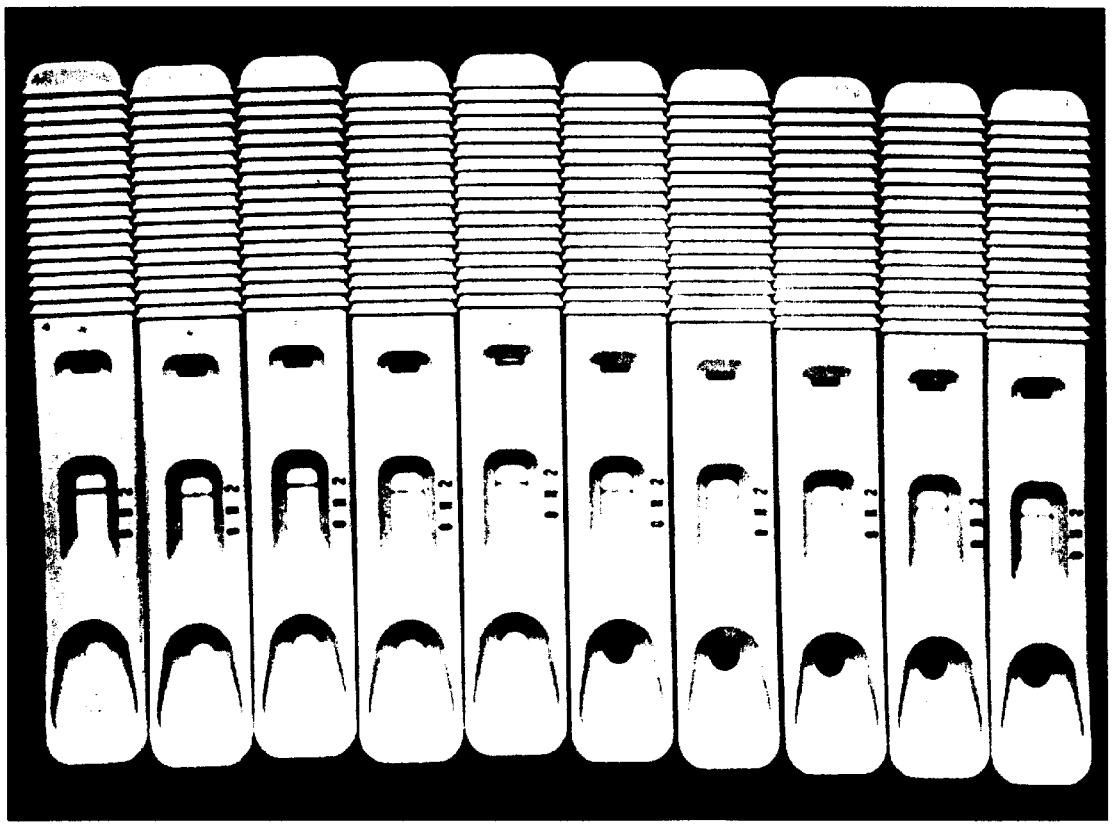

(v) Assaying for HIV-2 Antibodies. FIG. 17 is a photograph of 10 test devices showing the results obtained with five HIV-2 confirmed positive sera (five test devices to the left) and whole blood spiked with the 5 HIV-2 sera (five test devices to the right). As can be seen from FIG. 17, HIV-2 samples contained antibodies specific for HIV-2 antigen (pHIV210, upper zone, indicated by "2") as shown by the reaction bar at the HIV-2 antigen zone. No reaction was observed with these test samples and HIV-1 group O antigen or HIV-1 group M antigen, and visible reaction lines can be seen in the assay completion zone of each device.

Figure 18:
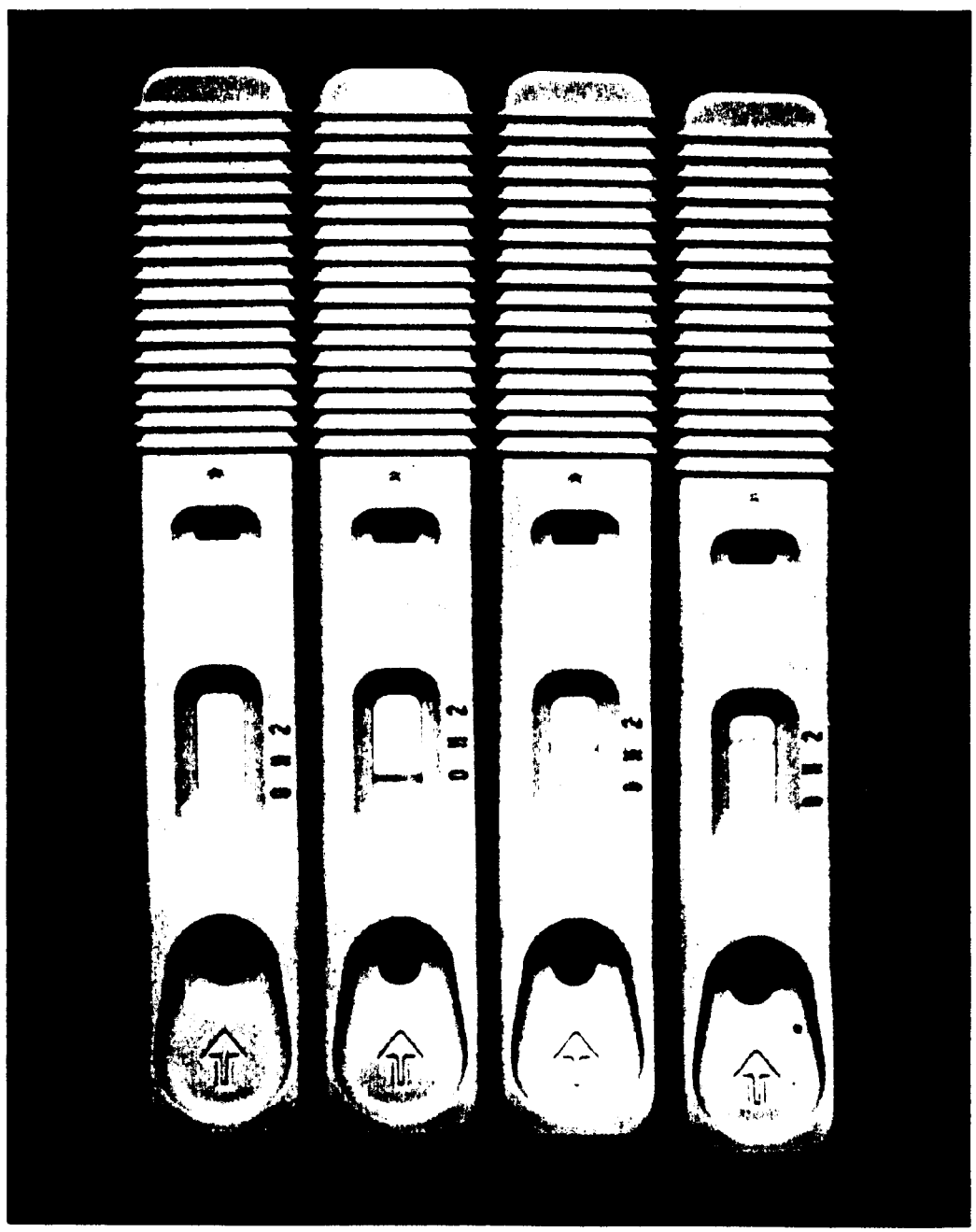

(vi) Assaying HIV-1 group M. HIV-1 group O. HIV-2 and Negative Samples. FIG. 18 is a photograph of four test devices, in which (from left to right) a negative test sample, an HIV-1 group M positive test sample, an HIV-1 group O positive test sample, and an HIV-2 positive test sample were tested individually. As can be seen from FIG. 18, the negative test serum did not react with any antigen in the antigen capture zone, while the HIV-1 group M positive test sample was reactive only with the HIV-1 group M antigen, the HIV-1 group O positive test sample was reactive only with the HIV-1 group O antigen, and the HIV-2 positive test sample was reactive only with the HIV-2 antigen, and visible reaction lines can be seen in the assay completion zone of each device.

The five HIV-1 group M and the two HIV-1 group O test samples used were confirmed seropositive samples which previously had been tested using Abbott's 3A77 EIA and has been PCR amplified, sequenced and subtyped based on phylogenetic analysis. The five HIV-2 samples used were seropositive using Abbott's 3A77 EIA and were confirmed as HIV-2 samples by an HIV-2 Western blot test (Sanofi).

We claim:

1. A method for simultaneously detecting and differentiating between analytes comprising antibodies to HIV-1 group O, HIV-1 group M, and HIV-2 in a test sample, comprising:

(a) contacting said test sample with an analytical device having a strip with a proximal end and a distal end, wherein said test sample moves from said proximal end to about said distal end by capillary action, and wherein said strip contains at least one immobilized capture reagent per analyte, for a time and under conditions sufficient to form capture reagent / analyte complexes by the binding of said analyte and said capture reagent; and (b) determining the presence of the analyte(s) by detecting a visible color change at the capture reagent site on the strip, wherein said capture reagent for HIV-1 group O comprises a polypeptide selected from the group consisting of SEQ ID NO: 48, SEQ ID NO: 50, SEQ ID NO: 52, SEQ ID NO: 54, SEQ ID NO: 58, and SEQ ID NO: 60, said capture reagent for HIV-1 group M comprises a polypeptide SEQ ID NO: 56, and said capture reagent for HIV-2 comprises a polypeptide SEQ ID NO: 55.

2. The method of claim 1, wherein said immobilized capture reagent is configured as a letter, number, icon, or symbol.

3. The method of claim 1, wherein a labeled reagent is contained within the strip in a situs between the proximal end and the immobilized patient capture reagent.

4. The method of claim 1, wherein said polypeptide capture reagents are produced by recombinant technology.

5. The method of claim 3, wherein said labeled reagent is selenium.

6. The method of claim 1, wherein said test sample is a body fluid.

7. The method of claim 6, wherein said body fluid is selected from the group consisting of whole blood, serum, plasma, urine and saliva.

8. An analytical device for simultaneous detecting and differentiating between HIV-1 group O, HIV-1 group M and HIV-2 in a test sample, comprising a strip with a proximal end and a distal end, wherein said test sample is capable of moving from said proximal end to about said distal end by capillary action, and wherein said strip contains at least one immobilized capture reagent per analyte, for binding of said analyte and said capture reagent; and wherein said capture reagent for HIV-1 group O comprises a polypeptide selected from the group consisting of SEQ ID NO: 48, SEQ ID NO: 50, SEQ ID NO: 52, SEQ ID NO: 54, SEQ ID NO: 58, and SEQ ID NO: 60, said capture reagent for HIV-1 group M comprises a polypeptide SEQ ID NO: 56, and said capture reagent for HIV-2 comprises a polypeptide SEQ ID NO: 55.

9. The analytical device of claim 8, wherein said immobilized capture reagent is configured as a letter, number, icon, or symbol.

10. The analytical device of claim 8, wherein a labeled reagent is contained within the strip in a situs between the proximal end and the immobilized patient capture reagent.

11. The analytical device of claim 10, wherein said labeled reagent is selenium.

12. The analytical device of claim 8, wherein said test sample is a body fluid.

13. The analytical device of claim 12, wherein said body fluid is selected from the group consisting of whole blood, serum, plasma, urine and saliva.

14. The analytical device of claim 8 wherein said polypeptide capture reagents are produced by recombinant technology.

15. A kit for use in specific binding assays, having an analytical device for determining the presence or amount of HIV-1 group O, HIV-1 group M and HIV-2 in a test sample, comprising a strip having a proximal end and a distal end, wherein said test sample is capable of moving from said proximal end to about said distal end by capillary action, and wherein said strip contains an immobilized capture reagent that binds to a member selected from the group consisting of the analyte, an ancillary specific binding member and a labeled reagent, and wherein said capture reagent for HIV-1 group O comprises a polypeptide selected from the group consisting of SEQ ID NO: 48, SEQ ID NO: 50, SEQ ID NO: 52, SEQ ID NO: 54, SEQ ID NO: 58, and SEQ ID NO: 60, said capture reagent for HIV-1 group M comprises a polypeptide SEQ ID NO: 56, and said capture reagent for HIV-2 comprises a polypeptide SEQ ID NO: 55.

16. The test kit of claim 15 wherein said labeled reagent is selenium.

17. The test kit of claim 15, further comprising a positive reagent control.

18. The test kit of claim 15, further comprising a negative reagent control.

19. The test kit of claim 15, wherein said polypeptide capture reagents are produced by recombinant technology.

* * * * *

UNITED STATES PATENT AND TRADEMARK OFFICE
CERTIFICATE OF CORRECTION

PATENT NO. : 5,922,533
DATED : July 13, 1999
INVENTOR(S) : Anadruzela S. Vallari et al.

It is certified that error appears in the above-identified patent and that said Letters Patent is hereby corrected as shown below:

Title page, before item no. 54 ("Title"): Delete the word "pullout".

Title page, item no. 57 ("Abstract"): Replace "An analytical. device also..." with -- An analytical device also is provided for performing the method which includes these capture reagents. --

Title page, item no. 75 ("Inventors"): Replace "Anadruzela S. Vallari; " with -- Anadruzela S. Vallari, Grayslake; --

Title page, item no. 75 ("Inventors"): Replace "both of Libertyville" with -- Libertyville --

Signed and Sealed this

Twenty-second Day of August, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 89

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO:1:

GAGATCTTCA GGGGTATCC                                             19

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

GGATCATCGG TTCATCACCC                                            20

(2) INFORMATION FOR SEQ ID NO:3:

(i) SEQUENCE CHARACTERISTICS:
      (A) LENGTH: 114 base pairs
      (B) TYPE: nucleic acid
      (C) STRANDEDNESS: single
      (D) TOPOLOGY: linear (xi) SEQUENCE DESCRIPTION: SEQ ID NO:3:

CATGATCGGT GGTGACATGA AAGACATCTG GCGTAACGAA CTGTTCAAAT ACAAAGTTGT    60

TCGTGTTAAA CCGTTCTCTG TTGCTCCGAC CCCGATCGCT CGTCCGGTTA TCGG    114

(2) INFORMATION FOR SEQ ID NO:4:

(i) SEQUENCE CHARACTERISTICS:
      (A) LENGTH: 111 base pairs

```
            (B) TYPE: nucleic acid
            (C) STRANDEDNESS: single
            (D) TOPOLOGY: linear (xi) SEQUENCE DESCRIPTION: SEQ ID NO:4:

GCAGGTTCCA CTATGGGTGC TGCAGCTACC GCTCTGACCG TACAGACCCA CTCTGTTATC      60

AAAGGTATCG TACAGCAGCA CGACAACCTG CTGCGTGCAA TCCAGGCACA G              111

(2) INFORMATION FOR SEQ ID NO:5:

(i) SEQUENCE CHARACTERISTICS:
            (A) LENGTH: 110 base pairs
            (B) TYPE: nucleic acid
            (C) STRANDEDNESS: single
            (D) TOPOLOGY: linear (xi) SEQUENCE DESCRIPTION: SEQ ID NO:5:

AGCTGCTGGT TCTGGATCAG GGTTTCCAGT GCCAGCAGAC GAGCACGCAG CTGACGGATA      60

CCCCATACAG ACAGACGCAG CAGTTCCTGC TGTGCCTGGA TTGCACGCAG                110

(2) INFORMATION FOR SEQ ID NO:6:

(i) SEQUENCE CHARACTERISTICS:
            (A) LENGTH: 111 base pairs
            (B) TYPE: nucleic acid
            (C) STRANDEDNESS: single
            (D) TOPOLOGY: linear (xi) SEQUENCE DESCRIPTION: SEQ ID NO:6:

CTGATCCAGA ACCAGCAGCT GCTGAACCTG TGGGGCTGCA AAGGTCGTCT GATCTGCTAC      60

ACCTCCGTTA AATGGAACGA AACCTGGCGT AACACCACCA ACATCAACCA G              111

(2) INFORMATION FOR SEQ ID NO:7:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (xi) SEQUENCE DESCRIPTION: SEQ ID NO:7:

CTGAACCTGA GCTTTCTGGA TTTCTTCGTA GATGGTGGAA GAAACGTTGT CGATCTGCTG      60

GTCCCATTCC TGCCAGGTCA GGTTACCCCA GATCTGGTTG ATGTTGGTGG TGTTACG         117

(2) INFORMATION FOR SEQ ID NO:8:

(i) SEQUENCE CHARACTERISTICS:
            (A) LENGTH: 101 base pairs
            (B) TYPE: nucleic acid
            (C) STRANDEDNESS: single
            (D) TOPOLOGY: linear (xi) SEQUENCE DESCRIPTION: SEQ ID NO:8:

TCCAGAAAGC TCAGGTTCAG CAGGAACAGA ACGAAAAAAA ACTGCTGGAA CTGGACGAAT      60

GGGCTTCTCT GTGGAACTGG CTGGACATCA CCAAATGGCT G                         101

(2) INFORMATION FOR SEQ ID NO:9:

(i) SEQUENCE CHARACTERISTICS:
            (A) LENGTH: 114 base pairs
            (B) TYPE: nucleic acid
            (C) STRANDEDNESS: single
            (D) TOPOLOGY: linear (xi) SEQUENCE DESCRIPTION: SEQ ID NO:9:
```

```
ACCTTCACCG GTACGACCCG GAGTTTCAGC TTCAGACTGC TGACGGGTCG GGATCTGCAG      60

GGACAGCGGC TGGTAGCCCT GACGGATGTT ACGCAGCCAT TTGGTGATGT CCAG          114
```

(2) INFORMATION FOR SEQ ID NO:10:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (xi) SEQUENCE DESCRIPTION: SEQ ID NO:10:

```
CGGGTCGTAC CGGTGAAGGT GGTGGTGACG AAGGCCGTCC GCGTCTGATC CCGTCTCCGC      60

AGGGTTTCCT GCCGCTGCTG TACACCGACC TGCGTACCAT CATCCTG                  107
```

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:11:

```
CTACAAGAAT TCCATGATCG GTGGTGACAT G                                    31
```

(2) INFORMATION FOR SEQ ID NO:12:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (xi) SEQUENCE DESCRIPTION: SEQ ID NO:12:

```
GTCTGTGGAT TCTGGGTCAG AAAATCATCG ACGCTTGCCG TATCTGCGCT GCTGTTATCC      60

ACTACTGGCT GCAGGAACTG CAGAAATCCG CTACCTCCCT GATCGACAC                109
```

(2) INFORMATION FOR SEQ ID NO:13:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO:13:

```
GCGAACACGA CGCGGGATGT TCAGGATACC ACGACCCAGA CGCTGGATAC CACGGATGAT      60

GTCGTCAGTC CAGTTAGCAA CTGCAACAGC GAAGGTGTCG ATCAGGGAGG TAGC          114
```

(2) INFORMATION FOR SEQ ID NO:14:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:14:

```
ATAGTAGGAT CCTATTACAG CAGAGAGCGT TCGAAGCCCT GGCGAACACG ACGCGGGATG      60
```

(2) INFORMATION FOR SEQ ID NO:15:

(i) SEQUENCE CHARACTERISTICS:

(A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:15:

ATAGTAGGAT CCTATTATTC ACCGGTACGA CCCGGAGTTT CAG                43

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:16:

ATAGTAGGAT CCTATTACAG CCATTTGGTG ATGTCCAG                      38

(2) INFORMATION FOR SEQ ID NO:17:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (xi) SEQUENCE DESCRIPTION: SEQ ID NO:17:

GCACCCATAG TGGAACCTGC TGCAGACAGA ACGCCCAGGA ACAGCATACC CAGACCTACA    60

GCACGTTTTT CACGGTGGGT GCCAGTACCG ATAACCGGAC GAGCGA                  106

(2) INFORMATION FOR SEQ ID NO:18:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (xi) SEQUENCE DESCRIPTION: SEQ ID NO:18:

CTGACCCAGA ATCCACAGAC CCAGACGCAG GTGAGAGATA ACAGTCTGAG TACCAGAGAT    60

CAGGTTAGAC AGCAGGTGGT AGGACCACAG GATGATGGTA CGCAGGTC               108

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:19:

GCAGCTTCGT GTTCTGTGGT ACGGCG                                        26

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:20:

CGTAACGGTA CGACACTCC                                                19

(2) INFORMATION FOR SEQ ID NO:21:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (xi) SEQUENCE DESCRIPTION: SEQ ID NO:21:

CCGCTACCTC CCTGATCGAC ACCTTC                                                26

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:22:

GAAGGTGTCG ATCAGGGAGG TAGCGG                                                26

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:23:

GATGTCCAGC CAGTTCCAC                                                        19

(2) INFORMATION FOR SEQ ID NO:24:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:24:

CTACAAGAAT TCCATGATCG GTGGTGACAT GAAAGACATC TGGCGTAACG AACTGTTCAA            60

ATAC                                                                        64

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:25:

CTACAAGAAT TCTATCGGTG GTGACATGAA AGAC                                       34

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

CGGGTCGTAC CGGTGAAGGT                                                       20

(2) INFORMATION FOR SEQ ID NO:27:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:27:

ATAGTAGGAT CCTATTACAG CAG                                              23

(2) INFORMATION FOR SEQ ID NO:28:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:28:

GCCGGAAGCG AGAAGAATC                                                   19

(2) INFORMATION FOR SEQ ID NO:29:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:29:

TATCGTACAG CAGCAGGAC                                                   19

(2) INFORMATION FOR SEQ ID NO:30:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:30:

CCCATTAATG TGAGTTAGCT C                                                21

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:31:

CCTGACGAAT GATTGTCGCA                                                  20

(2) INFORMATION FOR SEQ ID NO:32:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:32:

ATTCAGCGAC GACACGGTG                                                   19

(2) INFORMATION FOR SEQ ID NO:33:

(i) SEQUENCE CHARACTERISTICS:

(A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:33:

GTATCCACAC CTGTGCCA                                                         18

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:34:

AGAGTGGGTC TGTACGGTC                                                        19

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

AATGGGCTTC TCTGTGGAAC                                                       20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

CTGTCTAACC TGATCTCTGG                                                       20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:37:

ACGCAGGTGA GAGATAACAG                                                       20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:38:

GTGATACGAA ACGAAGCATT GG                                                    22

(2) INFORMATION FOR SEQ ID NO:39:

(i) SEQUENCE CHARACTERISTICS:
        (A) LENGTH: 21 base pairs
        (B) TYPE: nucleic acid (C) STRANDEDNESS: single
        (D) TOPOLOGY: linear (xi) SEQUENCE DESCRIPTION: SEQ ID NO:39:

GCGATATAGG CGCCAGCAAC C                                              21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:40:

CTCTGTTATC AAAGGTATCG T                                              21

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:41:

AGCAGACGAG CACGCAGC                                                  18

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:42:

TTCAGCAGGA ACAGAACG                                                  18

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:43:

TCCGCGTCTG ATCCCGTC                                                  18

(2) INFORMATION FOR SEQ ID NO:44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:44:

CCAGGCACAG CAGGAAC                                                   17

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:45:

ACACTATAGA ATACTCAAGC                                                    20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:46:

TAATACGACT CACTATAGGG                                                    20

(2) INFORMATION FOR SEQ ID NO:47:

(i) SEQUENCE CHARACTERISTICS:
        (A) LENGTH: 741 base pairs
        (B) TYPE: nucleic acid
        (C) STRANDEDNESS: single
        (D) TOPOLOGY: linear (xi) SEQUENCE DESCRIPTION: SEQ ID NO:47:

ATGATCGGTG GTGACATGAA AGACATCTGG CGTAACGAAC TGTTCAAATA CAAAGTTGTT         60

CGTGTTAAAC CGTTCTCTGT TGCTCCGACC CCGATCGCTC GTCCGGTTAT CGGTACTGGC        120

ACCCACCGTG AAAAACGTGC TGTAGGTCTG GGTATGCTGT TCCTGGGCGT TCTGTCTGCA        180

GCAGGTTCCA CTATGGGTGC TGCAGCTACC GCTCTGACCG TACAGACCCA CTCTGTTATC        240

AAAGGTATCG TACAGCAGCA GGACAACCTG CTGCGTGCAA TCCAGGCACA GCAGGAACTG        300

CTGCGTCTGT CTGTATGGGG TATCCGTCAG CTGCGTGCTC GTCTGCTGGC ACTGGAAACC        360

CTGATCCAGA ACCAGCAGCT GCTGAACCTG TGGGGCTGCA AGGTCGTCT GATCTGCTAC        420

ACCTCCGTTA ATGGAACGA AACCTGGCGT AACACCACCA CATCAACCA GATCTGGGGT         480

AACCTGACCT GGCAGGAATG GGACCAGCAG ATCGACAACG TTTCTTCCAC CATCTACGAA        540

GAAATCCAGA AAGCTCAGGT TCAGCAGGAA CAGAACGAAA AAAAACTGCT GGAACTGGAC        600

GAATGGGCTT CTCTGTGGAA CTGGCTGGAC ATCACCAAAT GGCTGCGTAA CATCCGTCAG        660

GGCTACCAGC CGCTGTCCCT GCAGATCCCG ACCCGTCAGC AGTCTGAAGC TGAAACTCCG        720

GGTCGTACCG GTGAATAATA G                                                 741

(2) INFORMATION FOR SEQ ID NO:48:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Met Ile Gly Gly Asp Met Lys Asp Ile Trp Arg Asn Glu Leu Phe Lys
 1               5                  10                  15

Tyr Lys Val Val Arg Val Lys Pro Phe Ser Val Ala Pro Thr Pro Ile
            20                  25                  30

Ala Arg Pro Val Ile Gly Thr Gly Thr His Arg Glu Lys Arg Ala Val
        35                  40                  45

Gly Leu Gly Met Leu Phe Leu Gly Val Leu Ser Ala Ala Gly Ser Thr
    50                  55                  60

```
Met Gly Ala Ala Ala Thr Ala Leu Thr Val Gln Thr His Ser Val Ile
 65                  70                  75                  80

Lys Gly Ile Val Gln Gln Asp Asn Leu Leu Arg Ala Ile Gln Ala
                 85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
            115                 120                 125

Asn Leu Trp Gly Cys Lys Gly Arg Leu Ile Cys Tyr Thr Ser Val Lys
130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
            195                 200                 205

Leu Asp Ile Thr Lys Trp Leu Arg Asn Ile Arg Gln Gly Tyr Gln Pro
210                 215                 220

Leu Ser Leu Gln Ile Pro Thr Arg Gln Gln Ser Glu Ala Glu Thr Pro
225                 230                 235                 240

Gly Arg Thr Gly Glu
                245

(2) INFORMATION FOR SEQ ID NO:49:

(i) SEQUENCE CHARACTERISTICS:
        (A) LENGTH: 1476 base pairs
        (B) TYPE: nucleic acid
        (C) STRANDEDNESS: single
        (D) TOPOLOGY: linear (xi) SEQUENCE DESCRIPTION: SEQ ID NO:49:

ATGAGTTTTG TGGTCATTAT TCCCGCGCGC TACGCGTCGA CGCGTCTGCC CGGTAAACCA      60

TTGGTTGATA TTAACGGCAA ACCCATGATT GTTCATGTTC TTGAACGCGC GCGTGAATCA     120

GGTGCCGAGC GCATCATCGT GGCAACCGAT CATGAGGATG TTGCCCGCGC CGTTGAAGCC     180

GCTGGCGGTG AAGTATGTAT GACGCGCGCC GATCATCAGT CAGGAACAGA ACGTCTGGCG     240

GAAGTTGTCG AAAAATGCGC ATTCAGCGAC GACACGGTGA TCGTTAATGT GCAGGGTGAT     300

GAACCGATGA TCCCTGCGAC AATCATTCGT CAGGTTGCTG ATAACCTCGC TCAGCGTCAG     360

GTGGGTATGA CGACTCTGGC GGTGCCAATC ACAATGCGG AAGAAGCGTT TAACCCGAAT      420

GCGGTGAAAG TGGTTCTCGA CGCTGAAGGG TATGCACTGT ACTTCTCTCG CGCCACCATT     480

CCTTGGGATC GTGATCGTTT TGCAGAAGGC CTTGAAACCG TTGGCGATAA CTTCCTGCGT     540

CATCTTGGTA TTTATGGCTA CCGTGCAGGC TTTATCCGTC GTTACGTCAA CTGGCAGCCA     600

AGTCCGTTAG AACACATCGA AATGTTAGAG CAGCTTCGTG TTCTGTGGTA CGGCGAAAAA     660

ATCCATGTTG CTGTTGCTCA GGAAGTTCCT GGCACAGGTG TGGATACCCC TGAAGATCTC     720

GACCCGTCGA CGAATTCTAT CGGTGGTGAC ATGAAAGACA TCTGGCGTAA CGAACTGTTC     780

AAATACAAAG TTGTTCGTGT TAAACCGTTC TCTGTTGCTC CGACCCCGAT CGCTCGTCCG     840

GTTATCGGTA CTGGCACCCA CCGTGAAAAA CGTGCTGTAG GTCTGGGTAT GCTGTTCCTG     900

GGCGTTCTGT CTGCAGCAGG TTCCACTATG GGTGCTGCAG CTACCGCTCT GACCGTACAG     960

ACCCACTCTG TTATCAAAGG TATCGTACAG CAGCAGGACA ACCTGCTGCG TGCAATCCAG    1020
```

```
GCACAGCAGG AACTGCTGCG TCTGTCTGTA TGGGGTATCC GTCAGCTGCG TGCTCGTCTG      1080

CTGGCACTGG AAACCCTGAT CCAGAACCAG CAGCTGCTGA ACCTGTGGGG CTGCAAAGGT      1140

CGTCTGATCT GCTACACCTC CGTTAAATGG AACGAAACCT GGCGTAACAC CACCAACATC      1200

AACCAGATCT GGGGTAACCT GACCTGGCAG GAATGGGACC AGCAGATCGA CAACGTTTCT      1260

TCCACCATCT ACGAAGAAAT CCAGAAAGCT CAGGTTCAGC AGGAACAGAA CGAAAAAAAA      1320

CTGCTGGAAC TGGACGAATG GCTTCTCTG TGGAACTGGC TGGACATCAC CAAATGGCTG       1380

CGTAACATCC GTCAGGGCTA CCAGCCGCTG TCCCTGCAGA TCCGACCCG TCAGCAGTCT        1440

GAAGCTGAAA CTCCGGGTCG TACCGGTGAA TAATAG                                1476
```

(2) INFORMATION FOR SEQ ID NO:50:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
               100                 105                 110

Ala Asp Asn Leu Ala Gln Arg Gln Val Gly Met Thr Thr Leu Ala Val
           115                 120                 125

Pro Ile His Asn Ala Glu Glu Ala Phe Asn Pro Asn Ala Val Lys Val
       130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
           180                 185                 190

Arg Arg Tyr Val Asn Trp Gln Pro Ser Pro Leu Glu His Ile Glu Met
       195                 200                 205

Leu Glu Gln Leu Arg Val Leu Trp Tyr Gly Glu Lys Ile His Val Ala
   210                 215                 220

Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
                245                 250                 255

Asn Glu Leu Phe Lys Tyr Lys Val Val Arg Val Lys Pro Phe Ser Val
           260                 265                 270
```

```
Ala Pro Thr Pro Ile Ala Arg Pro Val Ile Gly Thr Gly Thr His Arg
        275                 280                 285

Glu Lys Arg Ala Val Gly Leu Gly Met Leu Phe Leu Gly Val Leu Ser
    290                 295                 300

Ala Ala Gly Ser Thr Met Gly Ala Ala Thr Ala Leu Thr Val Gln
305                 310                 315                 320

Thr His Ser Val Ile Lys Gly Ile Val Gln Gln Asp Asn Leu Leu
                325                 330                 335

Arg Ala Ile Gln Ala Gln Gln Glu Leu Leu Arg Leu Ser Val Trp Gly
            340                 345                 350

Ile Arg Gln Leu Arg Ala Arg Leu Leu Ala Leu Glu Thr Leu Ile Gln
        355                 360                 365

Asn Gln Gln Leu Leu Asn Leu Trp Gly Cys Lys Gly Arg Leu Ile Cys
    370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Ile
                405                 410                 415

Asp Asn Val Ser Ser Thr Ile Tyr Glu Glu Ile Gln Lys Ala Gln Val
            420                 425                 430

Gln Gln Glu Gln Asn Glu Lys Lys Leu Leu Glu Leu Asp Glu Trp Ala
        435                 440                 445

Ser Leu Trp Asn Trp Leu Asp Ile Thr Lys Trp Leu Arg Asn Ile Arg
    450                 455                 460

Gln Gly Tyr Gln Pro Leu Ser Leu Gln Ile Pro Thr Arg Gln Gln Ser
465                 470                 475                 480

Glu Ala Glu Thr Pro Gly Arg Thr Gly Glu
                485                 490

(2) INFORMATION FOR SEQ ID NO:51:

(i) SEQUENCE CHARACTERISTICS:
        (A) LENGTH: 1125 base pairs
        (B) TYPE: nucleic acid
        (C) STRANDEDNESS: single
        (D) TOPOLOGY: linear (xi) SEQUENCE DESCRIPTION: SEQ ID NO:51:

ATGATCGGTG GTGACATGAA AGACATCTGG CGTAACGAAC TGTTCAAATA CAAAGTTGTT      60

CGTGTTAAAC CGTTCTCTGT TGCTCCGACC CCGATCGCTC GTCCGGTTAT CGGTACTGGC     120

ACCCACCGTG AAAAACGTGC TGTAGGTCTG GGTATGCTGT TCCTGGGCGT TCTGTCTGCA     180

GCAGGTTCCA CTATGGGTGC TGCAGCTACC GCTCTGACCG TACAGACCCA CTCTGTTATC     240

AAAGGTATCG TACAGCAGCA GGACAACCTG CTGCGTGCAA TCCAGGCACA GCAGGAACTG     300

CTGCGTCTGT CTGTATGGGG TATCCGTCAG CTGCGTGCTC GTCTGCTGGC ACTGGAAACC     360

CTGATCCAGA ACCAGCAGCT GCTGAACCTG TGGGGCTGCA AAGGTCGTCT GATCTGCTAC     420

ACCTCCGTTA AATGGAACGA AACCTGGCGT AACACCACCA ACATCAACCA GATCTGGGGT     480

AACCTGACCT GGCAGGAATG GGACCAGCAG ATCGACAACG TTTCTTCCAC CATCTACGAA     540

GAAATCCAGA AAGCTCAGGT TCAGCAGGAA CAGAACGAAA AAAAACTGCT GGAACTGGAC     600

GAATGGGCTT CTCTGTGGAA CTGGCTGGAC ATCACCAAAT GGCTGCGTAA CATCCGTCAG     660

GGCTACCAGC CGCTGTCCCT GCAGATCCCG ACCCGTCAGC AGTCTGAAGC TGAAACTCCG     720

GGTCGTACCG GTGAAGGTGG TGGTGACGAA GGCCGTCCGC GTCTGATCCC GTCTCCGCAG     780
```

```
GGTTTCCTGC CGCTGCTGTA CACCGACCTG CGTACCATCA TCCTGTGGTC CTACCACCTG    840

CTGTCTAACC TGATCTCTGG TACTCAGACT GTTATCTCTC ACCTGCGTCT GGGTCTGTGG    900

ATTCTGGGTC AGAAAATCAT CGACGCTTGC CGTATCTGCG CTGCTGTTAT CCACTACTGG    960

CTGCAGGAAC TGCAGAAATC CGCTACCTCC CTGATCGACA CCTTCGCTGT TGCAGTTGCT   1020

AACTGGACTG ACGACATCAT CCTGGGTATC CAGCGTCTGG GTCGTGGTAT CCTGAACATC   1080

CCGCGTCGTG TTCGCCAGGG CTTCGAACGC TCTCTGCTGT AATAG                   1125
```

(2) INFORMATION FOR SEQ ID NO:52:

(i) SEQUENCE CHARACTERISTICS:
        (A) LENGTH: 373 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

```
Met Ile Gly Gly Asp Met Lys Asp Ile Trp Arg Asn Glu Leu Phe Lys
 1               5                  10                  15

Tyr Lys Val Val Arg Val Lys Pro Phe Ser Val Ala Pro Thr Pro Ile
            20                  25                  30

Ala Arg Pro Val Ile Gly Thr Gly Thr His Arg Glu Lys Arg Ala Val
        35                  40                  45

Gly Leu Gly Met Leu Phe Leu Gly Val Leu Ser Ala Ala Gly Ser Thr
    50                  55                  60

Met Gly Ala Ala Ala Thr Ala Leu Thr Val Gln Thr His Ser Val Ile
65                  70                  75                  80

Lys Gly Ile Val Gln Gln Gln Asp Asn Leu Leu Arg Ala Ile Gln Ala
                85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
        115                 120                 125

Asn Leu Trp Gly Cys Lys Gly Arg Leu Ile Cys Tyr Thr Ser Val Lys
    130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
        195                 200                 205

Leu Asp Ile Thr Lys Trp Leu Arg Asn Ile Arg Gln Gly Tyr Gln Pro
    210                 215                 220

Leu Ser Leu Gln Ile Pro Thr Arg Gln Gln Ser Glu Ala Glu Thr Pro
225                 230                 235                 240

Gly Arg Thr Gly Glu Gly Gly Asp Glu Gly Arg Pro Arg Leu Ile
                245                 250                 255

Pro Ser Pro Gln Gly Phe Leu Pro Leu Leu Tyr Thr Asp Leu Arg Thr
            260                 265                 270

Ile Ile Leu Trp Ser Tyr His Leu Leu Ser Asn Leu Ile Ser Gly Thr
        275                 280                 285

Gln Thr Val Ile Ser His Leu Arg Leu Gly Leu Trp Ile Leu Gly Gln
```

```
                    290                 295                 300
Lys Ile Ile Asp Ala Cys Arg Ile Cys Ala Ala Val Ile His Tyr Trp
305                 310                 315                 320

Leu Gln Glu Leu Gln Lys Ser Ala Thr Ser Leu Ile Asp Thr Phe Ala
                325                 330                 335

Val Ala Val Ala Asn Trp Thr Asp Asp Ile Ile Leu Gly Ile Gln Arg
            340                 345                 350

Leu Gly Arg Gly Ile Leu Asn Ile Pro Arg Arg Val Arg Gln Gly Phe
        355                 360                 365

Glu Arg Ser Leu Leu
    370
```

(2) INFORMATION FOR SEQ ID NO:53:

(i) SEQUENCE CHARACTERISTICS:
        (A) LENGTH: 1860 base pairs
        (B) TYPE: nucleic acid
        (C) STRANDEDNESS: single
        (D) TOPOLOGY: linear (xi) SEQUENCE DESCRIPTION: SEQ ID NO:53:

```
ATGAGTTTTG TGGTCATTAT TCCCGCGCGC TACGCGTCGA CGCGTCTGCC CGGTAAACCA      60
TTGGTTGATA TTAACGGCAA ACCCATGATT GTTCATGTTC TTGAACGCGC GCGTGAATCA     120
GGTGCCGAGC GCATCATCGT GGCAACCGAT CATGAGGATG TTGCCCGCGC CGTTGAAGCC     180
GCTGGCGGTG AAGTATGTAT GACGCGCGCC GATCATCAGT CAGGAACAGA ACGTCTGGCG     240
GAAGTTGTCG AAAAATGCGC ATTCAGCGAC GACACGGTGA TCGTTAATGT GCAGGGTGAT     300
GAACCGATGA TCCCTGCGAC AATCATTCGT CAGGTTGCTG ATAACCTCGC TCAGCGTCAG     360
GTGGGTATGA CGACTCTGGC GGTGCCAATC CACAATGCGG AAGAAGCGTT TAACCCGAAT     420
GCGGTGAAAG TGGTTCTCGA CGCTGAAGGG TATGCACTGT ACTTCTCTCG CGCCACCATT     480
CCTTGGGATC GTGATCGTTT TGCAGAAGGC CTTGAAACCG TTGGCGATAA CTTCCTGCGT     540
CATCTTGGTA TTTATGGCTA CCGTGCAGGC TTTATCCGTC GTTACGTCAA CTGGCAGCCA     600
AGTCCGTTAG AACACATCGA AATGTTAGAG CAGCTTCGTG TTCTGTGGTA CGGCGAAAAA     660
ATCCATGTTG CTGTTGCTCA GGAAGTTCCT GGCACAGGTG TGGATACCCC TGAAGATCTC     720
GACCCGTCGA CGAATTCTAT CGGTGGTGAC ATGAAAGACA TCTGGCGTAA CGAACTGTTC     780
AAATACAAAG TTGTTCGTGT TAAACCGTTC TCTGTTGCTC CGACCCCGAT CGCTCGTCCG     840
GTTATCGGTA CTGGCACCCA CCGTGAAAAA CGTGCTGTAG GTCTGGGTAT GCTGTTCCTG     900
GGCGTTCTGT CTGCAGCAGG TTCCACTATG GGTGCTGCAG CTACCGCTCT GACCGTACAG     960
ACCCACTCTG TTATCAAAGG TATCGTACAG CAGCAGGACA ACCTGCTGCG TGCAATCCAG    1020
GCACAGCAGG AACTGCTGCG TCTGTCTGTA TGGGGTATCC GTCAGCTGCG TGCTCGTCTG    1080
CTGGCACTGG AAACCCTGAT CCAGAACCAG CAGCTGCTGA ACCTGTGGGG CTGCAAAGGT    1140
CGTCTGATCT GCTACACCTC CGTTAAATGG AACGAAACCT GGCGTAACAC CACCAACATC    1200
AACCAGATCT GGGGTAACCT GACCTGGCAG GAATGGGACC AGCAGATCGA CAACGTTTCT    1260
TCCACCATCT ACGAAGAAAT CCAGAAAGCT CAGGTTCAGC AGGAACAGAA CGAAAAAAAA    1320
CTGCTGGAAC TGGACGAATG GGCTTCTCTG TGGAACTGGC TGGACATCAC CAAATGGCTG    1380
CGTAACATCC GTCAGGGCTA CCAGCCGCTG TCCCTGCAGA TCCCGACCCG TCAGCAGTCT    1440
GAAGCTGAAA CTCGGGTCG TACCGGTGAA GGTGGTGGTG ACGAAGGCCG TCCGCGTCTG    1500
ATCCCGTCTC CGCAGGGTTT CCTGCCGCTG CTGTACACCG ACCTGCGTAC CATCATCCTG    1560
```

```
TGGTCCTACC ACCTGCTGTC TAACCTGATC TCTGGTACTC AGACTGTTAT CTCTCACCTG    1620

CGTCTGGGTC TGTGGATTCT GGGTCAGAAA ATCATCGACG CTTGCCGTAT CTGCGCTGCT    1680

GTTATCCACT ACTGGCTGCA GGAACTGCAG AAATCCGCTA CCTCCCTGAT CGACACCTTC    1740

GCTGTTGCAG TTGCTAACTG GACTGACGAC ATCATCCTGG GTATCCAGCG TCTGGGTCGT    1800

GGTATCCTGA ACATCCCGCG TCGTGTTCGC CAGGGCTTCG AACGCTCTCT GCTGTAATAG    1860
```

(2) INFORMATION FOR SEQ ID NO:54:

(i) SEQUENCE CHARACTERISTICS:
        (A) LENGTH: 618 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
                245                 250                 255

Asn Glu Leu Phe Lys Tyr Lys Val Val Arg Val Lys Pro Phe Ser Val
            260                 265                 270

Ala Pro Thr Pro Ile Ala Arg Pro Val Ile Gly Thr Gly Thr His Arg
        275                 280                 285

Glu Lys Arg Ala Val Gly Leu Gly Met Leu Phe Leu Gly Val Leu Ser
    290                 295                 300
```

```
Ala Ala Gly Ser Thr Met Gly Ala Ala Thr Ala Leu Thr Val Gln
305                 310                 315                 320

Thr His Ser Val Ile Lys Gly Ile Val Gln Gln Asp Asn Leu Leu
            325                 330                 335

Arg Ala Ile Gln Ala Gln Gln Glu Leu Leu Arg Leu Ser Val Trp Gly
        340                 345                 350

Ile Arg Gln Leu Arg Ala Arg Leu Leu Ala Leu Glu Thr Leu Ile Gln
        355                 360                 365

Asn Gln Gln Leu Leu Asn Leu Trp Gly Cys Lys Gly Arg Leu Ile Cys
370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Gln Ile
            405                 410                 415

Asp Asn Val Ser Ser Thr Ile Tyr Glu Glu Ile Gln Lys Ala Gln Val
            420                 425                 430

Gln Gln Glu Gln Asn Glu Lys Lys Leu Leu Glu Leu Asp Glu Trp Ala
        435                 440                 445

Ser Leu Trp Asn Trp Leu Asp Ile Thr Lys Trp Leu Arg Asn Ile Arg
450                 455                 460

Gln Gly Tyr Gln Pro Leu Ser Leu Gln Ile Pro Thr Arg Gln Gln Ser
465                 470                 475                 480

Glu Ala Glu Thr Pro Gly Arg Thr Gly Glu Gly Gly Asp Glu Gly
            485                 490                 495

Arg Pro Arg Leu Ile Pro Ser Pro Gln Gly Phe Leu Pro Leu Leu Tyr
            500                 505                 510

Thr Asp Leu Arg Thr Ile Ile Leu Trp Ser Tyr His Leu Leu Ser Asn
        515                 520                 525

Leu Ile Ser Gly Thr Gln Thr Val Ile Ser His Leu Arg Leu Gly Leu
530                 535                 540

Trp Ile Leu Gly Gln Lys Ile Ile Asp Ala Cys Arg Ile Cys Ala Ala
545                 550                 555                 560

Val Ile His Tyr Trp Leu Gln Glu Leu Gln Lys Ser Ala Thr Ser Leu
            565                 570                 575

Ile Asp Thr Phe Ala Val Ala Val Ala Asn Trp Thr Asp Asp Ile Ile
        580                 585                 590

Leu Gly Ile Gln Arg Leu Gly Arg Gly Ile Leu Asn Ile Pro Arg Arg
595                 600                 605

Val Arg Gln Gly Phe Glu Arg Ser Leu Leu
610                 615
```

(2) INFORMATION FOR SEQ ID NO:55:

(i) SEQUENCE CHARACTERISTICS:
        (A) LENGTH: 466 amino acids
        (B) TYPE: amino acid
        (C) STRANDEDNESS: single
        (D) TOPOLOGY: linear (xi) SEQUENCE DESCRIPTION: SEQ ID NO:55:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45
```

-continued

```
Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
                180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Asn Ser Met Glu Gly Glu Leu Thr Cys Asn Ser Thr
                245                 250                 255

Val Thr Ser Ile Ile Ala Asn Ile Asp Ser Asp Gly Asn Gln Thr Asn
            260                 265                 270

Ile Thr Phe Ser Ala Glu Val Ala Glu Leu Tyr Arg Leu Glu Leu Gly
        275                 280                 285

Asp Tyr Lys Leu Ile Glu Val Thr Pro Ile Gly Phe Ala Pro Thr Lys
290                 295                 300

Glu Lys Arg Tyr Ser Ser Ala Pro Val Arg Asn Lys Arg Gly Val Phe
305                 310                 315                 320

Val Leu Gly Phe Leu Gly Phe Leu Ala Thr Ala Gly Ser Ala Met Gly
                325                 330                 335

Ala Ala Ser Leu Thr Leu Ser Ala Gln Ser Arg Thr Leu Leu Ala Gly
            340                 345                 350

Ile Val Gln Gln Gln Gln Leu Leu Asp Val Val Lys Arg Gln Gln
        355                 360                 365

Glu Met Leu Arg Leu Thr Val Trp Gly Thr Lys Asn Leu Gln Ala Arg
        370                 375                 380

Val Thr Ala Ile Glu Lys Tyr Leu Lys Asp Gln Ala Gln Leu Asn Ser
385                 390                 395                 400

Trp Gly Cys Ala Phe Arg Gln Val Cys His Thr Thr Val Pro Trp Val
                405                 410                 415

Asn Asp Ser Leu Thr Pro Asp Trp Asn Asn Met Thr Trp Gln Glu Trp
            420                 425                 430

Glu Lys Arg Val His Tyr Leu Glu Ala Asn Ile Ser Gln Ser Leu Glu
        435                 440                 445

Gln Ala Gln Ile Gln Gln Glu Lys Asn Met Tyr Glu Leu Gln Lys Leu
    450                 455                 460

Asn Ser
465
```

(2) INFORMATION FOR SEQ ID NO:56:

(i) SEQUENCE CHARACTERISTICS:
        (A) LENGTH: 491 amino acids
        (B) TYPE: amino acid
        (C) STRANDEDNESS: single
        (D) TOPOLOGY: linear (xi) SEQUENCE DESCRIPTION: SEQ ID NO:56:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Pro
225                 230                 235                 240

Ser Thr Ala Leu Met Lys Ile Pro Gly Asp Pro Gly Gly Asp Met
                245                 250                 255

Arg Asp Asn Trp Arg Ser Glu Leu Tyr Lys Tyr Lys Val Val Lys Ile
            260                 265                 270

Glu Pro Leu Gly Val Ala Pro Thr Lys Ala Lys Arg Arg Val Val Gln
        275                 280                 285

Arg Glu Lys Arg Ala Val Gly Ile Gly Ala Leu Phe Leu Gly Phe Leu
    290                 295                 300

Gly Ala Ala Gly Ser Thr Met Gly Ala Ala Ser Met Thr Leu Thr Val
305                 310                 315                 320

Gln Ala Arg Gln Leu Leu Ser Gly Ile Val Gln Gln Gln Asn Asn Leu
                325                 330                 335

Leu Arg Ala Ile Glu Ala Gln Gln His Leu Leu Gln Leu Thr Val Trp
            340                 345                 350

Gly Ile Lys Gln Leu Gln Ala Arg Ile Leu Ala Val Glu Arg Tyr Leu
        355                 360                 365
```

Lys Asp Gln Gln Leu Leu Gly Ile Trp Gly Cys Ser Gly Lys Leu Ile
370                 375                 380

Cys Thr Thr Ala Val Pro Trp Asn Ala Ser Trp Ser Asn Lys Ser Leu
385                 390                 395                 400

Glu Gln Ile Trp Asn Asn Met Thr Trp Met Glu Trp Asp Arg Glu Ile
                405                 410                 415

Asn Asn Tyr Thr Ser Leu Ile His Ser Leu Ile Glu Glu Ser Gln Asn
                420                 425                 430

Gln Gln Glu Lys Asn Glu Gln Glu Leu Leu Glu Leu Asp Lys Trp Val
                435                 440                 445

Asn Arg Val Arg Gln Gly Tyr Ser Pro Leu Ser Phe Gln Thr His Leu
                450                 455                 460

Pro Ile Pro Arg Gly Pro Asp Arg Pro Glu Gly Ile Glu Lys Lys Ala
465                 470                 475                 480

Ala Asn Val Thr Val Thr Val Pro Phe Val Trp
                485                 490

(2) INFORMATION FOR SEQ ID NO:57:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (xi) SEQUENCE DESCRIPTION: SEQ ID NO:57:

ATGATCGGTG GTGACATGAA AGACATCTGG CGTAACGAAC TGTTCAAATA CAAAGTTGTT      60

CGTGTTAAAC CGTTCTCTGT TGCTCCGACC CCGATCGCTC GTCCGGTTAT CGGTACTGGC     120

ACCCACCGTG AAAAACGTGC TGTAGGTCTG GGTATGCTGT TCCTGGGCGT TCTGTCTGCA     180

GCAGGTTCCA CTATGGGTGC TGCAGCTACC GCTCTGACCG TACAGACCCA CTCTGTTATC     240

AAAGGTATCG TACAGCAGCA GGACAACCTG CTGCGTGCAA TCCAGGCACA GCAGGAACTG     300

CTGCGTCTGT CTGTATGGGG TATCCGTCAG CTGCGTGCTC GTCTGCTGGC ACTGGAAACC     360

CTGATCCAGA ACCAGCAGCT GCTGAACCTG TGGGGCTGCA AAGGTCGTCT GATCTGCTAC     420

ACCTCCGTTA AATGGAACGA AACCTGGCGT AACACCACCA ACATCAACCA GATCTGGGGT     480

AACCTGACCT GGCAGGAATG GGACCAGCAG ATCGACAACG TTTCTTCCAC CATCTACGAA     540

GAAATCCAGA AGCTCAGGT TCAGCAGGAA CAGAACGAAA AAAAACTGCT GGAACTGGAC     600

GAATGGGCTT CTCTGTGGAA CTGGCTGGAC ATCACCAAAT GGCTGTAATA G              651

(2) INFORMATION FOR SEQ ID NO:58:

(i) SEQUENCE CHARACTERISTICS:
        (A) LENGTH: 215 amino acids
        (B) TYPE: amino acid
        (C) STRANDEDNESS: single
        (D) TOPOLOGY: linear (xi) SEQUENCE DESCRIPTION: SEQ ID NO:58:

Met Ile Gly Gly Asp Met Lys Asp Ile Trp Arg Asn Glu Leu Phe Lys
1               5                   10                  15

Tyr Lys Val Val Arg Val Lys Pro Phe Ser Val Ala Pro Thr Pro Ile
                20                  25                  30

Ala Arg Pro Val Ile Gly Thr Gly Thr His Arg Glu Lys Arg Ala Val
                35                  40                  45

Gly Leu Gly Met Leu Phe Leu Gly Val Leu Ser Ala Ala Gly Ser Thr
                50                  55                  60

```
Met Gly Ala Ala Ala Thr Ala Leu Thr Val Gln Thr His Ser Val Ile
 65                  70                  75                  80

Lys Gly Ile Val Gln Gln Asp Asn Leu Leu Arg Ala Ile Gln Ala
             85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
            115                 120                 125

Asn Leu Trp Gly Cys Lys Gly Arg Leu Ile Cys Tyr Thr Ser Val Lys
            130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
            195                 200                 205

Leu Asp Ile Thr Lys Trp Leu
210                 215

(2) INFORMATION FOR SEQ ID NO:59:

(i) SEQUENCE CHARACTERISTICS:
        (A) LENGTH: 1386 base pairs
        (B) TYPE: nucleic acid
        (C) STRANDEDNESS: single
        (D) TOPOLOGY: linear (xi) SEQUENCE DESCRIPTION: SEQ ID NO:59:

ATGAGTTTTG TGGTCATTAT TCCCGCGCGC TACGCGTCGA CGCGTCTGCC CGGTAAACCA      60

TTGGTTGATA TTAACGGCAA ACCCATGATT GTTCATGTTC TTGAACGCGC GCGTGAATCA     120

GGTGCCGAGC GCATCATCGT GGCAACCGAT CATGAGGATG TTGCCCGCGC CGTTGAAGCC     180

GCTGGCGGTG AAGTATGTAT GACGCGCGCC GATCATCAGT CAGGAACAGA ACGTCTGGCG     240

GAAGTTGTCG AAAAATGCGC ATTCAGCGAC GACACGGTGA TCGTTAATGT GCAGGGTGAT     300

GAACCGATGA TCCCTGCGAC AATCATTCGT CAGGTTGCTG ATAACCTCGC TCAGCGTCAG     360

GTGGGTATGA CGACTCTGGC GGTGCCAATC ACAATGCGG AAGAAGCGTT TAACCCGAAT      420

GCGGTGAAAG TGGTTCTCGA CGCTGAAGGG TATGCACTGT ACTTCTCTCG CGCCACCATT     480

CCTTGGGATC GTGATCGTTT TGCAGAAGGC CTTGAAACCG TTGGCGATAA CTTCCTGCGT     540

CATCTTGGTA TTTATGGCTA CCGTGCAGGC TTTATCCGTC GTTACGTCAA CTGGCAGCCA     600

AGTCCGTTAG AACACATCGA AATGTTAGAG CAGCTTCGTG TTCTGTGGTA CGGCGAAAAA     660

ATCCATGTTG CTGTTGCTCA GGAAGTTCCT GGCACAGGTG TGGATACCCC TGAAGATCTC     720

GACCCGTCGA CGAATTCTAT CGGTGGTGAC ATGAAAGACA TCTGGCGTAA CGAACTGTTC     780

AAATACAAAG TTGTTCGTGT TAAACCGTTC TCTGTTGCTC CGACCCCGAT CGCTCGTCCG     840

GTTATCGGTA CTGGCACCCA CCGTGAAAAA CGTGCTGTAG GTCTGGGTAT GCTGTTCCTG     900

GGCGTTCTGT CTGCAGCAGG TTCCACTATG GGTGCTGCAG CTACCGCTCT GACCGTACAG     960

ACCCACTCTG TTATCAAAGG TATCGTACAG CAGCAGGACA ACCTGCTGCG TGCAATCCAG    1020

GCACAGCAGG AACTGCTGCG TCTGTCTGTA TGGGGTATCC GTCAGCTGCG TGCTCGTCTG    1080

CTGGCACTGG AAACCCTGAT CCAGAACCAG CAGCTGCTGA ACCTGTGGGG CTGCAAAGGT    1140
```

-continued

```
CGTCTGATCT GCTACACCTC CGTTAAATGG AACGAAACCT GGCGTAACAC CACCAACATC      1200

AACCAGATCT GGGGTAACCT GACCTGGCAG GAATGGGACC AGCAGATCGA CAACGTTTCT      1260

TCCACCATCT ACGAAGAAAT CCAGAAAGCT CAGGTTCAGC AGGAACAGAA CGAAAAAAAA      1320

CTGCTGGAAC TGGACGAATG GCTTCTCTG TGGAACTGGC TGGACATCAC CAAATGGCTG      1380

TAATAG                                                                 1386
```

(2) INFORMATION FOR SEQ ID NO:60:

(i) SEQUENCE CHARACTERISTICS:
        (A) LENGTH: 460 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:60:

```
Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
                245                 250                 255

Asn Glu Leu Phe Lys Tyr Lys Val Val Arg Val Lys Pro Phe Ser Val
            260                 265                 270

Ala Pro Thr Pro Ile Ala Arg Pro Val Ile Gly Thr Gly Thr His Arg
        275                 280                 285

Glu Lys Arg Ala Val Gly Leu Gly Met Leu Phe Leu Gly Val Leu Ser
    290                 295                 300
```

-continued

```
Ala Ala Gly Ser Thr Met Gly Ala Ala Thr Ala Leu Thr Val Gln
305                 310                 315                 320

Thr His Ser Val Ile Lys Gly Ile Val Gln Gln Asp Asn Leu Leu
                325                 330                 335

Arg Ala Ile Gln Ala Gln Gln Glu Leu Leu Arg Leu Ser Val Trp Gly
            340                 345                 350

Ile Arg Gln Leu Arg Ala Arg Leu Leu Ala Leu Glu Thr Leu Ile Gln
        355                 360                 365

Asn Gln Gln Leu Leu Asn Leu Trp Gly Cys Lys Gly Arg Leu Ile Cys
370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Ile
                405                 410                 415

Asp Asn Val Ser Ser Thr Ile Tyr Glu Glu Ile Gln Lys Ala Gln Val
            420                 425                 430

Gln Gln Glu Gln Asn Glu Lys Lys Leu Leu Glu Leu Asp Glu Trp Ala
        435                 440                 445

Ser Leu Trp Asn Trp Leu Asp Ile Thr Lys Trp Leu
450                 455                 460

(2) INFORMATION FOR SEQ ID NO:61:

(i) SEQUENCE CHARACTERISTICS:
        (A) LENGTH: 873 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:61:

Met Ile Val Thr Met Arg Ala Met Gly Lys Arg Asn Arg Lys Leu Gly
1               5                   10                  15

Ile Leu Tyr Ile Val Met Ala Leu Ile Ile Pro Cys Leu Ser Ser Ser
                20                  25                  30

Gln Leu Tyr Ala Thr Val Tyr Ala Gly Val Pro Val Trp Glu Asp Ala
            35                  40                  45

Ala Pro Val Leu Phe Cys Ala Ser Asp Ala Asn Leu Thr Ser Thr Glu
50                  55                  60

Lys His Asn Val Trp Ala Ser Gln Ala Cys Val Pro Thr Asp Pro Thr
65                  70                  75                  80

Pro His Glu Tyr Leu Leu Thr Asn Val Thr Asp Asn Phe Asn Ile Trp
                85                  90                  95

Glu Asn Tyr Met Val Glu Gln Met Gln Glu Asp Ile Ile Ser Leu Trp
                100                 105                 110

Asp Gln Ser Leu Lys Pro Cys Ile Gln Met Thr Phe Met Cys Ile Gln
            115                 120                 125

Met Asn Cys Thr Asp Ile Lys Asn Asn Asn Thr Ser Gly Thr Glu Asn
130                 135                 140

Arg Thr Ser Ser Ser Glu Asn Pro Met Lys Thr Cys Glu Phe Asn Ile
145                 150                 155                 160

Thr Thr Val Leu Lys Asp Lys Lys Glu Lys Lys Gln Ala Leu Phe Tyr
                165                 170                 175

Val Ser Asp Leu Thr Lys Leu Ala Asp Asn Asn Thr Thr Asn Thr Met
            180                 185                 190

Tyr Thr Leu Ile Asn Cys Asn Ser Thr Thr Ile Lys Gln Ala Cys Pro
```

-continued

```
                195                 200                 205
Lys Val Ser Phe Glu Pro Ile Pro Ile Tyr Tyr Cys Ala Pro Ala Gly
    210                 215                 220
Tyr Ala Ile Phe Lys Cys Asn Ser Ala Glu Phe Asn Gly Thr Gly Lys
225                 230                 235                 240
Cys Ser Asn Ile Ser Val Val Thr Cys Thr His Gly Ile Lys Pro Thr
                245                 250                 255
Val Ser Thr Gln Leu Ile Leu Asn Gly Thr Leu Ser Lys Glu Lys Ile
                260                 265                 270
Arg Ile Met Gly Lys Asn Ile Ser Asp Ser Gly Lys Asn Ile Ile Val
                275                 280                 285
Thr Leu Ser Ser Asp Ile Glu Ile Thr Cys Val Arg Pro Gly Asn Asn
                290                 295                 300
Gln Thr Val Gln Glu Met Lys Ile Gly Pro Met Ala Trp Tyr Ser Met
305                 310                 315                 320
Ala Leu Gly Thr Gly Ser Asn Arg Ser Arg Val Ala Tyr Cys Gln Tyr
                325                 330                 335
Asn Thr Thr Glu Trp Glu Lys Ala Leu Lys Asn Thr Ala Glu Arg Tyr
                340                 345                 350
Leu Glu Leu Ile Asn Asn Thr Glu Gly Asn Thr Thr Met Ile Phe Asn
                355                 360                 365
Arg Ser Gln Asp Gly Ser Asp Val Glu Val Thr His Leu His Phe Asn
                370                 375                 380
Cys His Gly Glu Phe Phe Tyr Cys Asn Thr Ser Glu Met Phe Asn Tyr
385                 390                 395                 400
Thr Phe Leu Cys Asn Gly Thr Asn Cys Asn Asn Thr Gln Ser Ile Asn
                405                 410                 415
Ser Ala Asn Gly Met Ile Pro Cys Lys Leu Lys Gln Val Val Arg Ser
                420                 425                 430
Trp Met Arg Gly Gly Ser Gly Leu Tyr Ala Pro Pro Ile Pro Gly Asn
                435                 440                 445
Leu Thr Cys Ile Ser His Ile Thr Gly Met Ile Leu Gln Met Asp Ala
                450                 455                 460
Pro Trp Asn Lys Thr Glu Asn Thr Phe Arg Pro Ile Gly Gly Asp Met
465                 470                 475                 480
Lys Asp Ile Trp Arg Asn Glu Leu Phe Lys Tyr Lys Val Val Arg Val
                485                 490                 495
Lys Pro Phe Ser Val Ala Pro Thr Pro Ile Ala Arg Pro Val Ile Gly
                500                 505                 510
Thr Gly Thr His Arg Glu Lys Arg Ala Val Gly Leu Gly Met Leu Phe
                515                 520                 525
Leu Gly Val Leu Ser Ala Ala Gly Ser Thr Met Gly Ala Ala Ala Thr
                530                 535                 540
Ala Leu Thr Val Gln Thr His Ser Val Ile Lys Gly Ile Val Gln Gln
545                 550                 555                 560
Gln Asp Asn Leu Leu Arg Ala Ile Gln Ala Gln Gln Glu Leu Leu Arg
                565                 570                 575
Leu Ser Val Trp Gly Ile Arg Gln Leu Arg Ala Arg Leu Leu Ala Leu
                580                 585                 590
Glu Thr Leu Ile Gln Asn Gln Gln Leu Leu Asn Leu Trp Gly Cys Lys
                595                 600                 605
Gly Arg Leu Ile Cys Tyr Thr Ser Val Lys Trp Asn Glu Thr Trp Arg
                610                 615                 620
```

```
Asn Thr Thr Asn Ile Asn Gln Ile Trp Gly Asn Leu Thr Trp Gln Glu
625                 630                 635                 640

Trp Asp Gln Gln Ile Asp Asn Val Ser Ser Thr Ile Tyr Glu Glu Ile
                645                 650                 655

Gln Lys Ala Gln Val Gln Gln Glu Gln Asn Glu Lys Lys Leu Leu Glu
            660                 665                 670

Leu Asp Glu Trp Ala Ser Leu Trp Asn Trp Leu Asp Ile Thr Lys Trp
        675                 680                 685

Leu Trp Tyr Ile Lys Ile Ala Ile Ile Ile Val Gly Ala Leu Ile Gly
    690                 695                 700

Val Arg Ile Val Met Ile Val Leu Asn Leu Val Arg Asn Ile Arg Gln
705                 710                 715                 720

Gly Tyr Gln Pro Leu Ser Leu Gln Ile Pro Thr Arg Gln Gln Ser Glu
                725                 730                 735

Ala Glu Thr Pro Gly Arg Thr Gly Glu Gly Gly Gly Asp Glu Gly Arg
            740                 745                 750

Pro Arg Leu Ile Pro Ser Pro Gln Gly Phe Leu Pro Leu Leu Tyr Thr
        755                 760                 765

Asp Leu Arg Thr Ile Ile Leu Trp Ser Tyr His Leu Leu Ser Asn Leu
    770                 775                 780

Ile Ser Gly Thr Gln Thr Val Ile Ser His Leu Arg Leu Gly Leu Trp
785                 790                 795                 800

Ile Leu Gly Gln Lys Ile Ile Asp Ala Cys Arg Ile Cys Ala Ala Val
                805                 810                 815

Ile His Tyr Trp Leu Gln Glu Leu Gln Lys Ser Ala Thr Ser Leu Ile
            820                 825                 830

Asp Thr Phe Ala Val Ala Val Ala Asn Trp Thr Asp Asp Ile Ile Leu
        835                 840                 845

Gly Ile Gln Arg Leu Gly Arg Gly Ile Leu Asn Ile Pro Arg Arg Val
    850                 855                 860

Arg Gln Gly Phe Glu Arg Ser Leu Leu
865                 870
```

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:62:

YCTYTAGAGA GTGTCCCATT                                                      20

(2) INFORMATION FOR SEQ ID NO:63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:63:

GTGCTWCCTG CTGCACTTA                                                       19

(2) INFORMATION FOR SEQ ID NO:64:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (xi) SEQUENCE DESCRIPTION: SEQ ID NO:64:

AAGTTGCTCA AGAGGTGGTA                                              20

(2) INFORMATION FOR SEQ ID NO:65:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:65:

CCTTAGAGGC ACTTGAGGT                                               19

(2) INFORMATION FOR SEQ ID NO:66:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:66:

CCARAGCAGT AAGTAACGC                                               19

(2) INFORMATION FOR SEQ ID NO:67:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:67:

RTTAAYTAAT TGTAACTCCA CAA                                          23

(2) INFORMATION FOR SEQ ID NO:68:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:68:

GAMTYTATGC ACCTCCCATC                                              20

(2) INFORMATION FOR SEQ ID NO:69:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:69:

GACATAACTA AATGGTTGTG G                                            21

(2) INFORMATION FOR SEQ ID NO:70:

(i) SEQUENCE CHARACTERISTICS:
            (A) LENGTH: 23 base pairs
            (B) TYPE: nucleic acid
            (C) STRANDEDNESS: single
            (D) TOPOLOGY: linear
```

(xi) SEQUENCE DESCRIPTION: SEQ ID NO:70:

ATACTTGARA GRTTAAGRAG AAT                                          23

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

ATGCCATGTG TACAAGTAAC                                              20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:72:

ATACACTATT GTGCTCCARC                                              20

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:73:

AGTTCTCCAT ATATCTTTCA TR                                           22

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:74:

AACATAACTG GAATGATYCT AC                                           22

(2) INFORMATION FOR SEQ ID NO:75:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:75:

CTGAGRTCCG TGTACAAC                                                18

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:76:

ATTAGGCAGG GATATCAACC                                            20

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:77:

CCTACTCCAG GTGCRCAT                                              18

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:78:

CAWCACAAGC CTGYGTTCC                                             19

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:79:

ATGTCTTCVT GCATTTGKTC                                            20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:80:

AATGGGACAC TCTCTARAGR                                            20

(2) INFORMATION FOR SEQ ID NO:81:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:81:

TTAACTGTCA TGGAGAATTC TT                                         22

(2) INFORMATION FOR SEQ ID NO:82:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:82:

AAGAATTCTC CATGACAGTT AA                                         22

(2) INFORMATION FOR SEQ ID NO:83:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:83:

TAAGTGCAGC AGGWAGCAC                                                   19

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:84:

CCACAACCAT TTAGTTATGT C                                                21

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:85:

TACCACCTCT TGAGCAACTT                                                  20

(2) INFORMATION FOR SEQ ID NO:86:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:86:

CYTGTCTAAT YCTYCTTGG                                                   19

(2) INFORMATION FOR SEQ ID NO:87:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:87:

TGGCCTGGTA CAGCATGGG                                                   19

(2) INFORMATION FOR SEQ ID NO:88:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:88:

GTACGAATTC CATGGAAGGG GAGTTGACCT GC                                    32

(2) INFORMATION FOR SEQ ID NO:89:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

```
TATTGGATCC TTATCAGCTA TTTAGTTTTT GTAG                               34
```